(12) United States Patent
Snow et al.

(10) Patent No.: US 6,770,639 B2
(45) Date of Patent: Aug. 3, 2004

(54) HETEROCYCLIC COMPOUNDS USEFUL AS INHIBITORS OF TYROSINE KINASES

(75) Inventors: Roger John Snow, Danbury, CT (US); Mario Cardozo, Brookfield, CT (US); Daniel Goldberg, Redding, CT (US); Abdelhakim Hammach, Danbury, CT (US); Tina Morwick, New Milford, CT (US); Neil Moss, Ridgefield, CT (US); Usha R. Patel, Brookfield, CT (US); Anthony S. Prokopowicz, III, Stormville, NY (US); Hidenori Takahashi, LaGrangeville, NY (US); Matt Aaron Tschantz, Newtown, CT (US); Xiao-Jun Wang, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/292,026

(22) Filed: Nov. 12, 2002

(65) Prior Publication Data

US 2003/0166929 A1 Sep. 4, 2003

Related U.S. Application Data

(60) Division of application No. 09/921,509, filed on Aug. 2, 2001, now Pat. No. 6,506,769, which is a continuation-in-part of application No. 09/679,156, filed on Oct. 5, 2000, now abandoned.
(60) Provisional application No. 60/157,922, filed on Oct. 6, 1999.

(51) Int. Cl.$^7$ .................. A61K 31/33; A61K 31/44; C07D 217/72; C07D 401/00
(52) U.S. Cl. .................. 514/183; 514/293; 514/290; 514/393; 514/397; 546/82; 546/141; 546/148; 546/273.1
(58) Field of Search ............... 514/183, 293, 514/290, 393, 397; 546/82, 141, 148, 273.1

(56) References Cited

U.S. PATENT DOCUMENTS

| | | | | |
|---|---|---|---|---|
| 4,176,184 A | * | 11/1979 | Austel et al. | 424/248.52 |
| 5,646,153 A | | 7/1997 | Spada et al. | |
| 6,506,709 B1 | * | 1/2003 | Yamazaki | 514/293 |
| 6,506,769 B2 | * | 1/2003 | Snow et al. | 514/293 |

FOREIGN PATENT DOCUMENTS

| | | |
|---|---|---|
| DE | 27 32 951 A | 2/1979 |
| DE | 2732951 * | 2/1979 |
| DE | 34 10 168 A1 | 9/1985 |
| EP | 0 322 746 A1 | 7/1989 |
| WO | WO 98/28281 | 7/1998 |
| WO | WO 98/54157 | 12/1998 |
| WO | WO 99/09845 | 3/1999 |
| WO | WO 99/24035 | 5/1999 |

OTHER PUBLICATIONS

Cecil Textbook of Medicine, 20th Edition, vol. 1, pp. 1005–10(1996).*
Uckum et al, Current Cancer Drug Taegets, 1, 59–71(2001).*
Liu et al(PubMed 12447698, also cited as Oncogene, 21/54, 8347–50(2002).*
Granata et al(PubMed 1286405, also cited as Int. Arch. Allergy. Immunol. 131/3, 153–63(2003).*
Isono Takikita et al(PubMed Abstract 12819032, also cited as Am. J. Pathol. 163/1,277–86(2003).*
Ding et al(PubMed Abstract 12881526, also cited as J. Biol. Chem. Jul. 24(2003).*
Burchat, A. F., et al; "Pyrrolo[2,3–d]pyrimidines Containing an Extended 5–Substituent as Potent and Selective Inhibitors of Ick II"; Bioorganic & Medicinal Chemistry Letters 10 (2000) 2171–2174.
Arnold, L. D., et al; "Pyrrolo[2,3–d]pyrimidines Containing an Extended 5–Substituent as Potent and Selective Inhibitors of Ick I"; Bioorganic & Medicinal Chemistry Letters 10 (2000) 2167–2170.
Traxler, P. M.; "Protein tyrosine kinase inhibitors in cancer treatment"; Exp. Opin. Ther. Patents; 1997, 7(6), p 571–588.
Showalter, H. D. H., et al; "Small Molecule Inhibitors of the Platelet–Derived Growth Factor Receptor, the Fibroblast Growth Factor Receptor, and Src Family Tyrosine Kinases"; Pharmacol. Ther. vol. 76, Nos. 1–3, p 55–71 1997.
Traxler, P; "Tyrosine kinase inhibitors in cancer treatment (Part II)";Exp. Opin. Ther. Patents, 1998, 8(12), p 1599–1625.

* cited by examiner

Primary Examiner—Richard L. Raymond
Assistant Examiner—Sudhaker B. Patel
(74) Attorney, Agent, or Firm—Robert P. Raymond; Michael Morris; Philip I. Datlow

(57) ABSTRACT

Disclosed are novel compounds of formula (I):

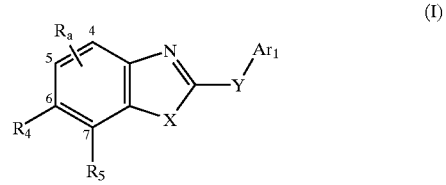

wherein $Ar_1$, $R_a$, $R_4$, $R_5$, X and Y are defined below, which are useful as inhibitors of certain protein tyrosine kinases and are thus useful for treating diseases associated with such kinases, for example, diseases resulting from inappropriate cell proliferation, which include autoimmune diseases, chronic inflammatory diseases, allergic diseases, transplant rejection and cancer, as well as conditions resulting from cerebral ischemia, such as stroke. Also disclosed are processes for preparing these compounds, novel intermediates useful in these processes and compositions comprising compounds of the formula (I).

22 Claims, No Drawings

HETEROCYCLIC COMPOUNDS USEFUL AS INHIBITORS OF TYROSINE KINASES

This application is a divisional of U.S. application Ser. No. 09/921,509, filed Aug. 2, 2001 now U.S. Pat. No. 6,506,769, which is a continuation-in-part of U.S. application Ser. No. 09/679,156, filed Oct. 5, 2000 now abandoned, which claims benefit from U.S. Provisional Application No. 60/157,922, filed Oct. 6, 1999, all of which applications are herein incorporated by reference in their entirety.

TECHNICAL FIELD OF THE INVENTION

This invention relates to substituted compounds of formula (I):

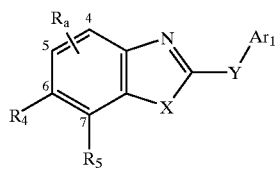

wherein $Ar_1$, $R_a$, $R_4$, $R_5$, X and Y are defined below, which are useful as inhibitors of certain protein tyrosine kinases and are thus useful for treating diseases resulting from inappropriate cell proliferation, which include autoimmune diseases, chronic inflammatory diseases, allergic diseases, transplant rejection and cancer, as well as conditions resulting from cerebral ischemia, such as stroke. This invention also relates to processes for preparing these compounds and to pharmaceutical compositions comprising these compounds.

BACKGROUND OF THE INVENTION

Tyrosine kinases play an essential role in the regulation of cell signaling and cell proliferation by phosphorylating tyrosine residues of peptides and proteins. Inappropriate activation of tyrosine kinases is known to be involved in a variety of disease states, including immunologic and oncologic disorders.

It has been well established that T cells play an important role in regulating the immune response (F. Powrie and R. L. Coffman, *Immunol. Today*, 1993, 14, 270). Activation of T cells is often the initiating event in many inflammatory and autoimmune diseases. In addition to their role in immune surveillance, T cells can become autoreactive by recognizing self-antigens and thereby cause autoimmune disease such as rheumatoid arthritis and inflammatory bowel disease.

The T cell receptor (TCR) is the antigen-specific component of the T cell and is activated when the receptor is engaged with foreign or self-antigenic peptides. When the TCR is activated a series of enzyme-mediated signal transduction cascades is initiated which results in the production of pro-inflammatory cytokines such as interleukin-2 (IL-2).

The release of IL-2 is critically important since this lymphokine is required for T-lymphocyte proliferation, differentiation, and effector function. Clinical studies have shown that interference with IL-2 activity effectively suppresses immune response in vivo (T. A. Waldmann, *Immunol. Today*, 1993, 14, 270). Accordingly, agents which inhibit T-lymphocyte activation and subsequent IL-2 production, or block the activity of IL-2 are therapeutically useful for selectively suppressing immune response in a patient in need of such immunosuppression.

The eight members of the src family of tyrosine kinases are src, lck, fyn, lyn, hck, fgr, blk and yes (J. B. Bolen, J. S. Brugge, *Ann. Rev. Immunol.*, 1997, 15, 371). These can be divided into 2 groups based on their pattern of tissue expression. Src, fyn and yes have a broad distribution while expression of lck, lyn, hck, fgr, and blk is largely limited to hemopoietic cells. The therapeutic effects of inhibiting kinases of the src family can be ascertained by linking functional defects seen in gene disruption studies in mice. Src(−/−) mice had severe abnormalities in bone remodeling. Inhibition of src may therefore be useful in treating osteoporosis. Lck(−/−) mice display a complete lack of CD4+ cells and are unable to mount antigen-dependent immune responses.

A kinase of particular interest is p56lck, which is only expressed in T-cells. Within the TCR signal transduction cascade the tyrosine kinase p56lck is a required element to initiate the activation response from the TCR intracellular domains to other signaling proteins. For example, T cells which lack the p56lck protein are unable to signal through the T cell receptor (D. B. Straus and A. Weiss, *Cell*, 1992, 70, 585). Transfection of p56lck back into these cell lines restores TCR responsiveness. Also, it has been shown in mice that inactivation of the p56lck gene leads to lack of proper thymocyte development (T. J. Molina et al., *Nature*, 1992, 357, 161).

The conclusion drawn from these studies is that p56lck plays a crucial role in T cell maturation and antigen-induced T-cell activation. Therefore, an agent blocking p56lck would effectively block T cell function, act as an immunosuppressive agent and have potential utility in autoimmune diseases, for example rheumatoid arthritis, multiple sclerosis, lupus, transplant rejection and allergic diseases (J. H. Hanke et al., *Inflamm. Res.*, 1995, 44, 357).

Inhibitors of other members of the src family of non-receptor tyrosine kinases are also useful for treating various disease states. Src is present in osteoclasts, and is important in bone remodeling. For example, inactivation of p60src diminishes bone resorption by osteoclasts (P. Soriano et al., *Cell* 1991, 64, 693, B. F. Boyce et al. *J. Clin. Invest* 1992, 90, 1622), it is therefore possible that inhibitors of the kinase activity of p60src are useful in the treatment of osteoporosis, Paget's disease and inflammation of bones and joints. Src kinases have been found to be activated in tumors, including breast and colon cancers, melanoma and sarcoma. For example, a number of primary tumors and tumor cell lines from patients with breast cancer, colon cancer, melanoma and sarcoma have been shown to have elevated src kinase activity, and activating src mutations are seen in some advanced colon cancers. Inhibitors of src kinase had significant antiproliferative activity against cancer cell lines (M. M. Moasser et al., *Cancer Res.*, 1999, 59, 6145) and inhibited the transformation of cells to an oncogenic phenotype (R. Kami et al., *Oncogene*, 1999, 18, 4654) suggesting that src kinase inhibitors may be useful anti-cancer agents.

Src inhibitors have also been reported to be effective in an animal model of cerebral ischemia (R. Paul et al. *Nature Medicine* 2001, 7, 222), suggesting that src kinase inhibitors may thus be useful in treating conditions involving cerebral ischemia. For example, src kinase inhibitors may be useful in reducing brain damage following stroke.

In addition, src family kinases participate in signal transduction in several cell types. For example, fyn, like lck, is involved in T-cell activation. Hck and fgr are involved in Fc gamma receptor mediated oxidative burst of neutrophils. Src and lyn are believed to be important in Fc epsilon induced degranulation of mast cells, and so may play a role in asthma and other allergic diseases. The kinase lyn is known to be involved in the cellular response to DNA damage induced by UV light (T. Hiwasa, *FEBS Lett.* 1999, 444, 173) or ionizing radiation (S. Kumar, *J. Biol Chem,* 1998, 273, 25654). Inhibitors of lyn kinase may thus be useful as potentiators in radiation therapy.

Platelet derived growth factor is a potent mitogen for smooth muscle cells. Its receptor (PDGFR) is a member of the receptor tyrosine kinase family (L. Claesson-Welsh, *J. Biol Chem,* 1994, 269, 32023). PDGF is involved in atherosclerosis and restenosis (K. E. Bornfeldt, *Trends Cardiovasc. Med.,* 1996, 6, 143). In addition, receptor tyrosine kinases including PDGFR kinase have been implicated as contributing factors in cancer (A. Levitzki and A. Gazit, *Science,* 1995, 267, 1782) including ovarian (M. B. Dabrow et al., *Gynecologic Oncology,* 1998, 71, 29) and prostate (S. M. Sintich et al., *Endocrinology,* 1999, 140, 3411) cancers and glioblastoma (B. J. Silver, *BioFactors,* 1992 3, 217). Inhibitors of PDGFR kinase are thus useful in the treatment of fibrotic diseases, restenosis and PDGF-dependent tumors.

Reports have appeared in the literature of agents that inhibit the kinase activity of p56lck kinase and thus inhibit T cell activation. These include the natural product lavendustin A, and analogs (M. S. Smyth, *J. Med. Chem.,* 1993, 36, 3010), the natural product damnacanthal (C. R. Faltynek et al., *Biochemistry,* 1995, 34, 12404), and a 1-methoxy agroclavine isolated from a fungal extract (R. Padmanabha et al. *Bioorganic and Med. Chem. Letters,* 1998, 8, 569). Other inhibitors reported include WIN 61651 (*J. Enzyme Inhibition,* 1995, 9, 111) pyrazolopyrimidines PP1 and PP2 (Hanke et al. *J. Biol Chem,* 1996, 271, 695) and indanone and indandione derivatives (J. L. Bullington et al., *Bioorganic and Med. Chem. Letters,* 1998, 8, 2489).

A. P. Spader et al. (WO 98/54157, 1998) describe quinoline and quinoxaline compounds that inhibit p56lck and PDGFR kinase. Fused polycyclic 2-aminopyrimidine derivatives that inhibit p56lck are reported by J. M. Davis et al. (WO 98/28281, 1998). J. Das et al. claim a series of benzothiazole amides as inhibitors of lck and other src family kinases (WO 99/24035, 1999). Inhibitors of PDGFR kinase and src-family kinases were reviewed by H. D. H. Showalter, A. J. Kraker, *Pharmacol. Ther.,* 1997, 76, 55. Several patents on inhibitors of lck are reviewed in P. M. Traxler, *Exp. Opin. Ther. Patents,* 1997, 7, 571,and P. M. Traxler, *Exp. Opin. Ther. Patents,* 1998, 8, 1599.

U.S. Pat. No. 4,176,184 discloses imidazoisoquinolinediones, which are described as being useful as cardiotonics, hypotensives, antithrombotics and antiarrhythmics. DE 3410168 A1 discloses imidazoisoquinoline-dione derivatives, these compounds are described as being useful as cardiotonic agents in which the substituent on the fused imidazole ring is a pyridine ring bridged to the imidazole carbon by a $C_1$–$C_4$ alkyl group, a vinyl group or a chemical bond. EP 322 746 A1 discloses heterocyclic lactam derivatives described as being useful as cardiotonic agents, antihypertensive agents and vasodilators.

The compounds of the present invention represent a novel structural class, which is distinct from previously reported tyrosine kinase inhibitors.

BRIEF SUMMARY OF THE INVENTION

The work cited above supports the principle that inhibition of the kinases mentioned above will be beneficial in the treatment of various disease states.

It is therefore an object of the invention to provide novel compounds which inhibit PDGFR kinase and the src-family kinases including lck, src, fyn, lyn, hck, fgr, blk and yes.

It is a further object of the invention to provide methods for treating diseases and pathological conditions mediated by src-family tyrosine kinases and PDGFR kinase such as autoimmune diseases, transplant rejection, psoriasis, osteoporosis, Paget's disease, cancer, including src-dependent tumors and PDGF-dependent tumors, cerebral ischemic conditions, atherosclerosis, restenosis and allergic diseases, using the novel compounds of the invention.

It is yet a further object of the invention to provide processes of preparation of the above-mentioned novel compounds and pharmaceutical compositions comprising the same.

DETAILED DESCRIPTION OF THE INVENTION

The src-family tyrosine kinases and PDGFR kinase discussed above exhibit some homology in their amino acid structure. It is contemplated that due to structural differences between individual src-family kinases and PDGFR kinase, different compounds of the invention may have different inhibitory potencies against individual tyrosine kinases. Thus some of compounds of the invention may also be expected to be most effective in treating diseases mediated by tyrosine kinases that they inhibit most potently. Particular compounds disclosed herein have been shown to be active inhibitors of p56lck kinase, p60src kinase and PDGFR kinase. See the section entitled "Assessment of Biological Properties" disclosed herein.

In its broadest generic aspect, the invention provides novel compounds of the formula I:

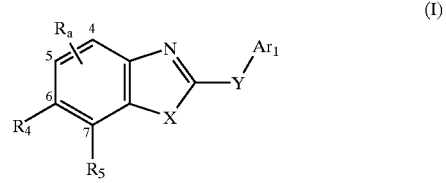

(I)

wherein:

$Ar_1$ is an aromatic or nonaromatic carbocycle, heteroaryl or heterocycle; wherein said carbocycle, heteroaryl or heterocycle is optionally substituted by one or more $R_1$, $R_2$ and $R_3$;

X is NH, N—$C_{1-3}$alkyl, N-cyclopropyl, S or O;

Y is $NR_{15}$, S or O;

$R_a$ is H, $C_{1-10}$alkyl, $C_{2-10}$alkenyl or $C_{2-10}$alkynyl, each of which may be branched or cyclic; or $R_a$ is aryl or heteroaryl; wherein each $R_a$ is independently optionally substituted with one or more $C_{1-6}$alkyl, $C_{1-6}$ alkoxy, halogen, OH, oxo, $NR_{10}R_{11}$, aryl or heteroaryl, each aryl or heteroaryl being optionally substituted with one or more groups selected from halogen, OH, $C_{1-3}$alkyl, $C_{1-3}$alkoxy, hydroxy$C_{1-3}$alkyl and $(CH_2)_m NR_{10}R_{11}$; and wherein $R_a$ is attached at the 4- or 5- position;

$R_1$ and $R_2$ are the same or different and selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-($C_{1-3}$) alkylaminosulfonyl, $NR_{10}R_{11}$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from oxo, OH, $NR_{10}R_{11}$, $C_{1-6}$ branched or unbranched alkyl, $C_{3-7}$cycloalkyl, phenyl, naphthyl, heteroaryl, aminocarbonyl and mono- or di($C_{1-3}$)alkylaminocarbonyl;

$R_3$ is H, halogen, OH, $(CH_2)_nNR_{10}R_{11}$, $CONR_{10}R_{11}$, $(CH_2)_nCO_2R_{12}$; $C_{1-3}$alkyl optionaslly substituted with OH, $C_{1-3}$ alkoxy optionally halogenated or $C_{1-3}$ alkylthio;

$R_4$ and $R_5$ together with the atoms to which they are attached complete a fused ring system of the formulas A or B:

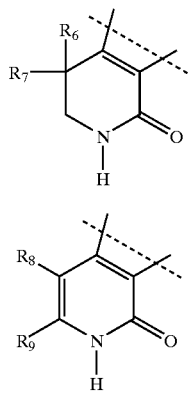

$R_6$ is $C_{1-3}$alkyl or H;
$R_7$ is $C_{1-6}$alkyl branched or unbranched or H;
$R_8$ is H, $C_{1-6}$alkyl branched or unbranched, saturated or unsaturated, optionally substituted with phenyl, OH or $C_{1-3}$alkoxy; or $R_8$ is $(CH_2)_mNR_{10}R_{11}$, $(CH_2)_mNR_{10}COR_{12}$, $(CH_2)_nCO_2R_{12}$, $(CH_2)_nCONR_{10}R_{11}$; or $R_8$ is phenyl or heteroaryl, each being optionally substituted with $C_{1-3}$alkyl, $C_{1-3}$alkoxy, OH, —$SO_3H$ or halogen;

$R_9$ is H, CN or $CONR_{10}R_{11}$; or $R_9$ is $C_{1-10}$alkyl branched or unbranched, $C_{3-10}$cycloalkyl, $C_{5-7}$cycloalkenyl, $C_{2-6}$ alkenyl, $C_{2-6}$ alkynyl each being optionally substituted with one or more $C_{3-10}$cycloalkyl, $C_{3-10}$cycloalkylidene, $C_{5-7}$cycloalkenyl, halogen, OH, oxo, CN, $C_{1-3}$alkoxy, $C_{1-3}$acyloxy, $NR_{10}R_{11}$, $NR_{10}CONR_{10}R_{11}$, $NR_{10}C(=NR_{10})NR_{10}R_{11}$, $NR_{10}COR_{12}$, $NR_{10}S(O)_pR_{12}$, $SR_{12}$, $CONR_{10}R_{11}$, $CO_2R_{12}$, $C(R_{10})=NNR_{10}R_{11}$, $C(R_{10})=NNR_{10}CONR_{10}R_{11}$, aryloxy, arylthio, aryl or heteroaryl; wherein each aryloxy, arylthio, aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;
or $R_9$ is aryl, heteroaryl, or heterocycle, wherein each aryl, heteroaryl or heterocycle is optionally substituted with one to three groups selected from $C_{1-3}$alkyl optionally substituted with phenyl or $NR_{10}C(=NR_{10})NR_{10}R_{11}$, $C_{1-3}$alkoxy, halogen, CN, oxo, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 5 or 6 membered aromatic or nonaromatic carbocyclic ring optionally substituted by one or two $C_{1-3}$alkyl, OH, oxo or $(CH_2)_nNR_{10}R_{11}$, or optionally spiro-fused to a 1,3 dioxolane group or 1,3 dithiolane group, each 1,3 dioxolane group or 1,3 dithiolane group optionally substituted by $C_{1-6}$alkyl, $C_{1-6}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, aryl$C_{1-3}$alkyl or heteroaryl are optionally substituted with OH, $C_{1-3}$alkoxy, CN, $NO_2$, $C_{1-3}$acyloxy, $CO_2R_{12}$, $NR_{13}R_{14}$, $O(CH_2)_{2-4}NR_{13}R_{14}$, aryl or heteroaryl;

or $R_{10}$ and $R_{11}$ together form a 3-7 member alkylene chain completing a ring about the N atom to which they are attached; wherein said alkylene chain is optionally interrupted by O, $S(O)_p$, and $NR_{13}$; and wherein said ring is optionally substituted by $C_{1-3}$ alkyl, $C_{1-3}$alkoxy, OH, —$(CH_2)_nNR_{13}R_{14}$, $CONR_{13}R_{14}$ or $NR_{13}COR_{14}$;

$R_{12}$ is H, $C_{1-6}$alkyl or $C_{3-8}$cycloalkyl wherein each alkyl or cycloalkyl is optionally substituted with phenyl, OH, $C_{1-3}$alkoxy or $NR_{13}R_{14}$; or $R_{12}$ is phenyl or heterocycle, optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$;

$R_{15}$ is H or $C_{1-3}$ alkyl;

m is 1–4; n is 0–3 and p is 0–2; and the pharmaceutically acceptable acid or salt derivatives thereof.

In one embodiment of the invention, there are provided compounds of the formula (I) described above, wherein:

$Ar_1$ is a) a cycloalkyl group selected from cyclopropyl, cyclobutyl, cyclopentanyl, cyclohexanyl, cycloheptanyl;

b) a cycloalkenyl group selected from cyclopentenyl, cyclohexenyl, cycloheptenyl;

c) phenyl, naphthyl; indanyl, indenyl, dihydronaphthyl, tetrahydronaphthyl, fluorenyl;

d) heteroaryl selected from pyridinyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl,or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or e) a heterocycle selected from pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$;

$R_a$ is H, $C_{1-6}$alkyl, $C_{2-5}$alkenyl, $C_{2-5}$alkynyl, phenyl or heteroaryl selected from pyridinyl, pyridazinyl, pyrimidinyl, pyrazinyl, oxazolyl, pyrazolyl, imidazolyl, furyl, thiazolyl and thienyl; each $R_a$ being optionally substituted with one or more phenyl, halogen, $C_{1-3}$alkyl, $C_{1-3}$ alkoxy, OH, oxo, or $NR_{10}R_{11}$; wherein $R_a$ is at the 4-position;

$R_1$ and $R_2$ are as hereinabove defined;

$R_3$ is H, halogen, methyl, methoxy, hydroxymethyl or OH;

$R_8$ is H, $C_{1-3}$alkyl branched or unbranched, saturated or unsaturated, optionally substituted with OH; or $R_8$ is $(CH_2)_{2-3}NR_{10}R_{11}$, $(CH_2)_nCO_2R_{12}$ or $(CH_2)_nCONR_{10}R_{11}$;

$R_9$ is CN or $CONR_{10}R_{11}$; or $R_9$ is $C_{1-3}$alkyl branched or unbranched, $C_{2-4}$ alkenyl, $C_{2-4}$alkynyl each being optionally substituted with one or more $C_{5-7}$cycloalkyl, $C_{5-7}$cycloalkylidene, $C_{5-7}$cycloalkenyl, OH, CN, $C_{1-3}$acyloxy, $NR_{10}R_{11}$, $NR_{10}CONR_{10}R_{11}$, $NR_{10}C(=NR_{10})NR_{10}R_{11}$, $NR_{10}COR_{12}$, $NR_{10}S(O)_pR_{12}$, $CONR_{10}R_{11}$, $CO_2R_{12}$, $C(R_{10})=NNR_{10}R_{11}$, $C(R_{10})=NNR_{10}CONR_{10}R_{11}$, aryl or heteroaryl; wherein each aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl, heteroaryl or heterocycle, each optionally substituted with one to three groups selected from $C_{1-3}$alkyl optionally substituted with phenyl or $NR_{10}C(=NR_{10})NR_{10}R_{11}$, $C_{1-3}$alkoxy, halogen, CN, oxo, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 5 or 6 membered aromatic or nonaromatic carbocyclic ring optionally substituted by $C_{1-3}$alkyl or OH, or optionally spiro-fused to a 1,3 dioxolane group or 1,3 dithiolane group, each 1,3 dioxolane group or 1,3 dithiolane group optionally substituted by $C_{1-3}$alkyl, $C_{1-3}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, benzyl and phenyl; wherein said alkyl, cycloalkyl, benzyl or phenyl are optionally substituted with OH, $C_{1-3}$alkoxy, $C_{1-3}$acyloxy, CN, $NO_2$, $CO_2R_{12}$, $NR_{13}R_{14}$, $O(CH_2)_{2-4}NR_{13}R_{14}$ or phenyl or $R_{10}$ and $R_{11}$ together form morpholino, pyrrolidinyl, piperazinyl or piperidinyl each optionally substituted by $C_{1-3}$ alkyl, $C_{1-3}$alkoxy, OH, $-(CH_2)_nNR_{13}R_{14}$, $CONR_{13}R_{14}$ or $NR_{13}COR_{14}$;

$R_{12}$ is H, $C_{1-6}$alkyl or $C_{5-7}$cycloalkyl, each optionally substituted with phenyl, OH, $C_{1-3}$alkoxy or $NR_{13}R_{14}$; or $R_{12}$ is phenyl or heterocycle, each optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$; and $R_{15}$ is H.

In another embodiment, there are provided compounds of the formula (I) described immediately above, wherein:

$Ar_1$ is phenyl, or pyridyl, wherein each is optionally substituted by one or more $R_1$, $R_2$ and $R_3$ as defined below;

X is NH or $N-CH_3$;

Y is NH and $R_a$ is H, hydroxy$C_{1-2}$alkyl, 2-hydroxyethylaminomethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl;

$R_1$ and $R_2$ are the same or different and selected from: H, halogen, $C_{1-3}$ alkyl, wherein the $C_{1-3}$ alkyl are optionally partially or fully halogenated, $NO_2$, $NR_{13}R_{14}$;

$R_3$ is H, halogen, methoxy or methyl;

$R_4$ and $R_5$ together complete a fused ring of formula B;

$R_8$ is H, $C_{1-3}$alkyl optionally substituted with OH; or $R_8$ is $(CH_2)_{2-3}NR_{10}R_{11}$ or $CO_2R_{12}$;

$R_9$ is CN; or $R_9$ is methyl, $C_{2-3}$ alkenyl or $C_{2-3}$ alkynyl, each being optionally substituted with one or more $C_{5-7}$cycloalkylidene, $C_{5-7}$cycloalkenyl, OH, CN, $NR_{10}R_{11}$, $NR_{10}CONR_{10}R_{11}$, $NR_{10}COR_{12}$, $NR_{10}S(O)_pR_{12}$, $CONR_{10}R_{11}$, $CO_2R_{12}$, $C(R_{10})=NNR_{10}R_{11}$ or heteroaryl;

or $R_9$ is aryl or heteroaryl optionally substituted with one to three groups selected from $C_{1-3}$alkyl optionally substituted with phenyl, $C_{1-3}$alkoxy, halogen, amino or $CONH_2$;

or $R_8$ and $R_9$ together form a cyclopentene ring spiro-fused to a 1,3 dioxolane group, said 1,3 dioxolane group being optionally substituted by $C_{1-3}$alkyl, $C_{1-3}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-3}$alkyl branched or unbranched, $C_{5-7}$cycloalkyl or phenyl, wherein said alkyl, cycloalkyl or phenyl are optionally substituted with OH, $C_{1-3}$alkoxy, $C_{1-3}$acyloxy, $NO_2$, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy, OH, $(CH_2)_nNR_{13}R_{14}$, $CONR_{13}R_{14}$ or $NR_{13}COR_{14}$;

$R_{12}$ is H, $C_{1-3}$alkyl or $C_{5-7}$cycloalkyl, each optionally substituted with phenyl, OH, $C_{1-3}$alkoxy or $NR_{13}R_{14}$; or $R_{12}$ is phenyl or is a saturated, 4- to 6-membered nitrogen-containing heterocycle, each optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-3}$alkyl optionally substituted with $C_{1-3}$alkoxy or OH;

or $R_{13}$ and $R_{14}$ together form a chain completing a ring, said chain is $(CH_2)_{4-5}$ or $(CH_2)_2O(CH_2)_2$.

In yet another embodiment, there are provided compounds of the formula (I) described immediately above, wherein:

$Ar_1$ is phenyl;

$R_a$ is H or hydroxymethyl;

$R_1$ and $R_2$ are the same or different and selected from: halogen, methyl optionally partially or fully halogenated, $NO_2$ and $NH_2$;

$R_3$ is H, chloro, fluoro, bromo or methoxy;

$R_{10}$ and $R_{11}$ may be the same or different and are each independently selected from H, OH, methoxy, $C_{1-3}$alkyl branched or unbranched or $C_{5-7}$cycloalkyl, wherein said alkyl or cycloalkyl are optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl, $NR_{13}R_{14}$, $CONR_{13}R_{14}$ or $NR_{13}COR_{14}$; and $R_{12}$ is $C_{1-3}$alkyl optionally substituted with morpholino; or $R_{12}$ is phenyl or is azetidinyl, pyrrolidinyl or piperidinyl, each optionally substituted with one to three groups selected from $C_{1-3}$alkyl, $C_{1-3}$alkoxy and halogen.

In another subgeneric aspect, the invention provides novel compounds of the formula I:

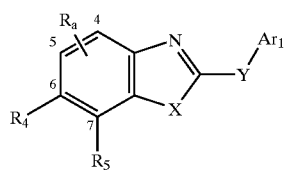

(I)

wherein:
Ar$_1$ is an aromatic or nonaromatic carbocycle, heteroaryl or heterocycle; wherein said carbocycle, heteroaryl or heterocyle is optionally substituted by one or more R$_1$, R$_2$ and R$_3$;
X is NH, N—C$_{1-3}$alkyl, N-cyclopropyl, S or O;
Y is NR$_{15}$, S or O;
R$_a$ is H, C$_{1-10}$alkyl, C$_{2-10}$alkenyl or C$_{2-10}$alkynyl, each of which may be branched or cyclic; or R$_a$ is aryl or heteroaryl; wherein each R$_a$ is independently optionally substituted with one or more C$_{1-3}$alkyl, C$_{1-6}$ alkoxy, halogen, OH, oxo, NR$_{10}$R$_{11}$, aryl or heteroaryl each aryl or heteroaryl being optionally substituted with one or more groups selected from halogen, OH, C$_{1-3}$alkyl, C$_{1-3}$alkoxy, hydroxyC$_{1-3}$alkyl and (CH$_2$)$_m$NR$_{10}$R$_{11}$; and wherein R$_a$ is attached at the 4- or 5- position;
R$_1$ and R$_2$ are the same or different and selected from H, halogen, CN, NO$_2$, C$_{1-10}$ branched or unbranched saturated or unsaturated alkyl, C$_{1-10}$ branched or unbranched alkoxy, C$_{1-10}$ branched or unbranched acyl, C$_{1-10}$ branched or unbranched acyloxy, C$_{1-10}$ branched or unbranched alkylthio, aminosulfonyl, di-(C$_{1-3}$) alkylaminosulfonyl, NR$_{10}$R$_{11}$, aryl, aroyl, aryloxy, arylsulfonyl, heteroaryl and heteroaryloxy; wherein the above mentioned R$_1$ and R$_2$ are optionally partially or fully halogenated or optionally substituted with one to three groups independently selected from oxo, OH, NR$_{10}$R$_{11}$, C$_{1-6}$ branched or unbranched alkyl, C$_{3-7}$cycloalkyl, phenyl, naphthyl, heteroaryl, aminocarbonyl and mono- or di(C$_{1-3}$)alkylaminocarbonyl;
R$_3$ is H, halogen, OH, (CH$_2$)$_n$NR$_{10}$R$_{11}$, (CH$_2$)$_n$CO$_2$R$_{12}$; C$_{1-3}$alkyl optionall substituted with OH, C$_{1-3}$ alkoxy optionally halogenated or C$_{1-3}$ alkylthio;
R$_4$ and R$_5$ together with the atoms to which they are attached complete a fused ring system of the formulas A or B:

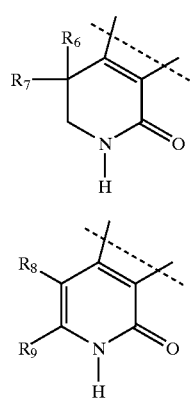

R$_6$ is C$_{1-3}$alkyl or H;
R$_7$ is C$_{1-6}$alkyl branched or unbranched or H;
R$_8$ is H, C$_{1-6}$ alkyl branched or unbranched, saturated or unsaturated, optionally substituted with phenyl, OH or C$_{1-3}$alkoxy; or R$_8$ is (CH$_2$)$_m$NR$_{10}$R$_{11}$, (CH$_2$)$_m$NR$_{10}$COR$_{12}$, (CH$_2$)$_n$CO$_2$R$_{12}$, (CH$_2$)$_n$CONR$_{10}$R$_{11}$; or R$_8$ is phenyl or heteroaryl, each being optionally substituted with C$_{1-3}$alkyl, C$_{1-3}$alkoxy, OH, —SO$_3$H or halogen;
R$_9$ is H; or R$_9$ is C$_{1-10}$alkyl branched or unbranched, C$_{3-10}$ cycloalkyl, C$_{2-6}$ alkenyl, C$_{2-6}$ alkynyl each being optionally substituted with one or more halogen, OH, oxo, CN, C$_{1-3}$alkoxy, NR$_{10}$R$_{11}$, NR$_{10}$COR$_{12}$, SR$_{12}$, CONR$_{10}$R$_{11}$, CO$_2$R$_{12}$, aryloxy, arylthio, aryl or heteroaryl; wherein each aryloxy, arylthio, aryl or heteroaryl is optionally substituted with C$_{1-3}$alkyl, C$_{1-3}$alkoxy, halogen, (CH$_2$)$_n$NR$_{10}$R$_{11}$ or O(CH$_2$)$_{2-4}$NR$_{10}$R$_{11}$;
or R$_9$ is aryl or heteroaryl, wherein each aryl or heteroaryl is optionally substituted with one to three groups selected from C$_{1-3}$alkyl optionally substituted with phenyl, C$_{1-3}$alkoxy, halogen, (CH$_2$)$_n$NR$_{10}$R$_{11}$, (CH$_2$)$_n$CO$_2$R$_{12}$; (CH$_2$)$_n$CONR$_{10}$R$_{11}$ and O(CH$_2$)$_{2-4}$NR$_{10}$R$_{11}$;
or R$_8$ and R$_9$ together form a saturated or unsaturated 6 membered aromatic or nonaromatic carbocyclic ring optionally substituted by one or two OH, oxo or (CH$_2$)$_n$NR$_{10}$R$_{11}$ ;
R$_{10}$ and R$_{11}$ may be the same or different and are each independently selected from H, OH, C$_{1-3}$alkoxy, C$_{1-6}$alkyl branched or unbranched, C$_{3-8}$cycloalkyl, aryl, arylC$_{1-3}$alkyl and heteroaryl; wherein said alkyl, cycloalkyl, aryl, arylC$_{1-3}$alkyl or heteroaryl are optionally substituted with OH, C$_{1-3}$alkoxy, C$_{1-3}$acyloxy, CO$_2$R$_{12}$, NR$_{13}$R$_{14}$, O(CH$_2$)$_{2-4}$NR$_{13}$R$_{14}$, aryl or heteroaryl;
or R$_{10}$ and R$_{11}$ together form a 3-7 member alkylene chain completing a ring about the N atom to which they are attached; wherein said alkylene chain is optionally interrupted by O, S(O)p, and NR$_{13}$; and wherein said ring is optionally substituted by C$_{1-3}$ alkyl, C$_{1-3}$alkoxy, OH or —(CH$_2$)$_n$NR$_{13}$R$_{14}$;
R$_{12}$ is H, C$_{1-6}$alkyl or C$_{3-8}$cycloalkyl wherein each alkyl or cycloalkyl is optionally substituted with phenyl, OH, C$_{1-3}$alkoxy or NR$_{13}$R$_{14}$; or R$_{12}$ is phenyl, optionally substituted with one to three groups selected from C$_{1-3}$alkyl, C$_{1-3}$alkoxy, halogen, (CH$_2$)$_n$NR$_{10}$R$_{11}$, (CH$_2$)$_n$CONR$_{10}$R$_{11}$ and O(CH$_2$)$_{2-4}$NR$_{10}$R$_{11}$;
R$_{13}$ and R$_{14}$ are each independently selected from H and C$_{1-6}$ alkyl optionally substituted with C$_{1-3}$alkoxy, OH or phenyl;
or R$_{13}$ and R$_{14}$ together form a chain completing a ring, said chain is (CH$_2$)$_{4-5}$ or (CH$_2$)$_2$O(CH$_2$)$_2$;
R$_{15}$ is H or C$_{1-3}$ alkyl;
m is 1–4, n is 0–3 and p is 0–2; and
the pharmaceutically acceptable acid or salt derivatives thereof.

In one embodiment of the invention, there are provided compounds of the formula (I) as described immediately above, and wherein:
Ar$_1$ is
a) a cycloalkyl group selected from cyclopropyl, cyclobutyl, cyclopentanyl, cyclohexanyl, cycloheptanyl;
b) a cycloalkenyl group selected from cyclopentenyl, cyclohexenyl, cycloheptenyl;
c) phenyl, naphthyl, indanyl, indenyl, dihydronaphthyl, tetrahydronaphthyl, fluorenyl;
d) heteroaryl selected from pyridinyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein each of the above $Ar_1$ are optionally substituted by one or more $R_1$, $R_2$ and $R_3$ as hereinabove defined;

$R_a$ is H, $C_{1-6}$ alkyl, $C_{2-5}$ alkenyl, $C_{2-5}$ alkynyl, phenyl or heteroaryl selected from: pyridinyl, pyridazinyl, pyrimidinyl, pyrazinyl, oxazolyl, pyrazolyl, imidazolyl, furyl, thiazolyl and thienyl; each $R_a$ being optionally substituted with one or more phenyl, halogen, $C_{1-3}$alkyl, $C_{1-3}$ alkoxy, OH, oxo, or $NR_{10}R_{11}$; wherein $R_a$ is at the 4-position;

$R_3$ is H, halogen, methyl, methoxy, hydroxymethyl or OH;

$R_8$ is H, $C_{1-3}$alkyl branched or unbranched, saturated or unsaturated, optionally substituted with OH; or $R_8$ is $(CH_2)_{2-3}NR_{10}R_{11}$, $(CH_2)_nCO_2R_{12}$ or $(CH_2)_nCONR_{10}R_{11}$;

$R_9$ is $C_{1-3}$alkyl branched or unbranched, $C_{2-4}$ alkenyl, $C_{2-4}$alkynyl each being optionally substituted with one or more OH, CN, $NR_{10}R_{11}$, $CONR_{10}R_{11}$, $CO_2R_{12}$, aryl or heteroaryl; wherein each aryl or heteroaryl is optionally substituted with $C_{1-3}$alkyl, $C_{1-3}$alkoxy, halogen, $(CH_2)_n NR_{10}R_{11}$ or $O(CH_2)_{2-4}NR_{10}R_{11}$;

or $R_9$ is aryl or heteroaryl optionally substituted with one to three groups selected from $C_{1-3}$alkyl optionally substituted with phenyl, $C_{1-3}$alkoxy, halogen, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 6 membered aromatic or nonaromatic carbocyclic ring optionally substituted by OH;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, benzyl and phenyl;

wherein said alkyl, cycloalkyl, benzyl or phenyl are optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy, OH or —$(CH_2)_nNR_{13}R_{14}$;

$R_{12}$ is H or $C_{1-6}$alkyl optionally substituted with phenyl, OH, $C_{1-3}$alkoxy or $NR_{13}R_{14}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$; and $R_{15}$ is H.

In another embodiment of the invention, there are provided compounds of the formula (I) as described immediately above, and wherein:

$Ar_1$ is phenyl, or pyridyl;

X is NH or N—$CH_3$;

Y is NH and $R_a$ is H, hydroxy$C_{1-2}$alkyl, 2-hydroxyethylaminomethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl;

$R_1$ and $R_2$ are the same or different and selected from: halogen, $C_{1-3}$ alkyl, wherein the $C_{1-3}$ alkyl are optionally partially or fully halogenated, $NO_2$, $NR_{13}R_{14}$;

$R_3$ is H, halogen, methoxy or methyl;

$R_4$ and $R_5$ together complete a fused ring of formula B;

$R_8$ is H, $C_{1-3}$alkyl optionally substituted with OH; or $R_8$ is $(CH_2)_{2-3}NR_{10}R_{11}$ or $CO_2R_{12}$;

$R_9$ is methyl or $C_{2-3}$ alkenyl each being optionally substituted with one or more OH, CN, $NR_{10}R_{11}$, $CONR_{10}R_{11}$ or $CO_2R_{12}$;

or $R_9$ is heteroaryl optionally substituted with one to three groups selected from $C_{1-3}$alkyl optionally substituted with phenyl, $C_{1-3}$alkoxy, halogen or amino;

is $R_{10}$ and $R_{11}$ may be the same or different and are each independently selected from H, OH, $C_{1-3}$alkoxy, $C_{1-3}$alkyl branched or unbranched, optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy or OH;

$R_{12}$ is H or $C_{1-3}$alkyl optionally substituted with phenyl, OH, $C_{1-3}$alkoxy or $NR_{13}R_{14}$;

$R_{13}$ and $R_{14}$ are each independently selected from H and $C_{1-3}$alkyl optionally substituted with $C_{1-3}$alkoxy or OH;

or $R_{13}$ and $R_{14}$ together form a chain completing a ring, said chain is $(CH_2)_{4-5}$ or $(CH_2)_2O(CH_2)_2$.

In yet another embodiment of the invention there are provided compounds of the formula (I) as described immediately above, and wherein:

$Ar_1$ is phenyl;

$R_a$ is H or hydroxymethyl;

$R_1$ and $R_2$ are the same or different and selected from: halogen, methyl optionally partially or fully halogenated, $NO_2$ and $NH_2$;

$R_3$ is H, chloro, fluoro, bromo or methoxy;

$R_{10}$ and $R_{11}$ may be the same or different and are each independently selected from H, OH, methoxy, $C_{1-3}$alkyl branched or unbranched, optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl; and $R_{12}$ is $C_{1-3}$alkyl optionally substituted with morpholino.

In still another embodiment of the invention there are provided compounds of the formula (Ia):

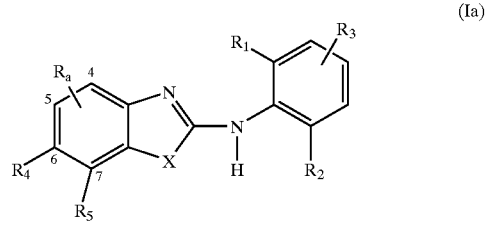

(Ia)

wherein:

X is NH, N—$C_{1-3}$alkyl, N-cyclopropyl, S or O;

$R_a$ is H, $C_{1-10}$alkyl, $C_{2-10}$alkenyl or $C_{2-10}$alkynyl, each of which may be branched or cyclic; or $R_a$ is aryl or heteroaryl;

wherein each $R_a$ is independently optionally substituted with one or more $C_{1-6}$alkyl, $C_{1-6}$ alkoxy, halogen, OH, oxo, $NR_{10}R_{11}$, aryl or heteroaryl each aryl or heteroaryl being optionally substituted with one or more groups selected from halogen, OH, $C_{1-3}$alkyl, $C_{1-3}$alkoxy, hydroxy$C_{1-3}$alkyl and $(CH_2)_mNR_{10}R_{11}$; and wherein $R_a$ is attached at the 4- or 5-position;

$R_1$ and $R_2$ are the same or different and selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-$(C_{1-3})$alkylaminosulfonyl, $NR_{10}R_{11}$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from oxo, OH, $NR_{10}R_{11}$, $C_{1-6}$ branched or unbranched alkyl, $C_{3-7}$cycloalkyl, phenyl, naphthyl, heteroaryl, aminocarbonyl and mono- or di($C_{1-3}$)alkylaminocarbonyl;

$R_3$ is H, halogen, OH, $(CH_2)_nNR_{10}R_{11}$, $CONR_{10}R_{11}$, $(CH_2)_nCO_2R_{12}$; $C_{1-3}$alkyl optionally substituted with OH, $C_{1-3}$ alkoxy optionally halogenated or $C_{1-3}$ alkylthio;

$R_4$ and $R_5$ together with the atoms to which they are attached complete a fused ring system of the formulas A or B:

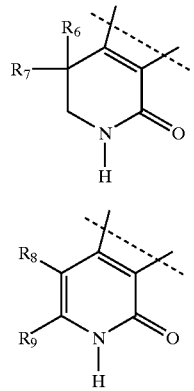

$R_6$ is $C_{1-3}$alkyl or H;

$R_7$ is $C_{1-6}$alkyl branched or unbranched or H;

$R_8$ is H, $C_{1-6}$alkyl branched or unbranched, saturated or unsaturated, optionally substituted with phenyl, OH or $C_{1-3}$alkoxy; or $R_8$ is $(CH_2)_mNR_{10}R_{11}$, $(CH_2)_mNR_{10}COR_{12}$, $(CH_2)_nCO_2R_{12}$, $(CH_2)_nCONR_{10}R_{11}$ or $R_8$ is phenyl or heteroaryl, each being optionally substituted with $C_{1-3}$alkyl, $C_{1-3}$alkoxy, OH, —$SO_3H$ or halogen;

$R_9$ is H, CN or $CONR_{10}R_{11}$; or $R_9$ is $C_{1-10}$alkyl branched or unbranched, $C_{3-10}$cycloalkyl, $C_{5-7}$cycloalkenyl, $C_{2-6}$ alkenyl, $C_{2-6}$ alkynyl each being optionally substituted with one or more $C_{3-10}$cycloalkyl, $C_{3-10}$cycloalkylidene, $C_{5-7}$cycloalkenyl, halogen, OH, oxo, CN, $C_{1-3}$alkoxy, $C_{1-3}$acyloxy, $NR_{10}R_{11}$, $NR_{10}CONR_{10}R_{11}$, $NR_{10}C(=NR_{10})NR_{10}R_{11}$, $NR_{10}COR_{12}$, $NR_{10}S(O)_pR_{12}$, $SR_{12}$, $CONR_{10}R_{11}$, $CO_2R_{12}$, $C(R_{10})=NNR_{10}R_{11}$, $C(R_{10})=NNR_{10}CONR_{10}R_{11}$, aryloxy, arylthio, aryl or heteroaryl; wherein each aryloxy, arylthio, aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl, heteroaryl, or heterocycle, wherein each aryl, heteroaryl or heterocycle is optionally substituted with one to three groups selected from $C_{1-3}$alkyl optionally substituted with phenyl or $NR_{10}C(=NR_{10})NR_{10}R_{11}$, $C_{1-3}$alkoxy, halogen, CN, oxo, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 5 or 6 membered aromatic or nonaromatic carbocyclic ring optionally substituted by one or two $C_{1-3}$alkyl, OH, oxo or $(CH_2)_nNR_{10}R_{11}$, or optionally spiro-fused to a 1,3 dioxolane group or 1,3 dithiolane group, each 1,3 dioxolane group or 1,3 dithiolane group optionally substituted by $C_{1-6}$alkyl, $C_{1-6}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, aryl$C_{1-3}$alkyl or heteroaryl are optionally substituted with OH, $C_{1-3}$alkoxy, CN, $NO_2$, $C_{1-3}$acyloxy, $CO_2R_{12}$, $NR_{13}R_{14}$, $O(CH_2)_{2-4}NR_{13}R_{14}$, aryl or heteroaryl;

or $R_{10}$ and $R_{11}$ together form a 3-7 member alkylene chain completing a ring about the N atom to which they are attached; wherein said alkylene chain is optionally interrupted by O, $S(O)_p$, and $NR_{13}$; and wherein said ring is optionally substituted by $C_{1-3}$ alkyl, $C_{1-3}$alkoxy, OH, —$(CH_2)_nNR_{13}R_{14}$, $CONR_{13}R_{14}$ or $NR_{13}COR_{14}$;

$R_{12}$ is H, $C_{1-6}$alkyl or $C_{3-8}$cycloalkyl wherein each alkyl or cycloalkyl is optionally substituted with phenyl, OH, $C_{1-3}$alkoxy or $NR_{13}R_{14}$; or $R_{12}$ is phenyl or heterocycle, optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$;

m is 1–4, n is 0–3 and p is 0–2; and the pharmaceutically acceptable acid or salt derivatives thereof.

In another embodiment of the invention, there are provided compounds of the formula (Ia) as described above, wherein:

X is NH or N—$CH_3$;

$R_a$ is H, hydroxy$C_{1-2}$alkyl, 2-hydroxyethylaminomethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl; and wherein $R_a$ is attached at the 4- position;

$R_1$ and $R_2$ are the same or different and selected from: H, halogen, $C_{1-3}$ alkyl, wherein the $C_{1-3}$ alkyl is optionally partially or fully halogenated, $NO_2$, $NR_{13}R_{14}$;

$R_3$ is H, halogen, methoxy or methyl;

$R_4$ and $R_5$ together complete a fused ring of formula B;

$R_8$ is H, $C_{1-3}$alkyl optionally substituted with OH; or $R_8$ is $(CH_2)_{2-3}NR_{10}R_{11}$ or $CO_2R_{12}$;

$R_9$ is CN; or $R_9$ is methyl, $C_{2-3}$ alkenyl or $C_{2-3}$ alkynyl, each being optionally substituted with one or more $C_{5-7}$ cycloalkylidene, $C_{5-7}$cycloalkenyl, OH, CN, $NR_{10}R_{11}$, $NR_{10}CONR_{10}R_{11}$, $NR_{10}COR_{12}$, $NR_{10}S(O)_pR_{12}$, $CONR_{10}R_{11}$, $CO_2R_{12}$, $C(R_{10})=NNR_{10}R_{11}$ or heteroaryl;

or $R_9$ is aryl or heteroaryl optionally substituted with one to three groups selected from $C_{1-3}$alkyl optionally substituted with phenyl, $C_{1-3}$alkoxy, halogen, amino or $CONH_2$;

or $R_8$ and $R_9$ together form a cyclopentene ring spiro-fused to a 1,3 dioxolane group, said 1,3 dioxolane group being optionally substituted by $C_{1-3}$alkyl, $C_{1-3}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-3}$alkyl branched or unbranched, $C_{5-7}$cycloalkyl or phenyl, wherein said alkyl, cycloalkyl or phenyl are optionally substituted with OH, $C_{1-3}$alkoxy, $C_{1-3}$acyloxy, $NO_2$, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy, OH, $(CH_2)_n NR_{13}R_{14}$, $CONR_{13}R_{14}$ or $NR_{13}COR_{14}$;

$R_{12}$ is H, $C_{1-3}$alkyl or $C_{5-7}$cycloalkyl, each optionally substituted with phenyl, OH, $C_{1-3}$alkoxy or $NR_{13}R_{14}$; or $R_{12}$ is phenyl or is a saturated, 4- to 6-membered nitrogen-containing heterocycle, each optionally substituted with one to three groups selected from $C_{1-3}$alkyl, $C_{1-3}$alkoxy, halogen, $(CH_2)_m NR_{10}R_{11}$, $(CH_2)_n CONR_{10}R_{11}$ and $O(CH_2)_{2-4}NR_{10}R_{11}$;

$R_{13}$ and $R_{14}$ are each independently selected from H and $C_{1-3}$alkyl optionally substituted with $C_{1-3}$alkoxy or OH;

or $R_{13}$ and $R_{14}$ together form a chain completing a ring, said chain is $(CH_2)_{4-5}$ or $(CH_2)_2 O(CH_2)_2$.

In yet another embodiment of the present invention, there are provided compounds of the formula (Ia) described immediately above, wherein:

$R_a$ is H or hydroxymethyl;

$R_1$ and $R_2$ are the same or different and selected from: halogen, methyl optionally partially or fully halogenated, $NO_2$ and $NH_2$;

$R_3$ is H, chloro, fluoro, bromo or methoxy;

$R_{10}$ and $R_{11}$ may be the same or different and are each independently selected from H, OH, methoxy, $C_{1-3}$alkyl branched or unbranched or $C_{5-7}$cycloalkyl, wherein said alkyl or cycloalkyl are optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl, $NR_{13}R_{14}$, $CONR_{13}R_{14}$ or $NR_{13}COR_{14}$; and $R_{12}$ is $C_{1-3}$alkyl optionally substituted with morpholino; or $R_{12}$ is phenyl or is azetidinyl, pyrrolidinyl or piperidinyl, each optionally substituted with one to three groups selected from $C_{1-3}$alkyl, $C_{1-3}$alkoxy and halogen.

In still another subgeneric embodiment of the invention there are provided compounds of the formula (Ia):

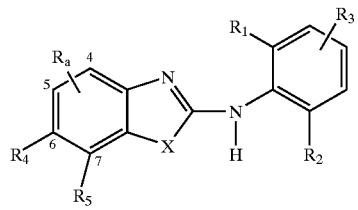

(Ia)

wherein:

X is NH, N—$C_{1-3}$alkyl, N-cyclopropyl, S or O;

$R_a$ is H, $C_{1-10}$alkyl, $C_{2-10}$alkenyl or $C_{2-10}$alkynyl, each of which may be branched or cyclic; or $R_a$ is aryl or heteroaryl;

wherein each $R_a$ is independently optionally substituted with one or more $C_{1-6}$ alkoxy, halogen, OH, oxo, $NR_{10}R_{11}$, aryl or heteroaryl each aryl or heteroaryl being optionally substituted with one or more groups selected from halogen, OH, $C_{1-3}$alkyl, $C_{1-3}$alkoxy, hydroxy$C_{1-3}$alkyl and $(CH_2)_m NR_{10}R_{11}$; and wherein $R_a$ is attached at the 4- or 5- position;

$R_1$ and $R_2$ are the same or different and selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-($C_{1-3}$)alkylaminosulfonyl, $NR_{10}R_{11}$, aryl, aroyl, aryloxy, arylsulfonyl, heteroaryl and heteroaryloxy; wherein the above mentioned $R_1$ and $R_2$ are optionally partially or fully halogenated or optionally substituted with one to three groups independently selected from oxo, OH, $NR_{10}R_{11}$, $C_{1-6}$ branched or unbranched alkyl, $C_{3-7}$cycloalkyl, phenyl, naphthyl, heteroaryl, aminocarbonyl and mono- or di($C_{1-3}$)alkylaminocarbonyl;

$R_3$ is H, halogen, OH, $(CH_2)_n NR_{10}R_{11}$, $(CH_2)_n CO_2R_{12}$; $C_{1-3}$alkyl optionally substituted with OH, $C_{1-3}$ alkoxy optionally halogenated or $C_{1-3}$ alkylthio;

$R_4$ and $R_5$ together with the atoms to which they are attached complete a fused ring system of the formulas A or B:

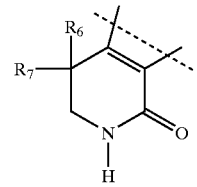

A

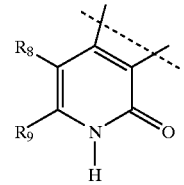

B $R_6$ is $C_{1-3}$alkyl or H;

$R_7$ is $C_{1-6}$alkyl branched or unbranched or H;

$R_8$ is H, $C_{1-6}$alkyl branched or unbranched, saturated or unsaturated, optionally substituted with phenyl, OH or $C_{1-3}$alkoxy; or $R_8$ is $(CH_2)_m NR_{10}R_{11}$, $(CH_2)_m NR_{10}COR_{12}$, $(CH_2)_n CO_2R_{12}$, $(CH_2)_n CONR_{10}R_{11}$ or $R_8$ is phenyl or heteroaryl, each being optionally substituted with $C_{1-3}$alkyl, $C_{1-3}$alkoxy, OH, —$SO_3H$ or halogen;

$R_9$ is H; or $R_9$ is $C_{1-10}$alkyl branched or unbranched, $C_{3-10}$cycloalkyl, $C_{2-6}$ alkenyl, $C_{2-6}$alkynyl each being optionally substituted with one or more halogen, OH, oxo, CN, $C_{1-3}$alkoxy, $NR_{10}R_{11}$, $NR_{10}COR_{12}$, $SR_{12}$, $CONR_{10}R_{11}$, $CO_2R_{12}$, aryloxy, arylthio, aryl or heteroaryl; wherein each aryloxy, arylthio, aryl or heteroaryl is optionally substituted with $C_{1-3}$alkyl, $C_{1-3}$alkoxy, halogen, $(CH_2)_n NR_{10}R_{11}$ or $O(CH_2)_{2-4}NR_{10}R_{11}$;

or $R_9$ is aryl or heteroaryl, wherein each aryl or heteroaryl is optionally substituted with one to three groups selected from $C_{1-3}$alkyl optionally substituted with phenyl, $C_{1-3}$alkoxy, halogen, $(CH_2)_n NR_{10}R_{11}$, $(CH_2)_n CO_2R_{12}$; $(CH_2)_n CONR_{10}R_{11}$ and $O(CH_2)_{2-4}NR_{10}R_{11}$;

or $R_8$ and $R_9$ together form a saturated or unsaturated 6 membered aromatic or nonaromatic carbocyclic ring optionally substituted by one or two OH, oxo or $(CH_2)_n NR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, arylC$_{1-3}$alkyl or heteroaryl are optionally substituted with OH, C$_{1-3}$alkoxy, C$_{1-3}$acyloxy, CO$_2$R$_{12}$, NR$_{13}$R$_{14}$, O(CH$_2$)$_{2-4}$NR$_{13}$R$_{14}$, aryl or heteroaryl;

or R$_{10}$ and R$_{11}$ together form a 3–7 member alkylene chain completing a ring about the N atom to which they are attached; wherein said alkylene chain is optionally interrupted by O, S(O)$_p$ and NR$_{13}$; and wherein said ring is optionally substituted by C$_{1-3}$ alkyl, C$_{1-3}$alkoxy, OH or —(CH$_2$)$_n$NR$_{13}$R$_{14}$;

R$_{12}$ is H, C$_{1-6}$alkyl or C$_{3-8}$cycloalkyl wherein each alkyl or cycloalkyl is optionally substituted with phenyl, OH, C$_{1-3}$alkoxy or NR$_{13}$R$_{14}$; or R$_{12}$ is phenyl, optionally substituted with one to three groups selected from C$_{1-3}$alkyl, C$_{1-3}$alkoxy, halogen, (CH$_2$)$_m$NR$_{10}$R$_{11}$, (CH$_2$)$_n$CONR$_{10}$R$_{11}$ and O(CH$_2$)$_{2-4}$NR$_{10}$R$_{11}$;

R$_{13}$ and R$_{14}$ are each independently selected from H and C$_{1-6}$ alkyl optionally substituted with C$_{1-3}$alkoxy, OH or phenyl;

or R$_{13}$ and R$_{14}$ together form a chain completing a ring, said chain is (CH$_2$)$_{4-5}$ or (CH$_2$)$_2$O(CH$_2$)$_2$;

m is 1–4, n is 0–3 and p is 0–2; and the pharmaceutically acceptable acid or salt derivatives thereof.

In another embodiment of the invention there are provided compounds of the formula (Ia) as described immediately above, and wherein:

X is NH or N—CH$_3$;

R$_a$ is H, hydroxyC$_{1-2}$alkyl, 2-hydroxyethylaminomethyl, methoxybenzylaminomethyl, pyridinyl optionally halogenated, phenyl, 3-hydroxy-2-oxo-propyl, vinyl or C$_{3-5}$alkynyl substituted by C$_{1-3}$alkoxy or phenyl; and wherein R$_a$ is attached at the 4- position;

R$_1$ and R$_2$ are the same or different and selected from: halogen, C$_{1-3}$ alkyl, wherein the C$_{1-3}$ alkyl is optionally partially or fully halogenated, NO$_2$, NR$_{13}$R$_{14}$;

R$_3$ is H, halogen, methoxy or methyl;

R$_4$ and R$_5$ together complete a fused ring of formula B;

R$_8$ is H, C$_{1-3}$alkyl optionally substituted with OH; or R$_8$ is (CH$_2$)$_{2-3}$NR$_{10}$R$_{11}$ or CO$_2$R$_{12}$;

R$_9$ is methyl or C$_{2-4}$ alkenyl each being optionally substituted with one or more OH, CN, NR$_{10}$R$_{11}$, CONR$_{10}$R$_{11}$ or CO$_2$R$_{12}$;

or R$_9$ is heteroaryl optionally substituted with one to three groups selected from C$_{1-3}$alkyl optionally substituted with phenyl, C$_{1-3}$alkoxy, halogen or (CH$_2$)$_n$NR$_{10}$R$_{11}$;

R$_{10}$ and R$_{11}$ may be the same or different and are each independently selected from H, OH, C$_{1-3}$alkoxy, C$_{1-3}$alkyl branched or unbranched, optionally substituted with OH, C$_{1-3}$alkoxy, C$_{1-3}$acyloxy, CO$_2$R$_{12}$, NR$_{13}$R$_{14}$, O(CH$_2$)$_{2-4}$NR$_{13}$R$_{14}$ or phenyl;

or R$_{10}$ and R$_{11}$ together form morpholino, pyrrolidinyl, piperazinyl or piperidinyl each optionally substituted by C$_{1-3}$ alkyl, C$_{1-3}$alkoxy or OH;

is R$_{12}$ is H or C$_{1-3}$alkyl optionally substituted with phenyl, OH, C$_{1-3}$alkoxy or NR$_{13}$R$_{14}$;

R$_{13}$ and R$_{14}$ are each independently selected from H and C$_{1-3}$alkyl optionally substituted with C$_{1-3}$alkoxy or OH;

or R$_{13}$ and R$_{14}$ together form a chain completing a ring, said chain is (CH$_2$)$_{4-5}$ or (CH$_2$)$_2$O(CH$_2$)$_2$.

In still a further embodiment of the invention there are provided compounds of the formula (Ia) as described immediately above, and wherein:

R$_a$ is H or hydroxymethyl;

R$_1$ and R$_2$ are the same or different and selected from: halogen, methyl optionally partially or fully halogenated, NO$_2$ and NH$_2$;

R$_3$ is H, chloro, fluoro, bromo or methoxy;

R$_{10}$ and R$_{11}$ may be the same or different and are each independently selected from H, OH, methoxy, Cl$_3$alkyl branched or unbranched, optionally substituted with OH, NR$_{13}$R$_{14}$ or phenyl;

or R$_{10}$ and R$_{11}$ together form morpholino, pyrrolidinyl, piperazinyl or piperidinyl each optionally substituted by C$_{1-2}$ alkyl; and R$_{12}$ is C$_{1-3}$alkyl optionally substituted with morpholino.

In another aspect of the invention, there are provided intermediate compounds of the formula(III) useful in the synthetic schemes and examples set forth below. In yet another aspect of the invention are particular intermediate compounds of the formula (III), (representative examples shown Table 1 below) which possess physiological activity.

In their broadest generic aspect, intermediate compounds described above are represented by the formula (III):

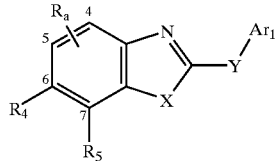

(III)

wherein:

Ar$_1$ is an aromatic or nonaromatic carbocycle, heteroaryl or heterocycle; wherein said carbocycle, heteroaryl or heterocycle is optionally substituted by one or more R$_1$, R$_2$ and R$_3$;

X is NH, N—C$_{1-3}$alkyl, N,cyclopropyl, S or O;

Y is NR$_{15}$, S or O;

R$_a$ is H, C$_{1-10}$alkyl, C$_{2-10}$alkenyl or C$_{2-10}$alkynyl, each of which may be branched or cyclic; or R$_a$ is aryl or heteroaryl;

wherein each R$_a$ is independently optionally substituted with one or more C$_{1-3}$alkyl, C$_{1-6}$ alkoxy, halogen, OH, oxo, NR$_{10}$R$_{11}$, aryl or heteroaryl each aryl or heteroaryl being optionally substituted with one or more groups selected from halogen, OH, C$_{1-3}$alkyl, C$_{1-3}$alkoxy, hydroxyC$_{1-3}$alkyl and (CH$_2$)$_m$NR$_{10}$R$_{11}$; and wherein R$_a$ is attached at the 4- or 5-position;

R$_1$ and R$_2$ are the same or different and selected from H, halogen, CN, NO$_2$, C$_{1-10}$ branched or unbranched saturated or unsaturated alkyl, C$_{1-10}$ branched or unbranched alkoxy, C$_{1-10}$ branched or unbranched acyl, C$_{1-10}$ branched or unbranched acyloxy, C$_{1-10}$ branched or unbranched alkylthio, aminosulfonyl, di-(C$_{1-3}$)alkylaminosulfonyl, NR$_{10}$R$_{11}$, aryl, aroyl, aryloxy, arylsulfonyl, heteroaryl and heteroaryloxy; wherein the abovementioned R$_1$ and R$_2$ are optionally partially or fully halogenated or optionally substituted with one to three groups independently selected from oxo, OH, NR$_{10}$R$_{11}$, C$_{1-6}$ branched or unbranched alkyl, C$_{3-7}$cycloalkyl, phenyl, naphthyl, heteroaryl, aminocarbonyl and mono- or di(C$_{1-3}$)alkylaminocarbonyl;

R$_3$ is H, halogen, OH, (CH$_2$)$_n$NR$_{10}$R$_{11}$, (CH$_2$)$_n$CO$_2$R$_{12}$; C$_{1-3}$alkyl optionally substituted with OH, C$_{1-3}$ alkoxy optionally halogenated or C$_{1-3}$ alkylthio;

R$_4$ and R$_5$ together with the atoms to which they are attached complete a fused ring system of the formula C:

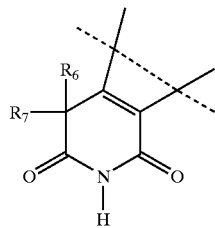

$R_6$ is $C_{1-3}$alkyl or H;
$R_7$ is $C_{1-6}$alkyl branched or unbranched or H;
$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, aryl$C_{1-3}$alkyl or heteroaryl are optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$, aryl or heteroaryl;
or $R_{10}$ and $R_{11}$ together form a 3–7 member alkylene chain completing a ring about the N atom to which they are attached; wherein said alkylene chain is optionally interrupted by O, $S(O)_p$ and $NR_{13}$; and wherein said ring is optionally substituted by $C_{1-3}$ alkyl, $C_{1-3}$alkoxy, OH or —$(CH_2)_nNR_{13}R_{14}$;
$R_{12}$ is H, $C_{1-6}$alkyl or $C_{3-8}$cycloalkyl wherein each alkyl or cycloalkyl is optionally substituted with phenyl, OH, $C_{1-3}$alkoxy or $NR_{13}R_{14}$; or $R_{12}$ is phenyl, optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;
$R_{13}$ and $R_{14}$ are each independently selected from H and $C_{1-6}$ alkyl optionally substituted with alkoxy, OH or phenyl;
or $R_{13}$ and $R_{14}$ together form a chain completing a ring, said chain is $(CH_2)_{4-5}$ or $(CH_2)_2O(CH_2)_2$; and
m is 1–4, n is 0–3 and p is 0–2.

One embodiment of the compounds of formula(III) are those wherein:
$Ar_1$ is
a) a cycloalkyl group selected from cyclopropyl, cyclobutyl, cyclopentanyl, cyclohexanyl, cycloheptanyl;
b) a cycloalkenyl group selected from cyclopentenyl, cyclohexenyl, cycloheptenyl;
c) phenyl, naphthyl; indanyl, indenyl, dihydronaphthyl, tetrahydronaphthyl, fluorenyl;
d) heteroaryl selected from pyridinyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or
e) a heterocycle selected from: pyrrolinyl, pyrrolidinyl, pyrazolinyl, pyrazolidinyl, piperidinyl, morpholinyl, thiomorpholinyl, pyranyl, thiopyranyl, piperazinyl and indolinyl;
wherein each of the above $Ar_1$ are optionally substituted by one or more $R_1$, $R_2$ and $R_3$ as hereinabove defined;
$R_a$ is H, $C_{1-6}$alkyl, $C_{2-5}$alkenyl, $C_{2-5}$alkynyl, phenyl or heteroaryl selected from: pyridinyl, pyridazinyl, pyrimidinyl, pyrazinyl, oxazolyl, pyrazolyl, imidazolyl, furyl, thiazolyl and thienyl; each $R_a$ being optionally substituted with one or more phenyl, halogen, $C_{1-3}$alkyl, $C_{1-3}$ alkoxy, OH, oxo, or $NR_{10}R_{11}$; wherein $R_a$ is at the 4- position;
$R_3$ is H, halogen, methyl, methoxy, hydroxymethyl or OH;
$R_6$ is $C_{1-3}$alkyl or H;
$R_7$ is $C_{1-6}$alkyl branched or unbranched or H;
$R_{10}$ and $R_{11}$ may be the same or different and are each independently selected from H, OH, $C_{1-3}$alkoxy, $C_{1-6}$alkyl branched or unbranched, $C_{3-8}$cycloalkyl, benzyl and phenyl;
wherein said alkyl, cycloalkyl or phenyl are optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$ or phenyl;
or $R_{10}$ and $R_{11}$ together form morpholino, pyrrolidinyl, piperazinyl or piperidinyl each optionally substituted by $C_{1-3}$ alkyl, $C_{1-3}$alkoxy, OH or —$(CH_2)_nNR_{13}R_{14}$;
$R_{12}$ is H or $C_{1-6}$alkyl optionally substituted with phenyl, OH, $C_{1-3}$alkoxy or $NR_{13}R_{14}$;
$R_{13}$ and $R_{14}$ are each independently selected from H and $C_{1-6}$ alkyl optionally substituted with $C_{1-3}$alkoxy, OH or phenyl; and
or $R_{13}$ and $R_{14}$ together form a chain completing a ring, said chain is $(CH_2)_{4-5}$ or $(CH_2)_2O(CH_2)_2$.

Another embodiment of the compounds of the formula (III) are those described immediately above, and wherein:
$Ar_1$ is phenyl, or pyridyl;
X is NH or N—$CH_3$;
Y is NH and
$R_a$ is H, hydroxy$C_{1-2}$alkyl, 2-hydroxyethylaminomethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl;
$R_1$ and $R_2$ are the same or different and selected from: halogen, $C_{1-3}$ alkyl, wherein the $C_{1-3}$ alkyl are optionally partially or fully halogenated, $NO_2$, $NR_{13}R_{14}$;
$R_3$ is H, halogen, methoxy or methyl;
$R_{10}$ and $R_{11}$ may be the same or different and are each independently selected from H, OH, $C_{1-3}$alkoxy, $C_{1-3}$alkyl branched or unbranched, optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$ or phenyl;
or $R_{10}$ and $R_{11}$ together form morpholino, pyrrolidinyl, piperazinyl or piperidinyl each optionally substituted by $C_{1-3}$ alkyl, $C_{1-3}$alkoxy or OH;
$R_{12}$ is H or $C_{1-3}$alkyl optionally substituted with phenyl, OH, $C_{1-3}$alkoxy or $NR_{13}R_{14}$;
$R_{13}$ and $R_{14}$ are each independently selected from H and $C_{1-3}$alkyl optionally substituted with $C_{1-3}$alkoxy or OH;
or $R_{13}$ and $R_{14}$ together form a chain completing a ring, said chain is $(CH_2)_{4-5}$ or $(CH_2)_2O(CH_2)_2$.

In yet another embodiment of the compounds of formula (III) are those described immediately above, and wherein:
$Ar_1$ is phenyl;
$R_a$ is H or hydroxymethyl;

$R_1$ and $R_2$ are the same or different and selected from: halogen, methyl optionally partially or fully halogenated, $NO_2$ and $NH_2$;

$R_3$ is H, chloro, fluoro, bromo or methoxy;

$R_{10}$ and $R_{11}$ may be the same or different and are each independently selected from H, OH, methoxy, $C_{1-3}$alkyl branched or unbranched, optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl; and $R_{12}$ is $C_{1-3}$alkyl optionally substituted with morpholino.

In a further embodiment of the invention, there are provided the following compounds of the fomulas (I) and (Ia):

2-(2,6-Dichlorophenylamino)-6,7-dimethyl-1,8-dihydro-imidazo[4,5-h]isoquinoline-9-one;

2-(2,6-Dichlorophenylamino)-3,5-dihydro-imidazo[4,5-i]phenanthridin-4-one;

2-(2,6-Dichlorophenylamino)-1,6,7-trimethyl-1,8-dihydro-imidazo[4,5-h]isoquinoline-9-one;

2-(2,6-Dichlorophenylamino)-7-methyl-1,8-dihydro-imidazo[4,5-h]isoquinoline-9-one;

2-(2,6-Dichlorophenylamino) -1,7-dimethyl-9-oxo-1,8-dihydro-imidazo[4,5-h]isoquinolin-6-acetic acid ethyl ester;

3 -[2-(2,6-Dichlorophenylamino)-1,6-dimethyl-9-oxo-8,9-dihydro-1H-imidazo[4,5-h]isoquinolin-7-yl]-acrylic acid methyl ester;

2-(2,6-Dichlorophenylamino)-1,7-dimethyl-6-(2-hydroxyethyl)-1,8-dihydro-imidazo[4,5-h]isoquinoline-9-one;

2-(2,6-Dichlorophenylamino)-1,7-dimethyl-9-oxo-1,8-dihydro-imidazo[4,5-h]isoquinoline-6-carboxylic acid methyl ester;

2-(2,6-Dichlorophenylamino)-1,7-dimethyl-1,8-dihydro-imidazo[4,5-h]isoquinoline-9-one;

3 -[2-(2,6-Dichlorophenylamino)-1-methyl-9-oxo-8,9-dihydro-1H-imidazo[4,5-h]isoquinolin-7-yl]-acid methyl ester;

3-[2-(2,6-Dichlorophenylamino)-1,7-dimethyl-9-oxo-1,8-dihydro-imidazo[4,5-h]isoquinolin-6-yl]propionic acid ethyl ester N-Benzyl-N-methyl-2-[(2,6-dichlorophenylamino)-1,7-dimethyl-9-oxo-1,8-dihydro-imidazo[4,5-h]isoquinolin-6-yl] acetamide;

2-(2,6-Dichlorophenylamino)-1,7-dimethyl-6-(2-morpholin-4-ylethyl)-1,8-dihydro-imidazo[4,5-h]isopuinoline-9-one;

2-(2-Chloro-6-methylphenylamino)-1,6,7-trimethyl-1,8-dihydro-imidazo[4,5-h]isoquinoline-9-one;

2-(4-Bromo-2-dichlorophenylamino)-1,6,7-trimethyl-1,8-dihydro-imidazo[4,5-h]isoquinoline-9-one;

3-[2-(2,6-Dichlorophenylamino)-1-methyl-9-oxo-8,9-dihydro-1H-imidazo[4,5-h]isoquinolin-7-yl]-N-methoxy-N-methylacrylamide;

2-(2-Chloro-6-nitrophenylamino)-1,6,7-trimethyl-1,8-dihydro-imidazo[4,5-h]isoquinoline-9-one;

N-Benzyl-3-[2-(2,6-Dichlorophenylamino)-1-methyl-9-oxo-8,9-dihydro-1H-imidazo[4,5-h]isoquinolin-7-yl]-acrylamide;

3-[2-(2,6-Dichlorophenylamino)-1-methyl-9-oxo-8,9-dihydro-1H-imidazo[4,5-h]isoquinolin-7-yl]-acrylic acid 4-morpholine amide;

2-(2,6-Dichlorophenylamino)-1,7-dimethyl-6-[3-(4-morpholino)propyl]-1,8-dihydro-imidazo[4,5-h]isoquinoline-9-one;

2-(2,6-Dichlorophenylamino)-4-hydroxymethyl-1,6,7-trimethyl-1,8-dihydro-imidazo[4,5-h]isoquinoline-9-one;

2-(2,6-Dimethylphenylamino)-1,6,7-trimethyl-1,8-dihydro-imidazo[4,5-h]isoquinoline-9-one;

2-(2-Ethyl-6-methylphenylamino)-1,6,7-trimethyl-1,8-dihydro-imidazo[4,5-h]isoquinoline-9-one;

2-(2,6-Dichlorophenylamino)-1,7-dimethyl-6-(3-phenylaminopropyl)-1,8-dihydro-imidazo[4,5-h]isoquinoline-9-one;

2-(2,6-Dichlorophenylamino-6-{3-[4-(2-diethylaminoethoxy)-phenylamino]propyl}-1,7-dimethyl-1,8-dihydro-imidazo[4,5-h]isoquinoline-9-one;

2-(2-Bromo-6-chloro-4-fluorophenylamino)-1,6,7-trimethyl-1,8-dihydro-imidazo[4,5-h]isoquinolin-9-one;

2-(2,6-Dichlorophenylamino)-4-(2-hydroxyethylaminomethyl)-1,6,7-trimethyl-1,8-dihydro-imidazo[4,5-h]isoquinoline-9-one;

2-(2,6-Dichlorophenylamino)-4-(4-methoxybenzylaminomethyl)-1,6,7-trimethyl-1,8-dihydro-imidazo[4,5-h]isoquinoline-9-one;

2-(2,6-Dichlorophenylamino)-1,6-dimethyl-7-vinyl-1,8-dihydro-imidazo[4,5-h]isoquinoline-9-one;

2-(2,6-Dichlorophenylamino)-4-(2,6-difluoropyridin-3yl)-1,6,7-trimethyl-1,8-dihydro-imidazo[4,5-h]isoquinoline-9-one;

2-(2,6-Dichlorophenylamino)-4-(3 -methylphenyl)-1,6,7-trimethyl-1,8-dihydro-imidazo[4,5-h]isoquinoline-9-one;

2-(2,6-Dichlorophenylamino)-1,7-dimethyl-9-oxo-1,8-dihydro-imidazo[4,5-h]isoquinoline-6-carboxylic acid 2-(4-moropholino)ethyl ester;

2-(2,6-Dichlorophenylamino)-4-(3-hydroxy-2-oxo-propyl)-1,6,7-trimethyl-1,8-dihydro-imidazo[4,5-h]isoquinoline-9-one;

N-4-(2-Diethylaminoethoxy)phenyl-3-[2-(2,6-dichlorophenylamino)-1-methyl-9-oxo-8,9-dihydro-1H-imidazo[4,5-h]isoquinoline-7-yl]-acrylamide;

3 -[2-(2,6-Dichlorophenylamino)-1-methyl-9-oxo-8,9-dihydro-1H-imidazo[4,5 -h]isoquinolin-7-yl]-N-methyl acrylamide;

9- Hydroxy-2-(2,6-dichlorophenylamino)-3,5,6,7,8,9-hexahydro-imidazo[4,5-i]phenanthridin-4-one;

2-(2,6-Dichlorophenylamino)-1,6-dimethyl-7-(3-hydroxypropen-1-yl)-1,8-dihydro-imidazo[4,5-h]-isoquinoline-9-one;

2-(2,6-Dichlorophenylamino)-1,6-dimethyl-7-(2-phenylethenyl)-1,8-dihydro-imidazo[4,5-h]-isoquinoline-9-one;

2-(2-Amino-6-chlorophenylamino)-1,6,7-trimethyl-1,8-dihydro-imidazo[4,5-h]isoquinoline-9-one;

2-(2,6-Dichlorophenylamino)-1,6,7-trimethyl-4-vinyl-1,8-dihydro-imidazo[4,5-h]isoquinoline-9-one;

2-(2,6-Dichlorophenylamino)-4-(3-methoxypropyn-1-yl)-1,6,7-trimethyl-1,8-dihydro-imidazo[4,5h]isoquinoline-9-one;

2-(2,6-Dichlorophenylamino)-1,6,7-trimethyl-4-(5-phenylpent-1-ynyl)-1,8-dihydro-imidazo[4,5-h]isoquinoline-9-one;

2-(2,6-Dichlorophenylamino)-1,6-dimethyl-7-oxazol-5-yl-1,8-dihydro-imidazo[4,5-h]isoquinolin-9-one;

2-(2,6-Dichlorophenylamino)-1-methyl-7-vinyl-1,8-dihydro-imidazo[4,5-h]isoquinoline-9-one;

2-(2,6-Dichlorophenylamino)-1,6-dimethyl-7-(3-morpholin-4-yl-propen-1-yl)-1,8-dihydro-imidazo[4,5-h]-isoquinoline-9-one;

2-(2,6-Dichlorophenylamino)-1,7-dimethyl-6-[2-(2-hydroxyethyl)aminoethyl]-1,8-dihydro-imidazo[4,5-h]isoquinoline-9-one;

3-[2-(2,6-Dichlorophenylamino)-1,7-dimethyl-9-oxo-8,9-dihydro-1H-imidazo[4,5-h]isoquinolin-7-yl]-acrylonitrile;

2-(2-Chloro-6-methylphenylamino)-1,7-dimethyl-1,8-dihydro-imidazo[4,5-h]isoquinoline-9-one;

2-(2,6-Dichlorophenylamino)-1-methyl-7-oxazol-5-yl-1,8-dihydro-imidazo[4,5-h]isoquinolin-9-one;

2-(2,6-Dichlorophenylamino)-1,7-dimethyl-6-(3-hydroxypropyl)-1,8-dihydro-imidazo[4,5-h]isoquinoline-9-one;

2-(2,6-Dichlorophenylamino)-7-(3-hydroxypropen-1-yl)-1-methyl-1,8-dihydro-imidazo[4,5-h]-isoquinolin-9-one;

2-(2-Chloro-6-methylphenylamino)-7-(3-hydroxypropen-1-yl)-1-methyl-1,8-dihydro-imidazo[4,5-h]-isoquinolin-9-one;

2-(2,6-Dichlorophenylamino)-7-(3-diethylaminopropen-1-yl)-1,6-dimethyl-1,8-dihydro-imidazo[4,5-h]-isoquinolin-9-one;

7-(3-Aminopropen-1-yl)-2-(2,6-dichlorophenylamino)-1,6-dimethyl-1,8-dihydro-imidazo[4,5-h]-isolquinolin-9-one;

2-(2,6-Dichlorophenylamino)-1,6-dimethyl-7-(3-pyrrolidin-1-yl-propen-1-yl)-1,8-dihydro-imidazo[4,5-h]-isoquinolin-9-one;

7-(3-Benzylmethylaminopropen-1-yl)2-(2,6-dichlorophenylamino)-1,6-dimethyl-1,8-dihydro-imidazo[4,5-h]-isoquinolin-9-one;

2-(2,6-Dichloro-4-methoxyphenylamino)-1,6,7-trimethyl-1,8-dihydro-imidazo[4,5-h]isoquinoline-9-one;

2-(2,6-Dichloro-4-methoxyphenylamino)-1,6-dimethyl-7-oxazol-5-yl-1,8-dihydro-imidazo[4,5-h]isoquinolin-9-one;

2-(2,6-Dichlorophenylamino)-7-(3-diethylaminopropen-1-yl)-1-methyl-1,8-dihydro-imidazo[4,5-h]-isoquinolin-9-one;

2-(2,6-Dimethylphenylamino)-1,7-dimethyl-1,8-dihydro-imidazo[4,5-h]isoquinoline-9-one;

2-(2,6-Dichlorophenylamino)-1,6-dimethyl-7-(4-methylpiperazin-1-yl-propen-1-yl)-1,8-dihydro-imidazo[4,5-h]-isoquinolin-9-one;

2-(2,6-Dichlorophenylamino)-1,6-dimethyl-7-(3-piperidin-1-yl-propen-1-yl)-1,8-dihydro-imidazo[4,5-h]-isoquinolin-9-one;

2-(2,6-Dichlorophenylamino)-1,6-dimethyl-7-{3-[ethyl(2-hydroxyethyl)amino]propen-1-yl}-1,8-dihydro-imidazo[4,5-h]-isoquinolin-9-one;

2-(2,6-Dichlorophenylamino)-1,6-dimethyl-7-[3-(3-hydroxypyrrolidin-1-yl)-propen-1-yl]-1,8-dihydro-imidazo[4,5-h]-isoquinolin-9-one;

7-(3-Dibutylaminopropen-1-yl)-2-(2,6-dichlorophenylamino)-1,6-dimethyl-1,8-dihydro-imidazo[4,5-h]-isoquinolin-9-one;

2-(2,6-Dichlorophenylamino)-1,6-dimethyl-7-{3-[(2-methoxyethyl)methylamino]propen-1-yl}-1,8-dihydro-imidazo[4,5-h]-isoquinolin-9-one;

7-(3-Diethylaminopropen-1-yl)-1,6-dimethyl-2-(2,6-dimethylphenylamino)-1,8-dihydro-imidazo[4,5-h]-isoquinolin-9-one;

2-(2,6-Dichlorophenylamino)-7-{3-[(2-diethylaminoethyl)methylamino]-propen-1-yl}-1,6-dimethyl-1,8-dihydro-imidazo[4,5-h]-isoquinolin-9-one;

7-(3-Diethylaminopropen-1-yl)-1,6-dimethyl-2-(2,4,6-trichlorophenylamino)-1,8-dihydro-imidazo[4,5-h]-isoquinolin-9-one 2-(2,6-Dichlorophenylamino)-6-methyl-7-oxazol-5-yl-1,8-dihydro-imidazo[4,5-h]isoquinolin-9-one 2-(2,6-Dichlorophenylamino)-1,6-dimethyl-7-[3-(2-pyrrolidin-1-ylmethylpyrrolidin-1-yl)-propen-1-yl]-1,8-dihydro-imidazo[4,5-h]-isoquinolin-9-one 7-[3-(2S-Aminomethylpyrrolidin-1-yl)-propen-1-yl]-2-(2,6-dichlorophenylamino)-1,6-dimethyl-1,8-dihydro-imidazo[4,5-h]-isoquinolin-9-one 1-{3-[2-(2,6-Ddichlorophenylamino)-1,6-dimethyl-9-oxo-8,9-dihydro-1H-imidazo[4,5-h]-isoquinolin-7-yl]-propenyl}-L-proline carboxamide 1-{3-[2-(2,6-dichlorophenylamino)-1,6-dimethyl-9-oxo-8,9-dihydro-1H-imidazo[4,5-h]isoquinolin-7-yl]-propenyl}-piperidine-3-carboxamide 2-(2,6-Dichlorophenylamino)-1,6-dimethyl-7-(methylhydrazonomethyl)-1,8-dihydro-imidazo[4,5-h]-isoquinolin-9-one 7-[3-(3-Aminopyrrolidin-1-yl)-propen-1-yl]-2-(2,6-dichlorophenylamino)-1,6-dimethyl-1,8-dihydro-imidazo[4,5-h]-isoquinolin-9-one 2-(2,6-Dichlorophenylamino)-1,6-dimethyl-7-[3-(3-acetamidopyrrolidin-1-yl)-propen-1-yl]-1,8-dihydro-imidazo[4,5-h]-isoquinolin-9-one 2-(2,6-Dichlorophenylamino)-1,6-dimethyl-7-[3-(3-dimethylaminopyrrolidin-1-yl)-propen-1-yl]-1,8-dihydro-imidazo[4,5-h]-isoquinolin-9-one 1-{3-[2-(2,6-Dichlorophenylamino)-1,6-dimethyl-9-oxo-8,9-dihydro-1H-imidazo[4,5-h]isoquinolin-7-yl]-propenyl}-piperidine-2-carboxamide 7-[3-(3-Aminomethylpiperidin-1-yl)-propen-1-yl]-2-(2,6-dichlorophenylamino)-1,6-dimethyl-1,8-dihydro-imidazo[4,5-h]-isoquinolin-9-one 1-{3-[2-(2,6-Dichlorophenylamino)-1,6-dimethyl-9-oxo-8,9-dihydro-1H-imidazo[4,5-h]isoquinolin-7-yl]-propenyl}-piperidine-3-carboxylic acid diethylamide 2-(2,6-Dichlorophenylamino)-1,6-dimethyl-7-ethynyl-1,8-dihydro-imidazo[4,5-h]-isoquinolin-9-one 1-{3-[2-(2,6-dichlorophenylamino)-1,6-dimethyl-9-oxo-8,9-dihydro-1H-imidazo[4,5-h]isoquinolin-7-yl]-propenyl}-3-methyl urea Cyclohexane carboxylic acid {3-[2-(2,6-dichlorophenylamino)-1,6-dimethyl-9-oxo-8,9-dihydro-1H-imidazo[4,5-]isoquinolin-7-yl]propenyl}amide 2-(2,6-Dichlorophenylamino)-1-methyl-7-phenyl-1,8-dihydro-imidazo[4,5-h]isoquinolin-9-one N-{3-[2-(2,6-Dichlorophenylamino)-1,6-dimethyl-9-oxo-8,9-dihydro-1H-imidazo[4,5-h]isoquinolin-7-yl]-propenyl} methanesulfonamide 3-[2-(2,6-dichlorophenylamino)-1,6-dimethyl-9-oxo-8,9-dihydro-1H-imidazo[4,5-h]isoquinolin-7yl]-propenyl urea 1-Cyclohexyl-3-{3-[2-(2,6-dichlorophenylamino)-1,6-dimethyl-9-oxo-8,9-dihydro-1H-imidazo[4,5-h]isoquinolin-7-yl]-propenyl}-urea N-{13-[2-(2,6-Dichlorophenylamino)-1,6-dimethyl-9-oxo-8,9-dihydro-1H-imidazo[4,5-h]isoquinolin-7-yl]-propenyl} benzenesulfonamide 2-(2,6-Dichlorophenylamino)-1,6-dimethyl-7-(3-ethylaminopropen-1-yl)-1,8-dihydro-imidazo[4,5h]-isoquinolin-9-one N-{13-[2-(2,6-Dichlorophenylamino)-1,6-dimethyl-9-oxo-8,9-dihydro-1H-imidazo[4,5-h]isoquinolin-7-yl]-propenyl}-guanidine Piperidine-3-carboxylic acid {3-[2-(2,6-dichlorophenylamino)-1,6-dimethyl-9-oxo-8,9-dihydro-1H-imidazo[4,5-h]isoquinolin-7-yl]-propenyl}amide L-Proline {3-[2-(2,6-dichlorophenylamino)-1,6-dimethyl-9-oxo-8,9-dihydro-1H-imidazo[4,5-h]isoquinolin-7-yl]-propenyl}amide D-Proline {3-[2-(2,6-dichlorophenylamino)-1,6-dimethyl-9-oxo-8,9-dihydro-1H-imidazo[4,5-h]isoquinolin-7-yl]-propenyl}amide 3-[2-(2,6-Dichlorophenylamino)-1,6-dimethyl-9-oxo-8,9-dihydro-1H-imidazo[4,5-h]isoquinolin-7-yl]-benzamide L-Azetidine-2-carboxylic acid {3-[2-(2,6-dichlorophenylamino)-1,6-dimethyl-9-oxo-8,9-dihydro-1H-imidazo[4,5-h]isoquinolin-7-yl]-propenyl}amide Piperidine-2-carboxylic acid {3-[2-(2,6-dichlorophenylamino)-1,6-dimethyl-9-oxo-8,9-dihydro-1H-imidazo[4,5-h]isoquinolin-7-yl]propenyl}amide;

2-(2-Chloro-6-methylphenylamino)-7-(3-diethylaminopropen-1-yl)-1,6-dimethyl-1,8-dihydro-imidazo[4,5-h]-isoquinolin-9-one;

2-(2,6-Dichlorophenylamino)-1,6-dimethyl-7-{3-[(3-dimethylamino-propyl)methylamino]-propen-1-yl}-1,8-dihydro-imidazo[4,5-h]-isoquinolin-9-one;

2-(2,6-Dichlorophenylamino)-7-[3-(2-diethylaminoethylthio)-propen-1-yl]-1,6-dimethyl-1,8-dihydro-imidazo[4,5-h]-isoquinolin-9-one;

2-(2,6-Dichlorophenylamino)-1,6-dimethyl-7-(3-dimethylaminopropen-1-yl)-1,8-dihydro-imidazo[4,5-h]-isoquinolin-9-one;

7-(3-N-Cyclohexyl-N-methylaminopropen-1-yl)-2-(2,6-dichlorophenylamino)-1,6-dimethyl-1,8-dihydro-imidazo[4,5-h]-isoquinolin-9-one;

2-(2,6-Dichlorophenylamino)-1,6-dimethyl-7-(3-N-isopropyl-N-methylaminopropen-1-yl)-1,8-dihydro-imidazo[4,5-h]-isoquinolin-9-one; and the pharmacuetically acceptable derivatives thereof.

In yet still a further embodiment of the invention, there are provided the following compounds of the fomulas (I) and (Ia):

2-(2,6-Dichlorophenylamino)-3,5-dihydro-imidazo[4,5-i]phenanthridin-4-one;

2-(2,6-Dichlorophenylamino)-1,6,7-trimethyl-1,8-dihydro-imidazo[4,5-h]isoquinoline-9-one;

2-(2,6-Dichlorophenylamino)-1,7-dimethyl-6-(2-hydroxyethyl)-1,8-dihydro-imidazo[4,5-h]isoquinoline-9-one;

2-(2,6-Dichlorophenylamino)-1,7-dimethyl-9-oxo-1,8-dihydro-imidazo[4,5-h]isoquinoline-6-carboxylic acid methyl ester;

3-[2-(2,6-Dichlorophenylamino)-1-methyl-9-oxo-8,9-dihydro-1H-imidazo[4,5-h]isoquinolin-7-yl]-aryclic acid methyl ester;

2-(2-Chloro-6-methylphenylamino)-1,6,7-trimethyl-1,8-dihydro-imidazo[4,5-h]isoquinoline-9-one;

3-[2-(2,6-Dichlorophenylamino)-1-methyl-9-oxo-8,9-dihydro-1H-imidazo[4,5-h]isoquinolin-7-yl]-N-methoxy-N-methylacrylamide;

2-(2-Chloro-6-nitrophenylamino)-1,6,7-trimethyl-1,8-dihydro-imidazo[4,5-h]isoquinoline-9-one;

N-Benzyl-3-[2-(2,6-Dichlorophenylamino)-1-methyl-9-oxo-8,9-dihydro-1H-imidazo[4,5-h]isoquinolin-7-yl]-acrylamide;

3-[2-(2,6-Dichlorophenylamino)-1-methyl-9-oxo-8,9-dihydro-1H-imidazo[4,5-h]isoquinolin-7-yl]-acrylic acid 4-morpholine amide;

2-(2,6-Dichlorophenylamino)-4-hydroxymethyl-1,6,7-trimethyl-1,8-dihydro-imidazo[4,5-h]isoquinoline-9-one;

2-(2,6-Dichlorophenylamino)-1,6-dimethyl-7-vinyl-1,8-dihydro-imidazo[4,5-h]isoquinoline-9-one;

2-(2,6-Dichlorophenylamino)-1,7-dimethyl-9-oxo-1,8-dihydro-imidazo[4,5-h]isoquinoline-6-carboxylic acid 2-(4-morpholino)ethyl ester;

2-(2,6-Dichlorophenylamino)-1,6-dimethyl-7-(3-hydroxypropen-1-yl)-1,8-dihydro-imidazo[4,5-h]-isoquinolin-9-one;

2-(2,6-Dichlorophenylamino)-1,6-dimethyl-7-oxazol-5-yl-1,8-dihydro-imidazo[4,5-h]isoquinolin-9-one;

2-(2,6-Dichlorophenylamino)-1-methyl-7-vinyl-1,8-dihydro-imidazo[4,5-h]isoquinoline-9-one;

2-(2,6-Dichlorophenylamino)-1,6-dimethyl-7-(3-morpholin-4-yl-propen-1-yl)-1,8-dihydro-imidazo[4,5-h]-isoquinolin-9-one;

3-[2-(2,6-Dichlorophenylamino)-1,7-dimethyl-9-oxo-8,9-dihydro-1H-imidazo[4,5-h]isoquinolin-7-yl]-acrylonitrile;

2-(2-Chloro-6-methylphenylamino)-1,7-dimethyl-1,8-dihydro-imidazo[4,5-h]isoquinoline-9-one;

2-(2,6-Dichlorophenylamino)-1-methyl-7-oxazol-5-yl-1,8-dihydro-imidazo[4,5-h]isoquinolin-9-one;

2-(2,6-Dichlorophenylamino)-7-(3-hydroxypropen-1-yl)-1-methyl-1,8-dihydro-imidazo[4,5-h]-isoquinolin-9-one;

2-(2-Chloro-6-methylphenylamino)-7-(3-hydroxypropen-1-yl)-1-methyl-1,8-dihydro-imidazo[4,5-h]-isoquinolin-9-one;

2-(2,6-Dichlorophenylamino)-7-(3-diethylaminopropen-1-yl)-1,6-dimethyl-1,8-dihydro-imidazo[4,5-h]-isoquinolin-9-one;

2-(2,6-Dichlorophenylamino)-1,6-dimethyl-7-(3-pyrrolidin-1-yl-propen-1-yl)-1,8-dihydro-imidazo[4,5-h]-isoquinolin-9-one;

2-(2,6-Dichlorophenylamino)-7-(3-diethylaminopropen-1-yl)-1-methyl-1,8-dihydro-imidazo[4,5-h]-isoquinolin-9-one;

2-(2,6-Dichlorophenylamino)-1,6-dimethyl-7-(4-methylpiperazin-1-yl-propen-1-yl)-1,8-dihydro-imidazo[4,5-h]-isoquinolin-9-one;

2-(2,6-Dichlorophenylamino)-1,6-dimethyl-7-(3-piperidin-1-yl-propen-1-yl)-1,8-dihydro-imidazo[4,5-h]-isoquinolin-9-one;

2-(2,6-Dichlorophenylamino)-1,6-dimethyl-7-{3-[ethyl(2-hydroxyethyl)amino]propen-1-yl}-1,8-dihydro-imidazo[4,5-h]-isoquinolin-9-one;

7-(3-Diethylaminopropen-1-yl)-1,6-dimethyl-2-(2,6-dimethylphenylamino)-1,8-dihydro-imidazo[4,5-h]-isoquinolin-9-one;

2-(2,6-Dichlorophenylamino)-7-{3-[(2-diethylaminoethyl)methylamino]-propen-1-yl}-1,6-dimethyl-1,8-dihydro-imidazo[4,5-h]-isoquinolin-9-one;

7-(3-Diethylaminopropen-1-yl)-1,6-dimethyl-2-(2,4,6-trichlorophenylamino)-1,8-dihydro-imidazo[4,5-h]-isoquinolin-9-one 2-(2,6-Dichlorophenylamino)-6-methyl-7-oxazol-5-yl-1,8-dihydro-imidazo[4,5-h]isoquinolin-9-one 2-(2,6-Dichlorophenylamino)-1,6-dimethyl-7-[3-(2-pyrrolidin-1-ylmethylpyrrolidin-1-yl)-propen-1-yl]-1,8-dihydro-imidazo[4,5-h]-isoquinolin-9-one 7-[3-(2S-Aminomethylpyrrolidin-1-yl)-propen-1-yl]-2-(2,6-dichlorophenylamino)-1,6-dimethyl-1,8-dihydro-imidazo[4,5-h]-isoquinoloin-9-one 1-{3-[2-(2,6-Ddichlorophenylamino)-1,6-dimethyl-9-oxo-8,9-dihydro-1H-imidazo[4,5-h]isoquinolin-7-yl]-propenyl}-L-proline carboxamide 1-{3-[2-(2,6-dichlorophenylamino)-1,6-dimethyl-9-oxo-8,9-dihydro-1H-imidazo[4,5-h]isoquinolin-7-yl]-propenyl}-piperidine-3-carboxamide 2-(2,6-Dichlorophenylamino)-1,6-dimethyl-7-(methylhydrazonomethyl)-1,8-dihydro-imidazo[4,5-h]-isoquinolin-9-one 7-[3-(3-Aminopyrrolidin-1-yl)-propen-1-yl]-2-(2,6-dichlorophenylamino)-1,6-dimethyl-1,8-dihydro-imidazo[4,5-h]-isoquinolin-9-one 2-(2,6-Dichlorophenylamino)-1,6-dimethyl-7-[3-(3-acetamidopyrrolidin-1-yl)-propen-1-yl]-1,8-dihydro-imidazo[4,5-h]-isoquinolin-9-one 2-(2,6-Dichlorophenylamino)-1,6-dimethyl-7-[3-(3-dimethylaminopyrrolidin-1-yl)-propen-1-yl]-1,8-dihydro-imidazo[4,5-h]-isoquinolin-9-one 1-{3-[2-(2,6-Dichlorophenylamino)-1,6-dimethyl-9-oxo-8,9-dihydro-1H-imidazo[4,5-h]isoquinolin-7-yl]-propenyl}-piperidine-2-carboxamide 7-[3-(3-Aminomethylpiperidin-1-yl)-propen-1-yl]-2-(2,6-dichlorophenylamino)-1,6-dimethyl-1,8-dihydro-imidazo[4,5-h]-isoquinolin-9-one 1-{3-[2-(2,6-Dichlorophenylamino)-1,6-dimethyl-9-oxo-8,9-dihydro-1H-imidazo[4,5-h]isoquinolin-7-yl]-propenyl}-piperidine-3-carboxylic acid diethylamide 2-(2,6-Dichlorophenylamino)-1,6-dimethyl-7-ethynyl-1,8-dihydro-imidazo[4,5-h]-isoquinolin-9-one 1-{3-[2-(2,6-dichlorophenylamino)-1,6-dimethyl-9-oxo-8,9-dihydro-1H-imidazo[4,5-h]isoquinolin-7-yl]-propenyl}-3-methyl urea Cyclohexane carboxylic acid {3-[2-(2,6-dichlorophenylamino)-1,6-dimethyl-9-oxo-8,9-dihydro-1H-imidazo[4,5-h]isoquinolin-7-yl]-propenyl}-amide 2-(2,6-Dichlorophenylamino)-1-methyl-7-phenyl-1,8-dihydro-imidazo[4,5-h]isoquinolin-9-one N-{3-[2-(2,6-Dichlorophenylamino)-1,6-dimethyl-9-oxo-8,9-dihydro-1H-imidazo[4,5-h]isoquinolin-7-yl]-propenyl}methanesulfonamide 3-[2-(2,6-Dichlorophenylamino)-1,6-dimethyl-9-oxo-8,9-dihydro-1H-imidazo[4,5-h]isoquinolin-7-yl]-propenyl urea 1-Cyclohexyl-3-{3-[2-(2,6-dichlorophenylamino)-1,6-dimethyl-9-oxo-8,9-dihydro-1H-imidazo[4,5-h]isoquinolin-7-yl]-propenyl}-urea N-{3-[2-(2,6-Dichlorophenylamino)-1,6-dimethyl-9-oxo-8,9-dihydro-1H-imidazo[4,5-h]isoquinolin-7-yl]-propenyl}benzenesulfonamide 2-(2,6-Dichlorophenylamino)-1,6-dimethyl-7-(3-ethylaminopropen-1-yl)-1,8-dihydro-imidazo[4,5-h]-isoquinolin-9-one N-{3-[2-(2,6-Dichlorophenylamino)-1,6-dimethyl-9-oxo-8,9-dihydro-1H-imidazo[4,5-h]isoquinolin-7-yl]-propenyl}-guanidine Piperidine-3-carboxylic acid {3-[2-(2,6-dichlorophenylamino)-1,6-dimethyl-9-oxo-8,9-dihydro-1H-imidazo[4,5-h]isoquinolin-7-yl]-propenyl}amide L-Proline {3-[2-(2,6-dichlorophenylamino)-1,6-dimethyl-9-oxo-8,9-dihydro-1H-imidazo[4,5-h]isoquinolin-7-yl]-propenyl}amide D-Proline {3-[2-(2,6-dichlorophenylamino)-1,6-dimethyl-9-oxo-8,9-dihydro-1H-imidazo[4,5-h]isoquinolin-7-yl]-propenyl}amide 3-[2-(2,6-Dichlorophenylamino)-1,6-dimethyl-9-oxo-8,9-dihydro-1H-imidazo[4,5-h]isoquinolin-7-yl]-benzamide L-Azetidine-2-carboxylic acid {3-[2-(2,6-dichlorophenylamino)-1,6-dimethyl-9-oxo-8,9-dihydro-1H-imidazo[4,5-h]isoquinolin-7-yl]-propenyl}amide Piperidine-2-carboxylic acid {3-[2-(2,6-dichlorophenylamino)-1,6-dimethyl-9-oxo-8,9-dihydro-1H-imidazo[4,5-h]isoquinolin-7-yl]-propenyl}amide;

2-(2-Chloro-6-methylphenylamino)-7-(3-diethylaminopropen-1-yl)-1,6-dimethyl-1,8-dihydro-imidazo[4,5-h]-isoquinolin-9-one;

2-(2,6-Dichlorophenylamino)-1,6-dimethyl-7-{3-[(3-dimethylamino-propyl)methylamino]-propen-1-yl}-1,8-dihydro-imidazo[4,5-h]-isoquinolin-9-one;

2-(2,6-Dichlorophenylamino)-7-[3-(2-diethylaminoethylthio)-propen-1-yl]-1,6-dimethyl-1,8-dihydro-imidazo[4,5-h]-isoquinolin-9-one;

2-(2,6-Dichlorophenylamino)-1,6-dimethyl-7-(3-dimethylaminopropen-1-yl)-1,8-dihydro-imidazo[4,5-h]-isoquinolin-9-one;

7-(3-N-Cyclohexyl-N-methylaminopropen-1-yl)-2-(2,6-dichlorophenylamino)-1,6-dimethyl-1,8-dihydro-imidazo[4,5-h]-isoquinolin-9-one;

2-(2,6-Dichlorophenylamino)-1,6-dimethyl-7-(3-N-isopropyl-N-methylaminopropen-1-yl)-1,8-dihydro-imidazo[4,5-h]-isoquinolin-9-one; and the pharmacuetically acceptable derivatives thereof.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

All terms as used herein in this specification, unless otherwise stated, shall be understood in their ordinary meaning as known in the art. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched or unbranched unless otherwise specified. Other more specific definitions are as follows:

The term "halogen" as used in the present specification shall be understood to mean bromine, chlorine, fluorine or iodine.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Example "heteroaryl" radicals include, pyridinyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, 2,4-dioxo-quinazolinyl, imidazo[4,5-c]pyridinyl and indazolyl, or a fused heteroaryl such as cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene;

The term "heterocycle" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Example "heterocycle"

radicals include azetidinyl, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, 2,3-dihydrobenzimidazolyl and 2,3-dihydro-1H-imidazo[4,5-c] pyridinyl. As used herein and throughout this specification, the terms "nitrogen" and "sulfur" and their respective elements symbols include any oxidized form of nitrogen and sulfur and the quaternized form of any basic nitrogen.

The term "aryl" shall be understood to mean a 6–10 membered aromatic carbocycle, "aryl" includes, for example, phenyl and naphthyl; other terms comprising "aryl" will have the same definition for the aryl component, examples of these moieties include: arylalkyl, aryloxy or arylthio.

The term "carbocycle" shall be understood to mean a 3–10 membered aromatic or nonaromatic cyclic carbon chain. Examples of nonaromatic carbocycles include cyclopropyl, cyclobutyl, cyclopentyl and the like. Examples of aromatic carbocycles include the "aryl" compounds as described hereinabove.

The term "acyl" shall be understood to mean an R—(C=O)— moiety wherein R is an alkyl. Examples of R can be a $C_{1-10}$alkyl, saturated or unsaturated, branched or unbranched, or R can be "aryl" as defined hereinabove. "Acyloxy" shall be understood to mean an R—$CO_2$— group wherein R is as defined in this paragraph.

The invention includes pharmaceutically acceptable derivatives of compounds of the invention. A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1–C_4$ alkyl$)_4^+$ salts.

In addition, the compounds of this invention include prodrugs of compounds of the invention. Prodrugs include those compounds that, upon simple chemical transformation, are modified to produce a compound of the invention. Simple chemical transformations include hydrolysis, oxidation and reduction, enzymatically, metabolically or otherwise. Specifically, when a prodrug of this invention is administered to a patient, the prodrug may be transformed into a compound of the invention, thereby imparting the desired pharmacological effect.

General Synthetic Methods

The compounds of the invention may be prepared by the methods described below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. If desired, intermediates and products may be purified by chromatography on silica gel and/or recrystallization. Starting materials and reagents are either commercially available or may be prepared by one skilled in the art using methods described in the chemical literature.

A general procedure (Method A) that may be used to synthesize compounds of formula (I) is illustrated in Scheme I.

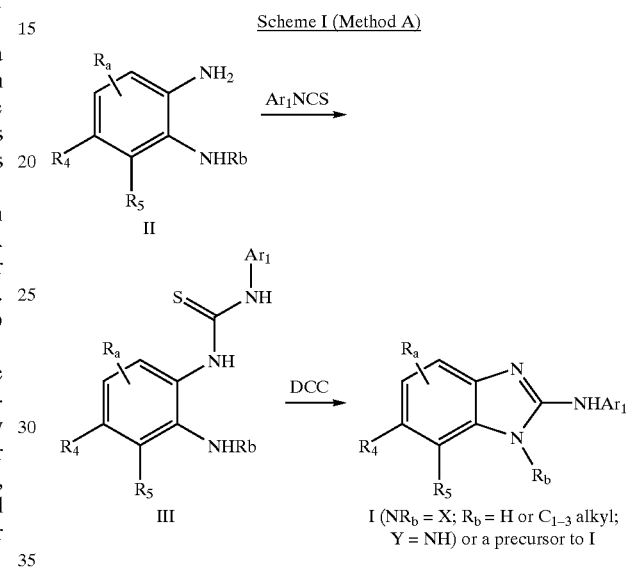

An optionally substituted diamine II is reacted with an aryl isothiocyanate in a suitable solvent such as EtOAc, DMF or THF at about ambient to reflux temperature for about 3 to 24 hr to provide thiourea III. Alternately, one can begin with a salt of II and react with an aryl isothiocyanate in pyridine or in a neutral solvent such as THF in the presence of a suitable base such as triethylamine. Reaction of the thiourea with a suitable activating agent such as 1,3-dicyclohexylcarbodiimide (DCC) or mercuric oxide in a suitable solvent such as THF or DMF at about ambient to reflux temperature provides I or a precursor to I which may undergo further chemical transformation to obtain the desired compound. If desired, one may perform the two steps without isolating the thiourea, by adding DCC or mercuric oxide to the reaction of II and the aryl isothiocyanate.

One may also prepare benzothiazoles (formula I, X=S) by Method A, starting with the analogous aminothiophenol. Preferably, one may also use Method B illustrated in Scheme II and described below.

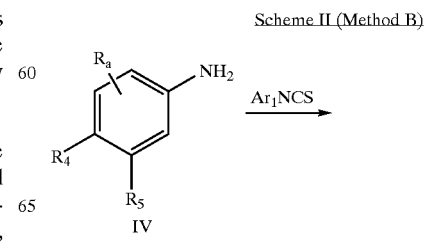

-continued

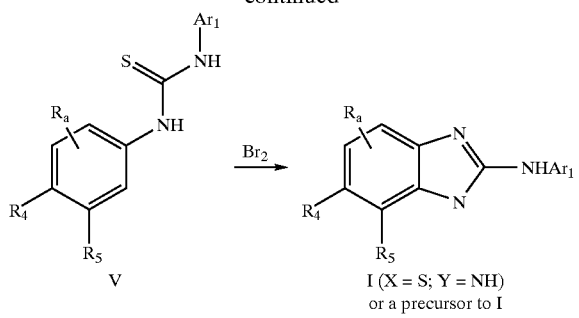

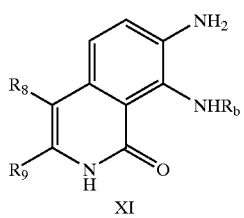

In this method, an appropriately substituted aniline is reacted with an aryl isothiocyanate as in Method A to provide thiourea V. Reaction of V under cyclizing conditions, such as in the presence of bromine in a suitable solvent such as chloroform at about reflux temperature, provides I (X=S) or a precursor to I.

The starting diamine (II) in Method A may be prepared by reduction of a nitroaniline, for example under hydrogen atmosphere in the presence of a suitable catalyst such as palladium on carbon in a suitable solvent, such as EtOAc or HOAc.

One procedure (Method C) for preparing starting nitroanilines is illustrated in Scheme III and described below.

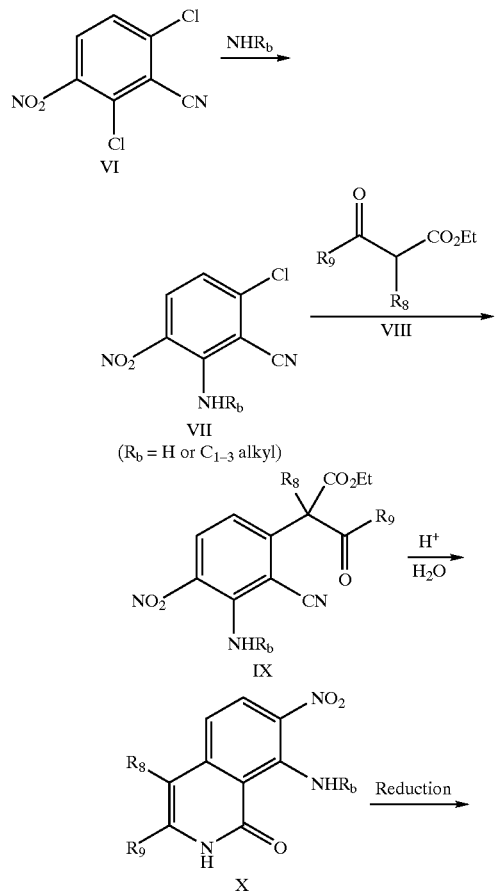

In Method C, 2,6-dichloro-3-nitrobenzonitrile (VI) is reacted with an amine in a suitable solvent, such as EtOH, THF or EtOAc, optionally in a pressure flask and at about 0 to 80° C., to provide VII. Reaction of VII with keto-ester VIII in the presence of a suitable base, such as $K_2CO_3$, potassium t-butoxide or 1,8-diazabicyclo[5.4.0]undec-7-ene (DBU) in a suitable solvent, such as DMF or DMSO at about ambient temperature provides IX. Hydrolysis and cyclization of IX to provide X is accomplished by reaction with aqueous acid, for example a mixture of acetic acid, sulfuric acid and water at about reflux temperature. Reduction of nitroaniline X, in a suitable solvent, preferably acetic acid and/or trifluoroacetic acid, as described above, provides XI.

In a variation of Method C, one may reduce intermediate IX as described above, to the corresponding diamine and form the benzimidazole by Method A prior to formation of the isoquinolinone.

A procedure for introducing $R_A$ into compounds of formula (I) is illustrated in Scheme IV.

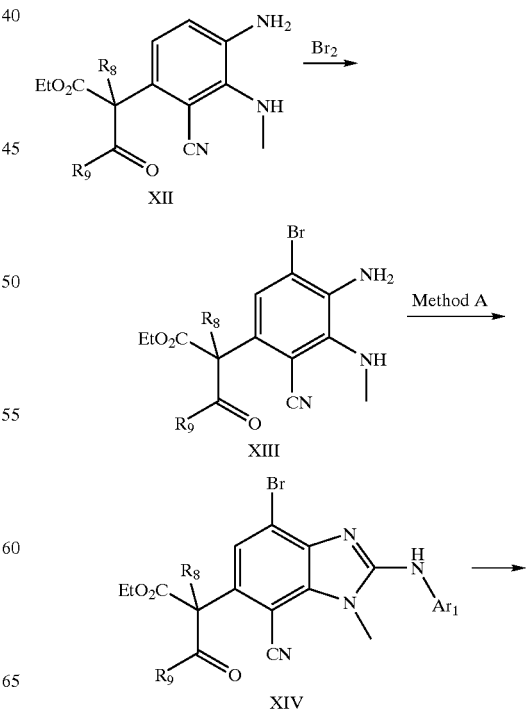

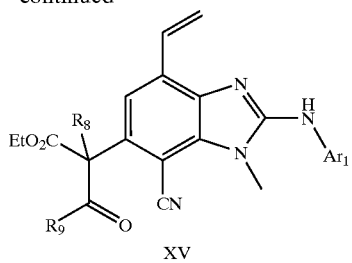

XV

Intermediate XII (prepared as described in Scheme III for preparation of IX, followed by reduction) is reacted with bromine in a suitable solvent, such as chloroform at ambient temperature to provide XIII. Intermediate XIII is converted to XIV according to Method A. Cross-coupling chemistry can be used to introduce carbon in place of bromine. For example, reaction with vinyl tributyltin in the presence of a suitable catalyst, such as $(PPh_3)_2PdCl_2$, in a suitable solvent, such as 1-methyl-2-pyrrolidinone (NMP) at about 100° C., provides XV. Alternately, reaction with a terminal alkyne in the presence of a suitable catalyst, such as $(PPh_3)_2PdCl_2$, and CuI, and a suitable base, such as triethylamine in a solvent such as THF at about ambient temperature provides an alkyne as $R_a$. Other $R_a$ may be obtained by transformation of these $R_a$ by methods known to those skilled in the art. Several of these transformations are exemplified below.

A method for preparing compounds of the invention in which $R_4$ and $R_5$ represent ring B, which is based on the procedure described in *J. Heterocyclic Chem.*, 1970, 7, 615, is shown in Scheme V.

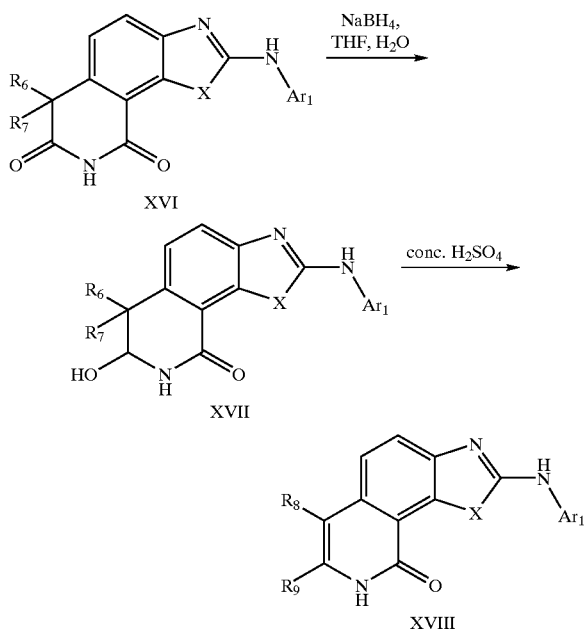

Intermediate XVI (prepared according to Method A or Method B) is reacted with a reducing agent such as sodium borohydride, in a suitable solvent, such as THF or dioxane, at about 0° C. to ambient temperature, to give intermediate XVII, in which one carbonyl of the imide has been reduced selectively. Treatment of XVII with a strong acid, such as sulfuric acid, at ambient temperature, causes rearrangement to the isoquinolone XVIII. It will be appreciated that this method is most suitable for compounds where $R_6$, $R_7$, $R_8$ and $R_9$ are all the same group, preferably methyl. In a variation of this method, the reduction of the imide and rearrangement to the isoquinolone can be carried out prior to forming the benzimidazole ring.

Functional groups at $R_8$ or $R_9$ on compounds of formula (I) or intermediates prepared as illustrated in the Schemes above may also be transformed by methods known to those skilled in the art to prepare additional compounds of the invention. Several of these transformations are also exemplified below.

Methods of Therapeutic Use

The compounds of the invention are useful in inhibiting the activity of src-family kinases and PDGFR kinase. In doing so, the compounds are effective in blocking disease processes mediated by these kinases. For example, by inhibiting p56 lck, the compounds block downstream signaling events following T cell activation by antigen. Activation of antigen-specific T cells is necessary for the induction and progression of diseases, including autoimmune diseases, allergic diseases and transplant rejection (J. H. Hanke et al., *Inflamm. Res.*, 1995, 44, 357). Therefore the compounds of the invention are useful for treating such diseases. These include but are not limited to rheumatoid arthritis, multiple sclerosis, Guillain-Barre syndrome, Crohn's disease, ulcerative colitis, psoriasis, graft versus host disease, systemic lupus erythematosus, insulin-dependent diabetes mellitus and asthma.

In view of their inhibitory effect on src-family kinases and PDGFR kinase, the compounds of the invention are useful in treating cancer. For example, the compounds of the invention are useful in treating src-dependent tumors, such as in mammary carcinoma, colon carcinoma, melanoma and sarcoma, and are also useful in treating PDGF-dependent tumors, such as ovarian cancer, prostate cancer and glioblastoma. In view of their inhibitory effect on src kinase, the compounds of the invention are also useful in treating conditions involving cerebral ischemia, for example, in reducing brain damage following a stroke.

By inhibiting p60src, compounds of the invention may also be useful in treating osteoporosis, Paget's disease, bone inflammation and joint inflammation. By inhibiting PDGFR kinase, compounds of the invention may also be useful in treating fibrotic diseases, restenosis and atherosclerosis. By inhibiting lyn kinase, the compounds of the invention may also be useful in enhancing or potentiating the effectiveness of radiation therapy.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, rectally, topically or by inhalation. The preferred modes of administration are oral and intravenous. Compositions comprising the compounds of the invention for each of the aforementioned routes of administration will be apparent to the skilled artisan. For example, one embodiment of the invention provides for pharmaceutical compositions including a pharmaceutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula(I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

Synthesis of 2-(2,6-Dichlorophenylamino)-6,6-dimethyl-1H,6H-imidazo[4,5-h]isoquinoline-7,9-dione

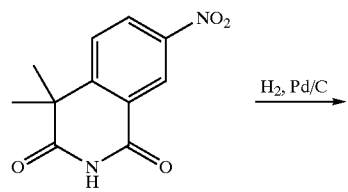

4,4-Dimethyl-7-nitro-2H,4H-isoquinoline-1,3-dione, prepared as described in U.S. Pat. No. 4,666,923 (1987), (1.0 g, 4.5 mmol) in methanol (50 mL) was hydrogenated over 10% Pd/C (30 mg) at 50 psi for 1.5 h. The catalyst was removed by filtration and the solvent removed to give 8-amino-4,4-dimethyl-2H,4H-isoquinoline-1,3-dione (0.90 g, 98%).

The above amine (1.5 g, 7.35 mmol) was stirred in acetic anhydride (9 mL) at room temperature for 3 h, then poured on to ice. The precipitate was filtered, washed with water and dried to give 7-acetamido-4,4-dimethyl-2H,4H-isoquinoline-1,3-dione (1.55 g, 86%)

The above amide was converted to 7-acetamido-4,4-dimethyl-8-nitro-2H,4H-isoquinoline-1,3-dione as described in U.S. Pat. No. 4,176,184 (1979).

7-Acetamido-4,4-dimethyl-8-nitro-2H,4H-isoquinoline-1,3-dione (4.0 g, 13.7 mmol) was added to 90% $H_2SO_4$ and heated at 70° C. for 8 h. The cooled mixture was poured onto ice. The precipitate was collected, dissolved in ethyl acetate, washed with water, dried and evaporated to give 7-amino-4,4-dimethyl-8-nitro-2H,4H-isoquinoline-1,3-dione (3.38 g, 99%), mp 259–263° C.; MS (CI) 250 (MH+).

A solution of the above amine (1.5 g, 6.0 mmol) in methanol (50 mL) was hydrogenated over platinum oxide (30 mg) at 50 psi for 1.25 h. The mixture was filtered through diatomaceous earth and evaporated to provide 7,8-diamino-4,4-dimethyl-2H,4H-isoquinoline-1,3-dione. (1.31 g, 100%). MS (CI) 220 (MH+).

As described in Method A, 2,6-dichlorophenylisothiocyanate (1.16 g, 5.7 mmol) was added to a suspension of 7,8-diamino-4,4-dimethyl-2H,4H-isoquinoline-1,3-dione (1.31 g, 6.0 mmol) in ethyl acetate (40 mL) and the mixture stirred overnight. The solid was filtered and dried to yield the thiourea (1.55 g, 61%). mp >300° C.; MS (CI) 423, 425 (MH+). A solution of the thiourea (2.23 g, 5.28 mmol) in THF (50 mL) and dicyclohexylcarbodiimide (1.11 g, 5.4 mmol) was heated under reflux with stirring for 4 h. The cooled solution was stirred overnight, filtered, and the crystals washed with $CH_2Cl_2$ to give the title compound (1.20 g). The filtrate was evaporated and triturated with $CH_2Cl_2$ to give more product (0.7 g, 93% combined yield), mp 290–292° C.; MS (EI) 388, 390 (M+).

Example 2

Synthesis of 2-(2,6-Dichlorophenylamino)-6,6-dimethyl-7,8-dihydro-1H,6H-imidazo[4,5-h]isoquinoline -9-one

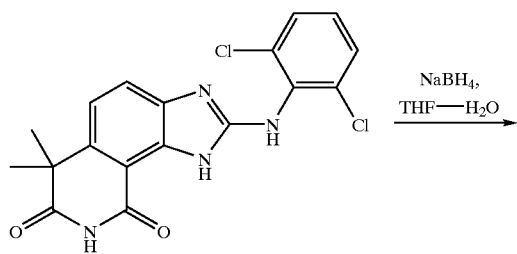

1

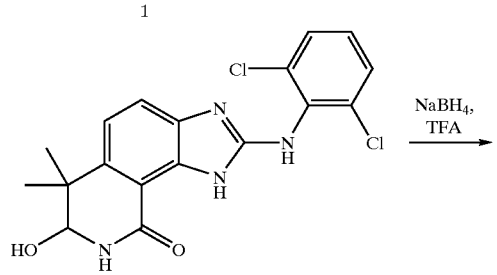

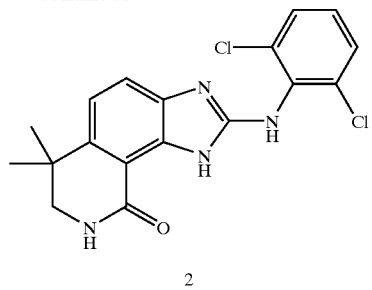

2

To a solution of the product of Example 1 (90 mg, 0.23 mmol) in THF (5 mL) was added $NaBH_4$ (90 mg, 2.3 mmol) followed by water (4 drops). The reaction mixture was stirred at ambient temperature for 1 h. Subsequently, 1N HCl (5 mL) was added dropwise and the reaction mixture was stirred an additional 15 minutes, neutralized with $NaHCO_3$ and extracted with EtOAc. The extract was washed with brine, dried and evaporated yielding the alcohol 2-(2,6-dichlorophenylamino)-6,6-dimethyl-7-hydroxy-7,8-dihydro-1H,6H-imidazo[4,5-h]isoquinoline-9-one (90 mg 99%). This intermediate was used immediately due to its instability. It was characterized as the methyl ether, which was prepared by dissolving the product in MeOH/HCl and stirring for several hours. After evaporation, the residue was partitioned between EtOAc/aq $NaHCO_3$. The organic phase was washed with brine, dried and evaporated to the methyl ether derivative, mp 278–280° C.(dec); MS (ES) 405 (MH+).

The alcohol from above (100 mg, 0.26 mmol) was dissolved in TFA (2 mL) and this solution was subsequently added to a solution of sodium tristrifluoroacetoxyborohydride (generated in-situ from 160 mg, 4.2 mmol of sodium borohydride and 3 mL TFA) at 0° C. The reaction mixture was stirred at ambient temperature for 4 h, the solvent was evaporated, the residue was triturated with water and the resultant mixture was neutralized with $NaHCO_3$ and filtered yielding the title compound (85 mg, 92%). This product was purified by flash chromatography on $SiO_2$ using 4% MeOH/$CH_2Cl_2$ as eluant and recrystallization from EtOAc, mp 287–290° C.; MS (CI) 375 (MH$^+$).

Example 3a

Synthesis of 2-(2,6-Dichlorophenylamino)-6,7-dimethyl-1,8-dihydro-imidazo[4,5-h]isoquinoline-9-one

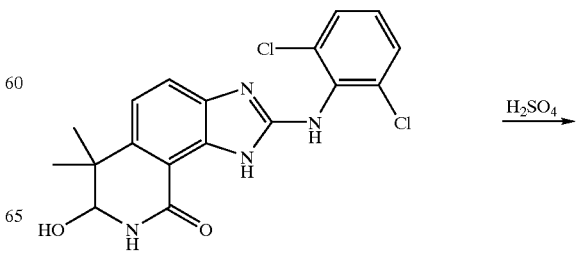

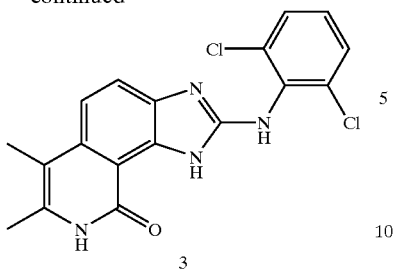

2-(2,6-Dichlorophenylamino)-6,6-dimethyl-7-hydroxy-7,8-dihydro-1H,6H-imidazo[4,5-h]isoquinoline-9-one (from Example 2) (45 mg, 0.11 mmol) was suspended in conc. H$_2$SO$_4$ (1 mL) and the resultant mixture was stirred at ambient temperature for 15 min. The solution was poured over ice, neutralized with NaHCO$_3$ and filtered. The filtrate was triturated with water (10 mL) and centrifuged. The liquid was decanted, and the residual solid was triturated with methanol and centrifuged. The supernatant was decanted and the residue dried to give the title compound (35 mg, 84%). Mp >300° C.; MS (ES) 373 (MH$^+$).

Example 3b

Synthesis of 2-(2,6-Dichlorophenylamino)-6,7-dimethyl-1,8-dihydro-imidazo[4,5-h]isoquinoline-9-one (Method C)

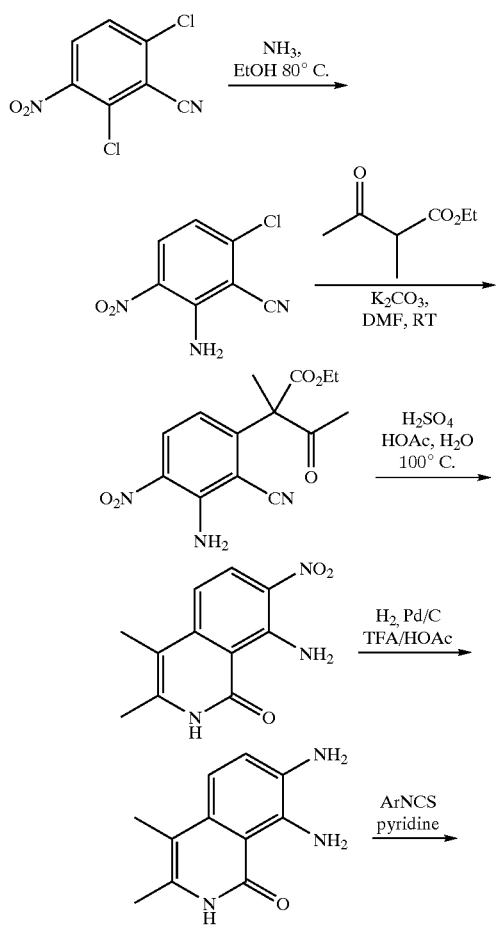

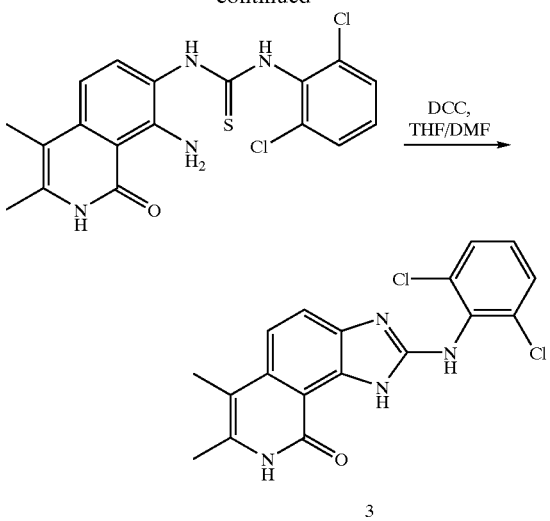

A 500 mL pressure flask was charged with 2,6-dichloro-3-nitrobenzonitrile (30.0 g, 138 mmol) and a 5.1 M solution of ammonia in EtOH (170 mL). The flask was sealed and heated in an oil bath at 80° C. with stirring for 1.5 h. The cooled solution was filtered, the crystals washed with water and dried to yield 2-amino-6-chloro-3-nitrobenzonitrile (18.4 g, 68%), mp 181–184° C.; MS (ES$^-$) 196, 198 (M-H$^-$).

To a solution of 2-amino-6-chloro-3-nitrobenzonitrile (1.97 g, 10 mmol) and ethyl 2-methylacetoacetate (3.6 g, 25 mmol) in DMF (10 mL) was added finely powdered K$_2$CO$_3$, and the mixture stirred vigorously for 24 h. The deep red mixture was diluted with EtOAc and washed in turn with 2 M HCl, water and brine. The residue after evaporation was purified by flash chromatography in hexane/EtOAc 3:1 to yield 2-(3-amino-2-cyano-4-nitrophenyl)-2-methyl-3-oxobutyric acid ethyl ester as an oil (1.39 g, 46%), MS (NH$_3$ CI) 323 (M+NH$_4$$^+$), 293 (M+NH$_4$–NO$^+$).

The ester from above (1.39 g, 4.56 mmol) was added to a mixture of acetic acid (20 mL), H$_2$SO$_4$ (3 mL) and water (2 mL), and the solution heated at 100° C. for 3 h. The cooled solution was diluted with water (30 mL), the precipitate was collected, washed with water and MeOH and dried to give 8-amino-3,4-dimethyl-7-nitro-2H-isoquinolin-1-one (0.76 g, 72%). mp >300° C.

A solution of the amino isoquinolin-1-one from above (0.20 g, 0.86 mmol) in trifluoroacetic acid (11 mL) and acetic acid (7 mL) was hydrogenated over 10% palladium on carbon (21 mg) at 50 psi for 2 h. The solution was filtered through diatomaceous earth, washing with acetic acid, and the filtrate evaporated to give 7,8-diamino-3,4-dimethyl-2H-isoquinolin-1-one ditrifluoroacetate salt (310 mg, 83%).

A suspension of the diamino isoquinolin-1-one ditrifluoroacetate salt from above (1.15 g, 2.67 mmol) and 2,6-dichlorophenylisothiocyanate (0.60 g, 2.93 mmol) in pyridine (16 mL) was stirred for 18 h at room temperature (Method A). The solution was diluted with toluene and evaporated, and remaining pyridine removed with a toluene azeotrope. The residue was triturated with EtOAc to give the thiourea (1.17 g). A portion of this material (0.50 g, 1.23 mmol) and dicyclohexylcarbodiimide (0.375 g, 1.84 mmol) were heated together in DMF under argon at 80° C. for 4 h. The cooled solution was evaporated and triturated first with cold MeOH, then with boiling MeOH, to leave the title compound as a light tan solid, (0.309 g, 73%), identical with the sample obtained in Example 3a.

Example 4

Synthesis of 2-(2,6-Dichlorophenylamino)-1,6,7-trimethyl-1,8-dihydro-imidazo[4,5-h]isoquinoline-9-one

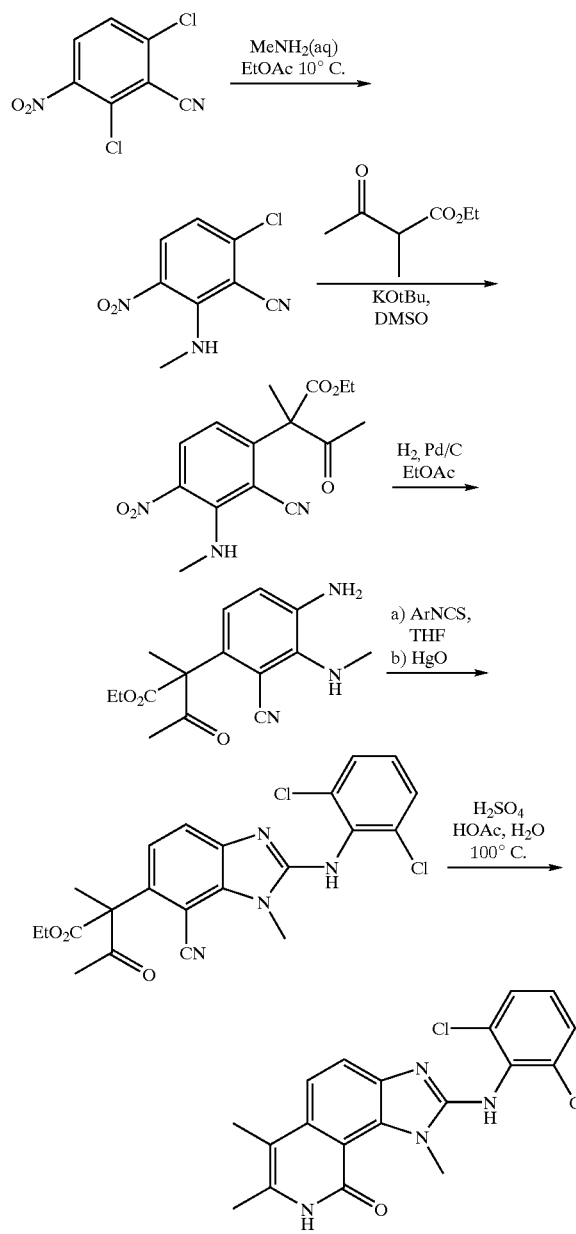

A solution of 2,6-dichloro-3-nitrobenzonitrile (98.7 g, 0.455 mol) in EtOAc (910 mL) was cooled to 5° C. 40% Aqueous methylamine (79.5 mL, 1.14 mol) was added with vigorous mechanical stirring, keeping the temperature at 10–15° C. After addition was complete, stirring was continued for 3 h at the same temperature. More methylamine (16 mL, 0.23 mol) was added, and the mixture stirred for a further 1.5 h at room temperature. Water (300 mL) was added, followed by hexane (450 mL). The mixture was stirred for 15 min, filtered, and the solid washed with water and MeOH, to give 6-chloro-2-methylamino-3-nitrobenzonitrile (80.3 g, 83%), mp 167–170° C.

To a stirred solution of potassium t-butoxide (24.3 g, 206 mmol) in DMSO (500 mL) was added ethyl 2-methylacetoacetate (34.3 g, 233 mmol), dropwise over 5 min. The temperature rose to 30° C. 6-Chloro-2-methylamino-3-nitrobenzonitrile (43.6 g, 190 mmol) was added in portions over 15 min. The temperature rose to 40° C. The solution was stirred for 1 h with no external heating or cooling. The mixture was poured into 10% $NH_4Cl$ (500 mL), and extracted with EtOAc (2×500 mL). The combined extracts were washed with water (2×250 mL) and brine, and evaporated. MeOH (200 mL) was added to the residue and stirred for 1.5 h. The yellow solid was filtered, washed with cold MeOH (25 mL) and dried to give 2-(2-cyano-3-methylamino-4-nitrophenyl)-2-methyl-3-oxobutyric acid ethyl ester (36.2 g, 60%), mp 87–91 ° C.

A solution of the above ester (10.5 g, 32.5 mmol) in EtOAc (130 mL) was hydrogenated over 10% palladium on carbon (0.5 g) at 50 psi for 24 h. The catalyst was removed by filtration through diatomaceous earth, and the filtrate was evaporated. A mixture of EtOAc/hexane (1:1, 10 mL) was added to the residue and the resulting mixture was stirred for 0.5 h. The crystals were filtered and washed with hexane to give 2-(4-amino-2-cyano-3-methylaminophenyl)-2-methyl-3-oxobutyric acid ethyl ester (7.74 g, 81%), mp 118–123° C.

A solution of the amino ester from above (7.7 g, 26.6 mmol) and 2,6-dichlorophenylisothiocyanate (5.43 g, 26.6 mmol) in THF (150 mL) was stirred at room temperature for 5 h. Mercuric oxide (6.34 g, 29.3 mmol) was then added in one portion, and stirring continued overnight. The mixture was filtered through diatomaceous earth, washing well with THF. The filtrate was evaporated, and the residue triturated with ether to give 2-[4-cyano-2-(2,6-dichlorophenylamino)-3-methyl-3H-benzimiazol-5-yl]-2-methyl-3-oxobutyric acid ethyl ester as an off-white solid (7.7 g, 63%).

To a stirred mixture of conc. $H_2SO_4$ (40 mL), HOAc (40 mL) and water (40 mL) at 60° C. was added 2-[4-cyano-2-(2,6-dichlorophenylamino)-3-methyl-3H-benzimiazol-5-yl]-2-methyl-3-oxobutyric acid ethyl ester (7.4 g, 16 mmol) in one portion. The solution was heated at 100° C. for 2.5 h, then stirred overnight at room temperature. The reaction mixture was poured onto ice, and neutralized with conc. $NH_4OH$, with ice cooling. The precipitate was filtered and washed well with water. The solid was slurried in MeOH, stirred well, filtered, washed with MeOH until washings were colorless, and dried. The title compound was obtained as a grey solid (5.48 g, 88%), mp >300° C.; MS ($NH_3$ CI) 387, 389 (MH+).

Example 5

Synthesis of 2-(2,6-Dichlorophenylamino)-6,6-dimethyl-6H-thiazolo[4,5-h]isoquinoline-7,9-dione (Method B)

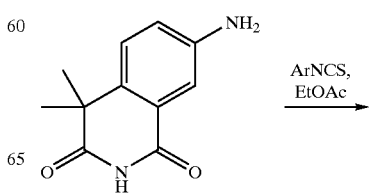

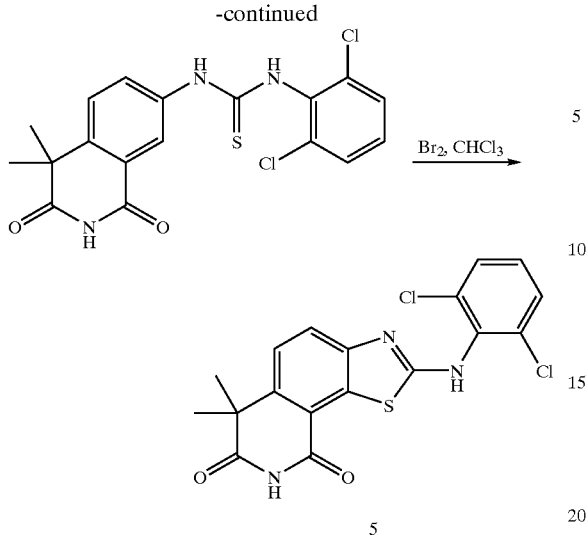

To a suspension of 7-amino-4,4-dimethyl-2H,4H-isoquinoline-1,3-dione (204 mg, 1 mmol) in EtOAc (25 mL) was added 2,6-dichlorophenylisothiocyanate (223 mg, 1.1 mmol) in three portions, and the mixture was stirred overnight. The solid was filtered and dried to yield the thiourea (380 mg, 93%), mp 142–144° C.; MS (CI) 408(MH$^+$). To a suspension of the thiourea (140 mg, 0.34 mmol) in CHCl$_3$ (20 mL) was added Br$_2$ (60 mg, 0.37 mmol) in CHCl$_3$ (2 mL) dropwise. The solution was heated to reflux for 1 h. The solvent was evaporated and the residue triturated with saturated NaHCO$_3$ (50 mL). The solid was filtered, washed with water, and dried, to yield the title compound (114 mg, 82%), mp >300° C.; MS (CI) 406(MH+).

Example 6

Synthesis of 2-(2,6-Dichlorophenylamino)-6,7-dimethyl-8H-thiazolo[4,5-h]isoquinoline-9-one (Method B)

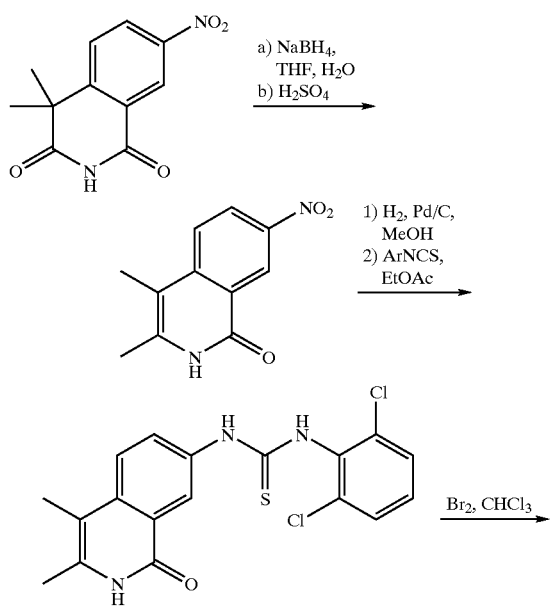

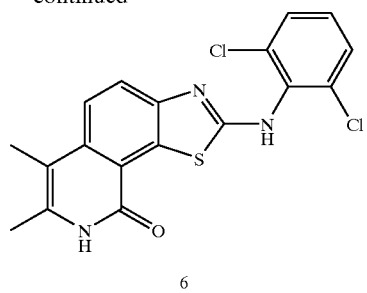

To a solution of 7-nitro-4,4-dimethyl-2H,4H-isoquinoline-1,3-dione from Example 1 (1.0 g, 4.3 mmol) in THF (50 mL) was added NaBH$_4$ (330 mg, 8.7 mmol) followed by water (10 drops). The reaction mixture was stirred at room temperature for 2.5 h, cooled in an ice bath and treated with 1N HCl until a pale yellow color was maintained. After 10 min. the reaction mixture was neutralized with saturated NaHCO$_3$ and extracted with EtOAc. The extract was washed with brine, dried and evaporated to the alcohol, which was immediately taken up in conc. H$_2$SO$_4$ (8 mL). This mixture was stirred until completely dissolved (10 min.), poured over ice, neutralized with 10% NH$_4$OH, allowed to stand several hours, filtered and dried to yield 3,4-dimethyl-7-nitro-isoquinoline-1-one (780 mg, 83%). MS (CI) 219(MH$^+$).

A solution of 3,4-dimethyl-7-nitro-isoquinoline-1-one (750 mg, 3.4 mmol) in MeOH (250 mL) was hydrogenated over Pd/C (25 mg) at 60 psi for 24 h. The reaction mixture was filtered through diatomaceous earth, washing well with MeOH. Evaporation of the filtrate provided the amine (554 mg, 85%) which was immediately dissolved in EtOAc (60 mL) and treated with 2,6-dichlorophenylisothiocyanate (663 mg, 3.3 mmol). The mixture was stirred at ambient temperature for 48 h, refluxed for 4 h and stirred at ambient temperature an additional 72 h. The thiourea was filtered and washed with EtOAc (850 mg, 74%) mp 220° C. (dec). A portion of the thiourea (490 mg, 1.25 mmol) was suspended in CHCl$_3$ (50 mL) and treated with a solution of Br$_2$ (200 mg, 1.25 mmol) in CHCl$_3$ (5 mL), and the resulting mixture was refluxed for 1 h. The solvent was evaporated, the residue was suspended in a saturated solution of NaHSO$_3$, filtered, then treated analogously with a saturated solution of NaHCO$_3$. Purification by silica column chromatography (0 to 5% MeOH in CH$_2$Cl$_2$ eluant) yielded the title compound (281 mg, 58%), mp >300° C., MS (CI) 390 (MH$^+$).

Example 7

Synthesis of 2-(2,6-Dichlorophenylamino)-1,7-dimethyl-6-(2-morpholin-4-yl-2-oxoethyl)-1,8-dihydro-imidazo[4,5-h]isoquinoline-9one

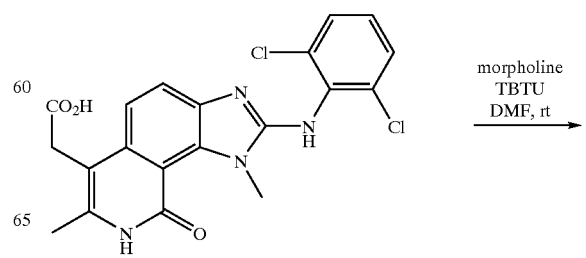

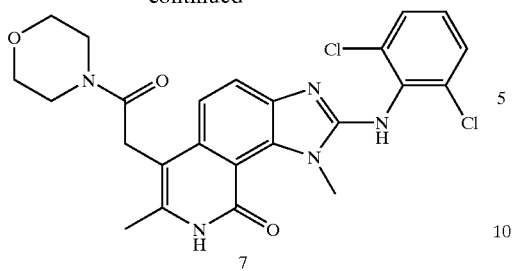

To a solution of 2-(2,6-dichlorophenylamino)-1,7-dimethyl-9-oxo-1,8-dihydro-imidazo[4,5-h]isoquinolin-6-yl acetic acid (prepared using Methods C and A) (1.0 g, 2.3 mmol) in DMF (7 mL) was added O-benzotriazol-1-yl-N,N,N',N'-tetramethyluronium tetrafluoroborate (TBTU) (0.82 g, 2.6 mmol) and morpholine (0.24 mL, 2.8 mmol), and the mixture stirred 18 h at room temperature. Ice water was added, the precipitate collected, washed with water and dried to give the title compound, 0.97 g, 84%, mp >300° C.; MS (ES) 500, 502 (MH+).

Example 8

Synthesis of 2-(2,6-Dichlorophenylamino)-1,7-dimethyl-6-(2-morpholin-4-yl-ethyl)-1,8-dihydro-imidazo[4,5-h]isoquinoline-9-one

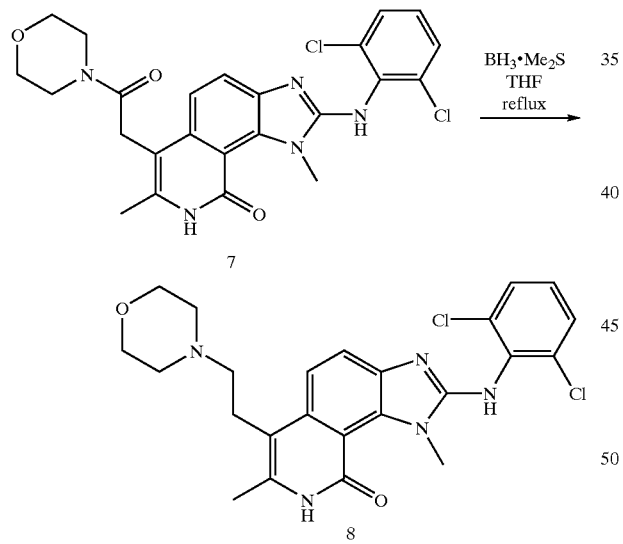

A stirred suspension of the product of Example 7 (85 mg, 0.17 mmol) in THF (9 mL) was heated to reflux and borane-methylsulfide (0.09 mL, 0.9 mmol) added. Stirring was continued for 3.5 h at reflux and overnight at room temperature. 6M HCl was added and the solution stirred for 2 h. The solution was applied to a Varian SCX column, washed with MeOH/CH$_2$Cl$_2$ 50:50, then the product eluted with MeOH/CH$_2$Cl$_2$/NH$_4$OH 50:50:1. The product was further purified on a silica column eluting with CH$_2$Cl$_2$/MeOH 98:2 to give the title compound 32 mg, 39%, mp 285–290° C.; MS (ES) 486, 488 (MH+).

Example 9

Synthesis of 2-(2,6-Dichlorophenylamino)-1,7-dimethyl-9-oxo-1,8-dihydro-imidazo[4,5-h]isoquinolin-6-yl acetic acid ethyl ester

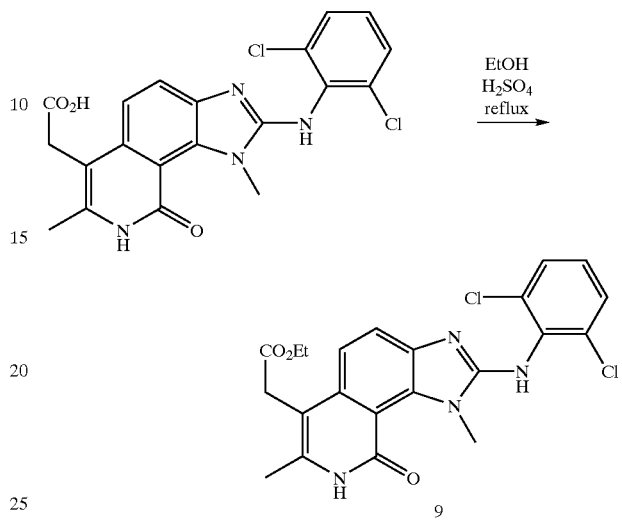

Prepared from 2-(2,6-dichlorophenylamino)-1,7-dimethyl-9-oxo-1,8-dihydro-imidazo[4,5-h]isoquinolin-6-yl acetic acid by refluxing in ethanol and H$_2$SO$_4$. Mp 280–285° C. (dec); MS(CI) 459, 461 (MH+).

Example 10

Synthesis 2-(2,6-Dichlorophenylamino)-1,7-dimethyl-6-(2-hydroxyethyl)-1,8-dihydro-imidazo[4,5-h]-isoquinoline-9-one

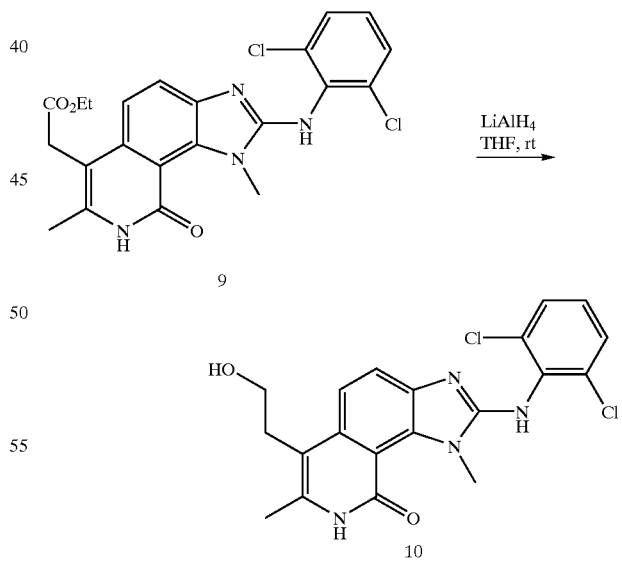

To a stirred solution of the product of Example 9 (25 mg, 0.05 mmol), in THF (2 mL), under nitrogen, was added a solution of lithium aluminum hydride (1M in THF, 0.25 mL, 0.25 mmol). The mixture was stirred for 30min at room temperature. Ethyl acetate was added, followed by water, and then acidified with 1N HCl. The whole mixture was applied to a Varian SCX cartridge, and washed in turn with 1N HCl, water, acetone, MeOH, and MeOH/CH₂Cl₂ (1:1). The product was then eluted with MeOH/CH₂Cl₂/NH₄OH (49:49:2). Evaporation of the eluent gave the title compound (15 mg, 72%). Mp >300° C.; MS(ES) 417, 419 (MH+).

Example 11

Synthesis of 2-(2,6-Dichlorophenylamino)-1,6-dimethyl-9-oxo-8,9-dihydro-1H-imidazo[4,5-h]isoquinoline-7-carbaldehyde The method described below is useful for preparing intermediate compounds such as 11, which possess an aldehyde moiety at the 7-position.

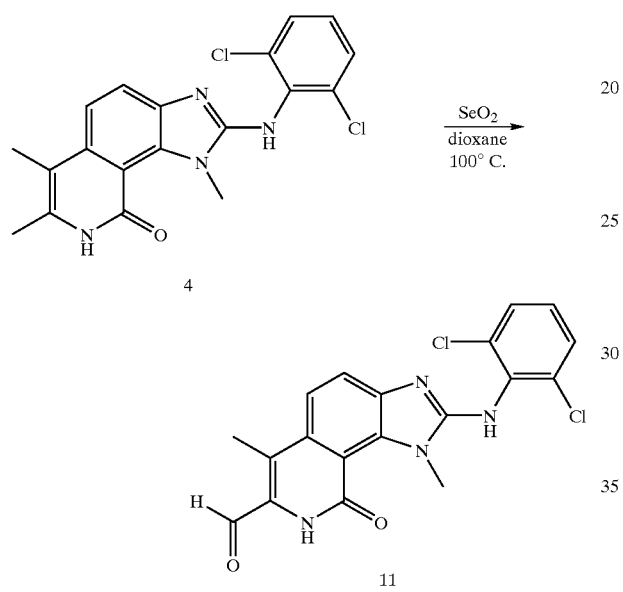

To a suspension of the product from Example 4 (521 mg, 1.3 mmol) in dioxane (30 mL) was added selenium dioxide (430 mg, 3.9 mmol) and the mixture was heated at 100° C. for 5 h. The reaction was then cooled to room temperature, filtered through diatomaceous earth with 10% MeOH—CH₂Cl₂ and then concentrated in vacuo. The crude material was triturated with CH₂Cl₂ to provide the title compound (476 mg, 92%), mp: >300° C.; MS (CI) 401, 403 (MH+).

Example 12

Synthesis of 3-[2-(2,6-Dichlorophenylamino)-1,6-dimethyl-9-oxo-8,9-dihydro-1H-imidazo[4,5-h]isoquinolin-7-yl]acid methyl ester

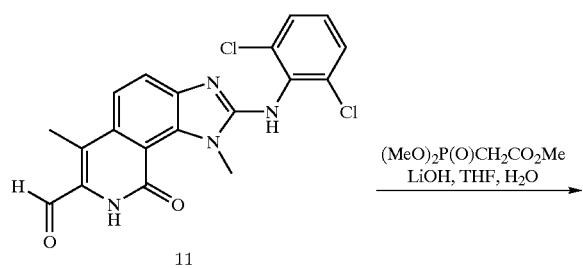

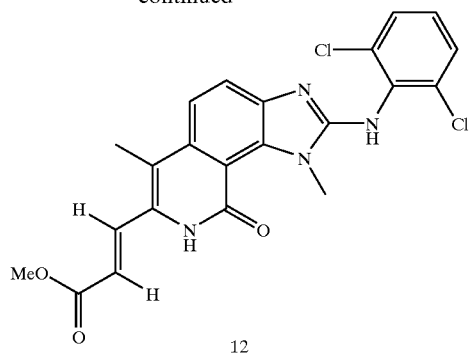

To a suspension of the product of Example 11 (329 mg, 0.82 mmol) in THF (5 mL) was added sequentially, trimethyl phosphonoacetate (164 mg, 0.90 mmol), lithium hydroxide monohydrate (76 mg, 1.8 mmol) and water (0.9 mL). The blood red solution was stirred for 2 h, quenched with water, and the resulting solid was collected and dried in vacuo. Column chromatography (5% MeOH—CH₂Cl₂) provided the title compound (300 mg, 80%), mp >300° C.; MS (ES) 457, 459 (MH+).

Example 13

Synthesis of 3-[2-(2,6-Dichlorophenylamino)-1,6-dimethyl-9-oxo-8,9-dihydro-1H-imidazo[4,5-h]isoquinolin-7-yl]-acid methyl ester

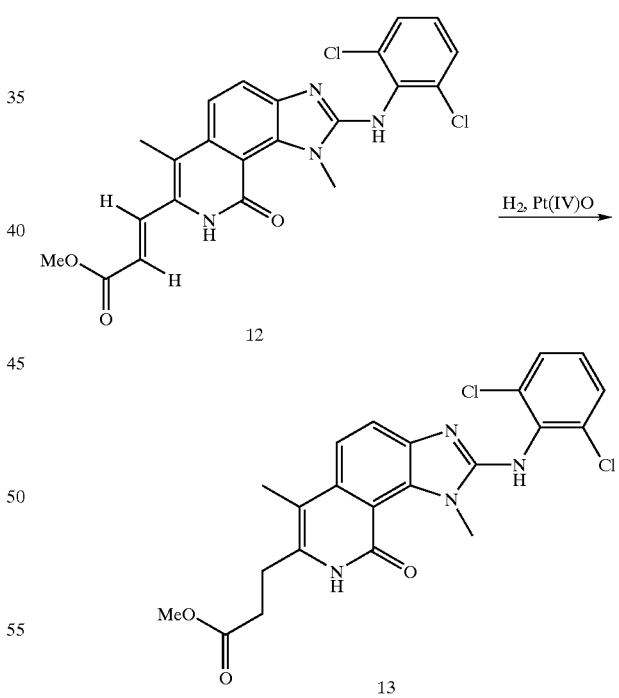

To a solution of the product of Example 12 (30 mg, 0.06 mmol) in EtOH (3 mL) and AcOH (4 mL) in a Parr reactor was added PtO₂ (2 mg, 0.007 mmol). The Parr reactor was charged with 50 psi of H₂ and shaken for 12 h. The crude reaction was filtered through diatomaceous earth with EtOH and concentrated in vacuo. Column chromatography (2% MeOH—CH₂Cl₂) provided the title compound (9 mg, 30%), mp 268° C.(dec); MS(ES) 459, 461 (MH+).

Example 14

Synthesis of 2-(2,6-Dichlorophenylamino)-1,6-dimethyl-7-(3-hydroxy-propen-1-yl)-1,8-dihydro-imidazo[4,5-h]isoquinolin-9-one

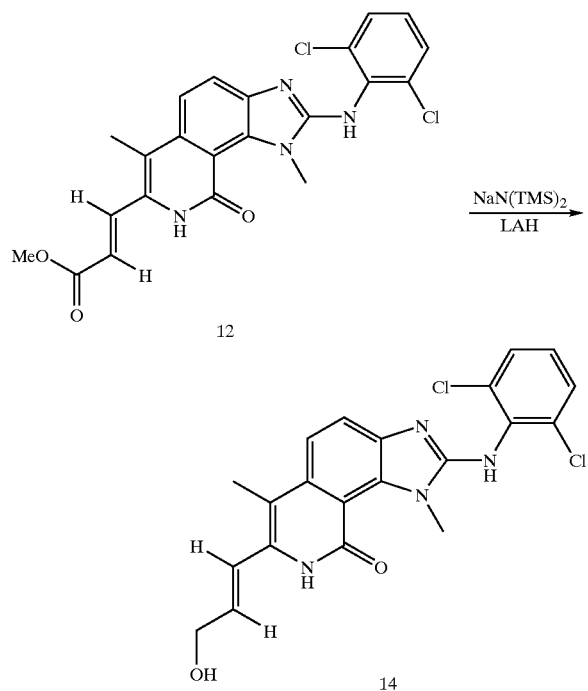

A suspension of the product of Example 12 (100 mg, 0.22 mmol) in THF (7 mL) was cooled to −78° C. Sodium bis(trimethylsilyl)amide (1M in THF, 0.44 mmol) was added dropwise. The bright red solution was warmed to 0° C. for 15 minutes, then lithium aluminum hydride (1M in THF, 2.6 mmol) was added and the orange solution was warmed to room temperature for 0.5 h. The mixture was cooled to 0° C., quenched with saturated ammonium chloride and extracted with ethyl acetate. Column chromatography (3–6% MeOH—$CH_2Cl_2$) provided the title compound (32 mg, 34%), mp 298–300° C.; MS(ES) 429, 431 (MH+).

Example 15

Synthesis of 2-(2,6-Dichlorophenylamino)-1,6-dimethyl-7-vinyl-1,8-dihydro-imidazo[4,5-h]isoquinoline-9-one

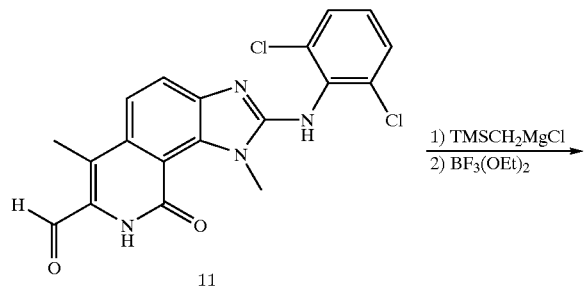

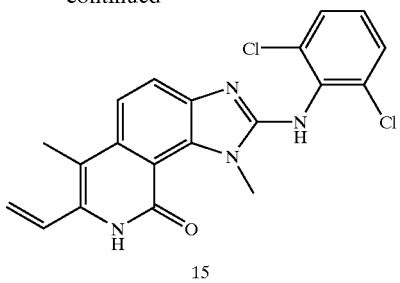

To a suspension of the product of Example 11 (100 mg, 0.25 mmol) in THF (5 mL) was added trimethylsilylmethyl magnesium chloride (2 mL, 2 mmol) at −78° C. The reaction was warmed to room temperature for 1 h, then cooled to 0° C. and quenched with water and extracted with ethyl acetate to provide the silyl alcohol (85 mg, 70%). The crude silyl alcohol was suspended in $CH_2Cl_2$ and cooled to 0° C. Borontrifluoride etherate (42 μL, 0.32 mmol) was added and the slurry was warmed to room temperature for 1 h. The reaction was quenched with water, and the $CH_2Cl_2$ was removed in vacuo. Collection of the resulting solid followed by $CH_2Cl_2$ trituration provided the title compound (17 mg, 61%), mp >300° C.; MS(Es) 399, 401(MH+).

Example 16

Synthesis of 2-(2,6-Dichlorophenylamino)-1,6-dimethyl-7-(1-hydroxyprop-2-en-1-yl)-1,8-dihydro-imidazo[4,5-h]isoquinolin-9-one

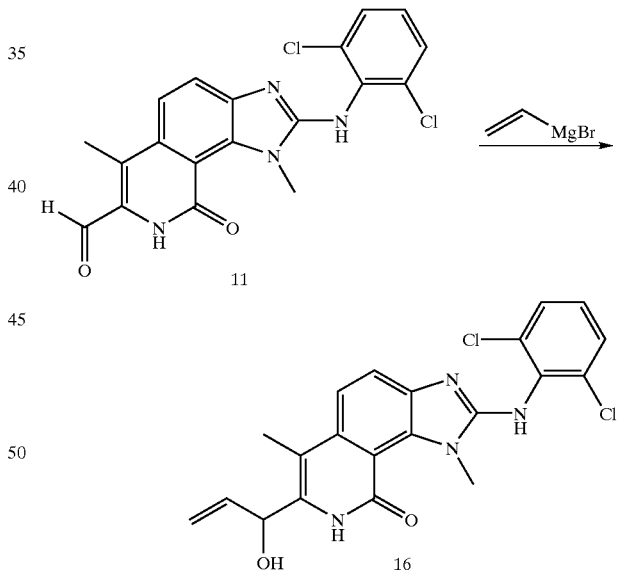

A suspension of 2-(2,6-dichlorophenylamino)-1,6-dimethyl-9-oxo-8,9-dihydro-1H-imidazo[4,5-h]isoquinoline-7-carbaldehyde (2) (100 mg, 0.25 mmol) in THF (3 ml) was cooled to −78° C. Vinylmagnesium bromide (1M in THF, 2.0 mmol) was added dropwise, and the brown suspension was warmed gradually to −10° C. over 2 h. The solution was quenched with saturated ammonium chloride and extracted with ethyl acetate, and concentrated in vacuo to provide the title compound, which was used in the next step without purification, mp 235–236° C., MS (ES) 429 (MH+).

Example 17

Synthesis of 2-(2,6-Dichlorophenylamino)-7-(1-acetoxyprop-3-en-1-yl)-1,6-dimethyl-1,8-dihydro-imidazo[4,5-h]isoquinolin-9-one

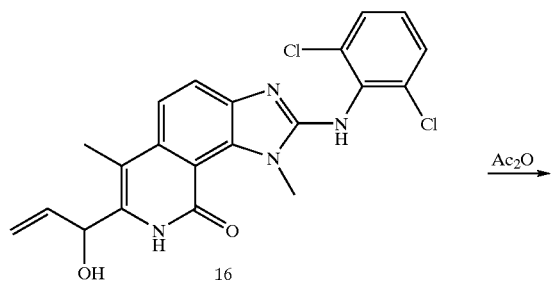

To a solution of the product of Example 16 (106 mg, 0.25 mmol) in THF (1 ml) was added acetic anhydride (1 ml). Triethylamine (35 μL, 0.25 mmol) was added, and the reaction was stirred for 14 h, then concentrated in vacuo. Column chromatography (2% MeOH—CH$_2$Cl$_2$) provided the title compound (85 mg, 79%), mp 169–171° C.; MS (ES) 471 (MH+).

Example 18

Synthesis of 2-(2,6-Dichlorophenylamino)-1,6-dimethyl-7-(3-morpholin-4-yl-propen-1-yl)-1,8-dihydro-imidazo[4,5-h]-isoquinolin-9-one

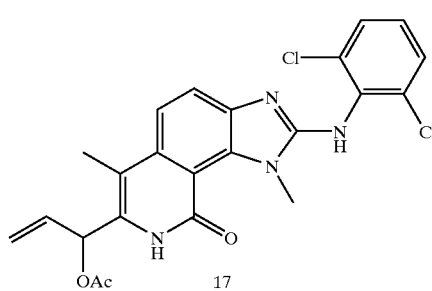

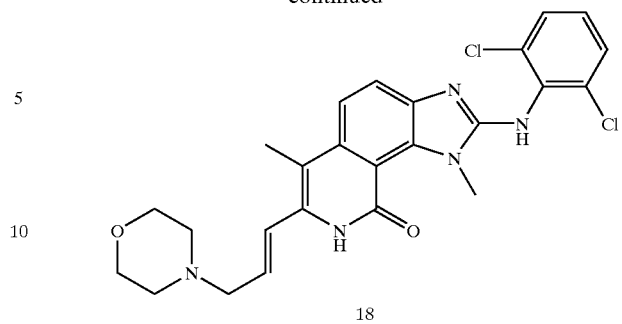

Tris(dibenzylideneacetone) dipalladium(0) (1.8 mg, 0.002 mmol) and triphenylphosphine (1.6 mg, 0.006 mmol) were stirred in THF (0.5 ml) for 20 min under inert atmosphere until the red solution turned yellow. To this solution was added sequentially, the product of Example 17 (20 mg, 0.04 mmol) in THF (0.5 ml), triethylamine (17 μL, 0.12 mmol) and morpholine (11 μL, 0.12 mmol). The solution was stirred 14 h, then concentrated to an oil. Column chromatography (10% MeOH—CH$_2$Cl$_2$) provided the title compound (10 mg, 50%), mp 175–177° C.; MS (ES) 498 (MH+).

Example 19

Synthesis of 7-Benzylaminomethyl-2-(2,6-dichlorophenylamino)-1,6-dimethyl-1,8-dihydro-imidazo[4,5-h]-isoquinolin-9-one

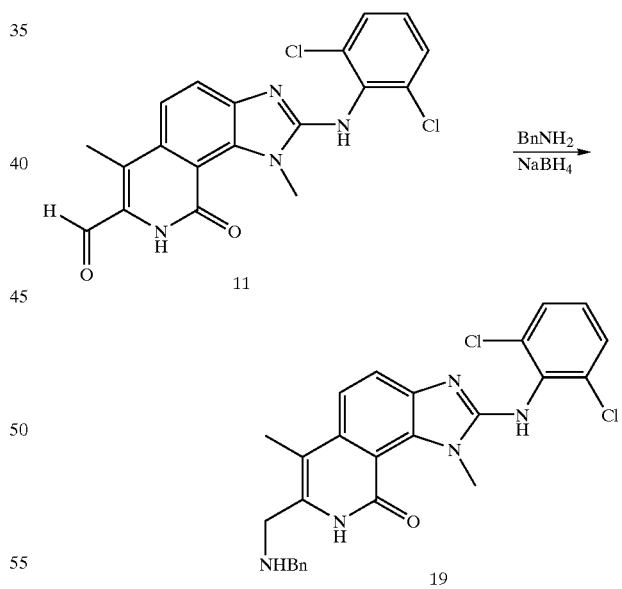

To a suspension of the product of Example 11 (50 mg, 0.12 mmol) in THF (4 mL) was lo added benzylamine (54 mg, 0.50 mmol). The reaction was stirred for 12 h, then concentrated in vacuo. The crude imine was suspended in MeOH (2 mL), sodium borohydride (21 mg, 0.55 mmol) was added, and the reaction was stirred for 3 h. The reaction was quenched with water, and the resulting solid was collected and dried to provide the title compound (11 mg, 39%), mp 231–234° C.; MS (ES) 492(MH+).

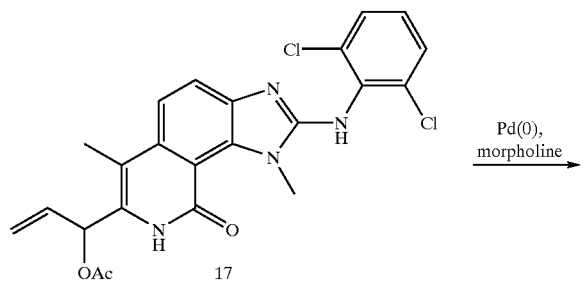

Example 20

Synthesis of 2-(2,6-Dichlorophenylamino)-1,6-dimethyl-7-oxazol-5-yl-1,8-dihydro-imidazo[4,5-h]isoquinolin-9-one

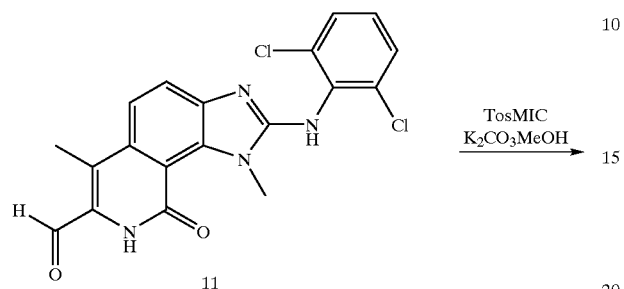

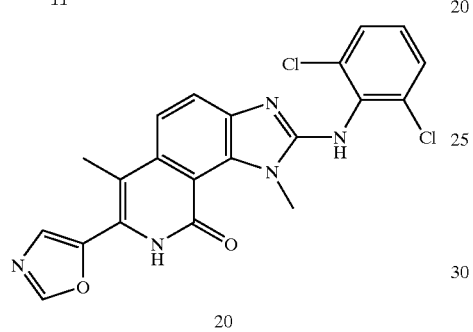

A suspension of the product of Example 11 (40 mg, 0.10 mmol), tosylmethyl isocyanide (21 mg, 0.11 mmol) and K₂CO₃ in methanol (2 mL) was heated to 40° C. for 90 min. The mixture was diluted with water (3 mL) and the solid collected by filtration to obtain the title compound (26 mg, 60%), mp >300° C.; MS (ES) 440, 442(MH+).

Example 21

Synthesis of 2-(2,6-Dichlorophenylamino)-1,6-dimethyl-7-(3-methyl-3H-imidazol-4-yl)-1,8-dihydro-imidazo[4,5-h]isoquinolin-9-one

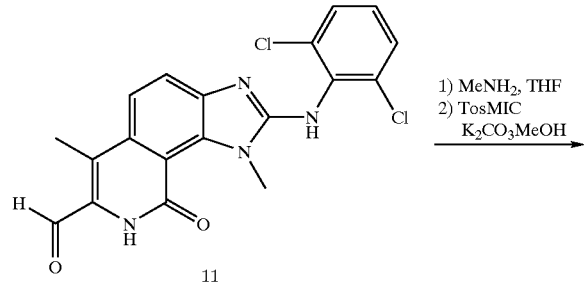

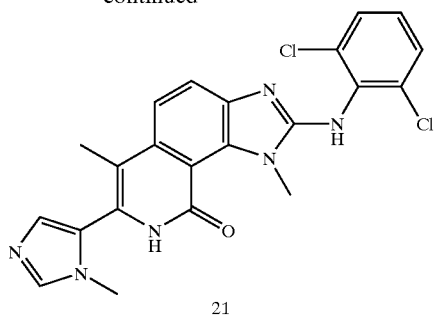

A suspension of the product of Example 11 (50 mg, 0.13 mmol) and methylamine (2M in THF, 2 mL, 4 mmol) in dry THF (2 mL) was stirred at room temperature for 12 h. The THF was evaporated and the resulting imine was mixed with tosylmethyl isocyanide (27 mg, 0.14 mmol), K₂CO₃ (31 mg, 0.23 mmol) and dry DMSO (2 mL). This suspension was stirred for five days at room temperature. Water (5 mL) was added and the precipitate collected by filtration. Flash chromatography in CH₂Cl₂/MeOH (98:2) gave the title compound (8 mg, 14%), mp >300° C.; MS(ES) 453, 455 (MH+).

Example 22

Synthesis of 2-(2,6-Dichlorophenylamino)-1,6,7-trimethyl-4-vinyl-1,8-dihydro-imidazo[4,5-h]isoquinoline-9-one

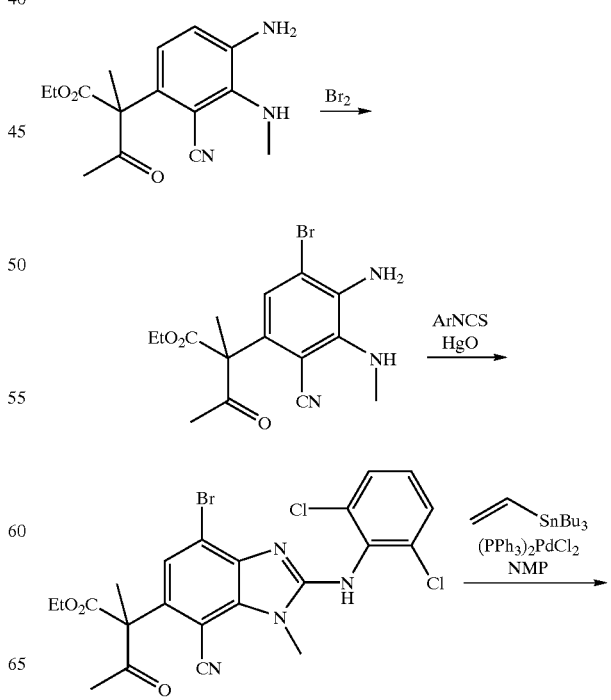

-continued

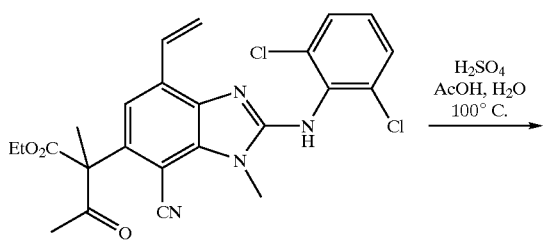

(0.6 mL) was heated at 100° C. for 2 h. The resulting mixture was cooled to room temperature and diluted with water (10 mL). The solution was adjusted to pH 8 with 10% NaOH solution. The precipitated brown solid was filtered and purified by flash chromatography in CH₂Cl₂/MeOH 30:1 to yield the title compound (15 mg, 27%), mp decomp. above 250° C.; MS (CI) 413(MH+).

Example 23

Synthesis of 2-(2,6-Dichlorophenylamino)-1,6,7-trimethyl-9-oxo-1,8-dihydro-imidazo[4,5-h]isoquinoline-4-carbaldehyde

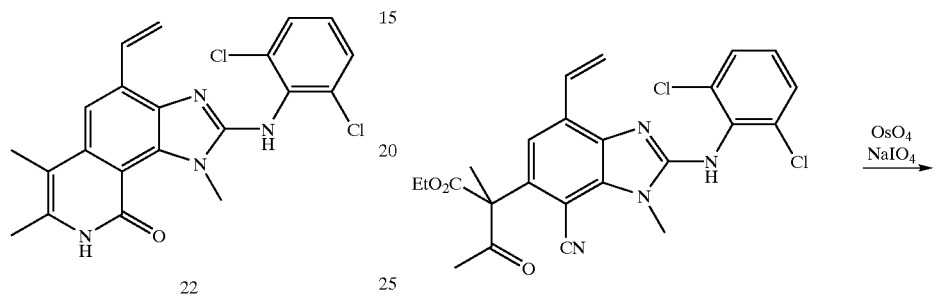

To a solution of 2-(4-amino-2-cyano-3-methylaminophenyl)-2-methyl-3-oxobutyric acid ethyl ester from Example 4 (9.02 g, 31.2 mmol) in CHCl₃ (90 mL) was added bromine (4.98 g, 31.2 mmol) dropwise at ambient temperature. After the addition of bromine, the reaction mixture was diluted with ethyl acetate (800 mL). This solution was washed successively with sat. NaHCO₃ solution and brine and dried. The residue after evaporation was purified by flash chromatography in hexanes/EtOAc 2:1 to yield 2-(4-amino-5-bromo-2-cyano-3-methylaminophenyl)-2-methyl-3-oxobutyric acid ethyl ester as an oil (6.06 g, 53%).

To a solution of the above ester (3.32 g, 9.02 mmol) in 1,4-dioxane (45 mL) was added 2,6-dichlorophenylisothiocyanate (2.02 g, 9.92 mmol) and mercuric oxide (2.54 g, 11.7 mmol) under nitrogen atmosphere. The resulting mixture was stirred and heated at 95° C. overnight. The reaction mixture was cooled to room temperature and filtered though a short pad of diatomaceous earth and SiO₂. The filtrate was concentrated and the residue was purified by flash chromatography in hexanes/EtOAc 2:1 to yield 2-[8-bromo-4-cyano-2-(2,6-dichlorophenylamino)-3-methyl-3H-benzimiazol-5-yl]-2-methyl-3-oxobutyric acid ethyl ester as a brown solid (3.44 g, 71%).

A mixture of the above bromo ester (600 mg, 1.11 mmol), (PPh₃)₂PdCl₂ (78 mg, 0.11 mmmol) and tributyl(vinyl)tin (0.49 mL, 1.67 mmol) in NMP (4 mL) was degassed and heated at 100° C. for 3 days under argon. The mixture was concentrated and the residue was purified by flash chromatography in hexanes/EtOAc 3:1 to yield 2-[4-cyano-2-(2,6-dichlorophenylamino)-3-methyl-8-vinyl-3H-benzimiazol-5-yl]-2-methyl-3-oxobutyric acid ethyl ester as an oil (530 mg, 98%).

A solution of the above keto ester (66 mg, 0.14 mmol) in a mixture of H₂SO₄ (0.6 mL), acetic acid (0.6 mL) and water A solution of 2-[4-cyano-2-(2,6-dichlorophenylamino)-3-methyl-8-vinyl-3H-benzimiazol-5-yl]-2-methyl-3-oxobutyric acid ethyl ester (see Example 22) (538 mg, 1.11 mmol) in THF (30 mL) was treated with 2.5% OSO₄ solution in tBuOH (3.0 mL), NaIO₄ (712 mg, 3.33 mmol) and water (3 mL). After stirring for 1.5 h at room temperature, the mixture was diluted with EtOAc. The organic solution was washed with brine, dried and concentrated. The residue was purified by flash chromatography in hexanes/EtOAc 4:1 to yield 2-[4-cyano-2-(2,6-dichlorophenylamino)-8-formyl-3-methyl-3H-benzimiazol-5-yl]-2-methyl-3-oxobutyric acid ethyl ester as an oil 345 mg, 64%).

A solution of the above aldehyde (35 mg, 0.07 mmol) in a mixture of H$_2$SO$_4$ (0.6 mL), acetic acid (0.6 mL) and water (0.6 mL) was heated at 100° C. for 1.5 h and cooled to room temperature. The resulting mixture was diluted water (10 mL) and the pH adjusted to 7 with ammonium hydroxide solution. The precipitated orange powder was filtered to give the title compound as an orange solid (18 mg, 60%).

Example 24

Synthesis of 2-(2,6-Dichlorophenylamino)-4-(2-hydroxyethylaminomethyl)-1,6,7-trimethyl-1,8-dihydro-imidazo[4,5-h]isoquinoline-9-one

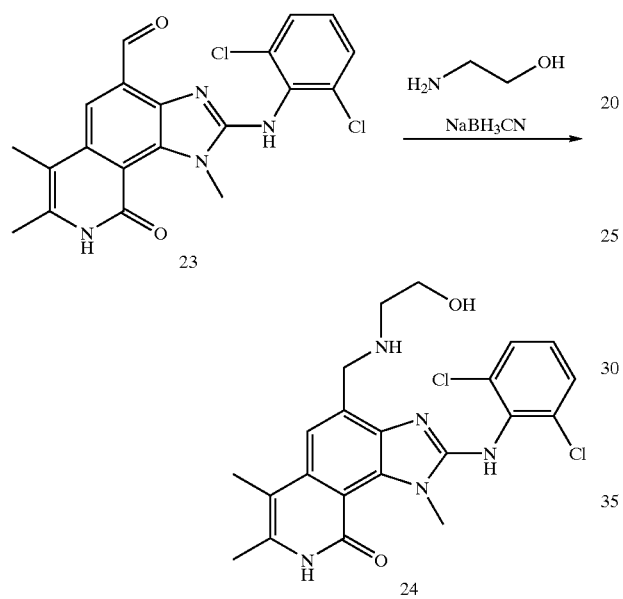

A suspension of the product of Example 23 (30 mg, 0.07 mmol) in MeOH (5 mL) was treated with ethanolamine (44 μL, 0.72 mmol) and NaBH$_3$CN (14 mg, 0.22 mmol), and stirred at room temperature for 16 h. The resulting mixture was concentrated and the residue was diluted with water. The precipitated solid was filtered to give the title compound (12 mg, 36%). mp decomp. above 250° C.; MS (CI) 460 (MH+).

Example 25

Synthesis of 2-(2,6-Dichlorophenylamino)-4-(3-methoxypropyn-1-yl)-1,6,7-trimethyl-1,8-dihydro-imidazo[4,5-h]isoquinoline-9-one

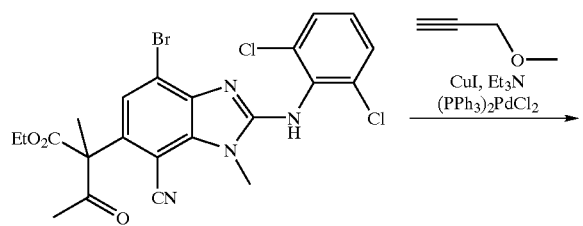

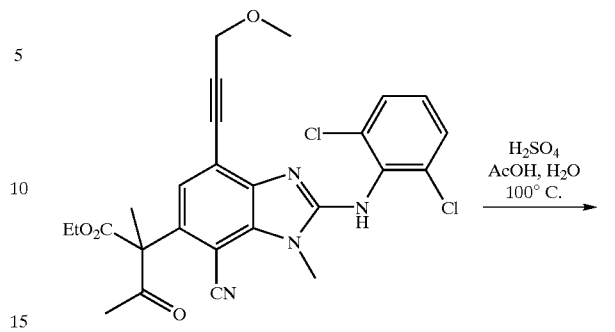

A mixture of 2-[8-bromo-4-cyano-2-(2,6-dichlorophenylamino)-3-methyl-3H-benzimidazol-5-yl]-2-methyl-3-oxobutyric acid ethyl ester (see Example 22) (50 mg, 0.09 mmol), methyl propargyl ether (16 μL, 0.19 mmol), (PPh$_3$)$_2$PdCl$_2$ (6.5 mg, 0.009 mmol) and CuI (3.5 mg, 0.02 mmol) in Et$_3$N (1 mL) and THF (1 mL) was stirred at room temperature for 5 days under argon. The resulting mixture was concentrated and the residue was purified by flash chromatography in hexanes/EtOAc 3:1 to give 2-[4-cyano-2-(2,6-dichlorophenylamino)-8-(4-methoxypropyn-1-yl)-3-methyl-3H-benzimidazol-5-yl]-2-methyl-3-oxobutyric acid ethyl ester as an oil (30 mg, 61%).

A solution of the above ketoester (29 mg, 0.006 mmol) in a mixture of H$_2$SO$_4$ (0.4 mL), acetic acid (0.4 mL) and water (0.4 mL) was heated at 100° C. for 2 h. The resulting mixture was cooled to room temperature and diluted with water (10 mL). The pH of this solution was adjusted to 8 with 10% NaOH solution. The precipitated solid was filtered to give the title compound (17 mg, 68%), mp decomp. above 250° C.; MS(CI) 455 (MH+).

Example 26

Synthesis of 2-(2,6-Dichlorophenylamino)-3,5-dihydro-imidazo[4,5-i]phenanthridin-4-one

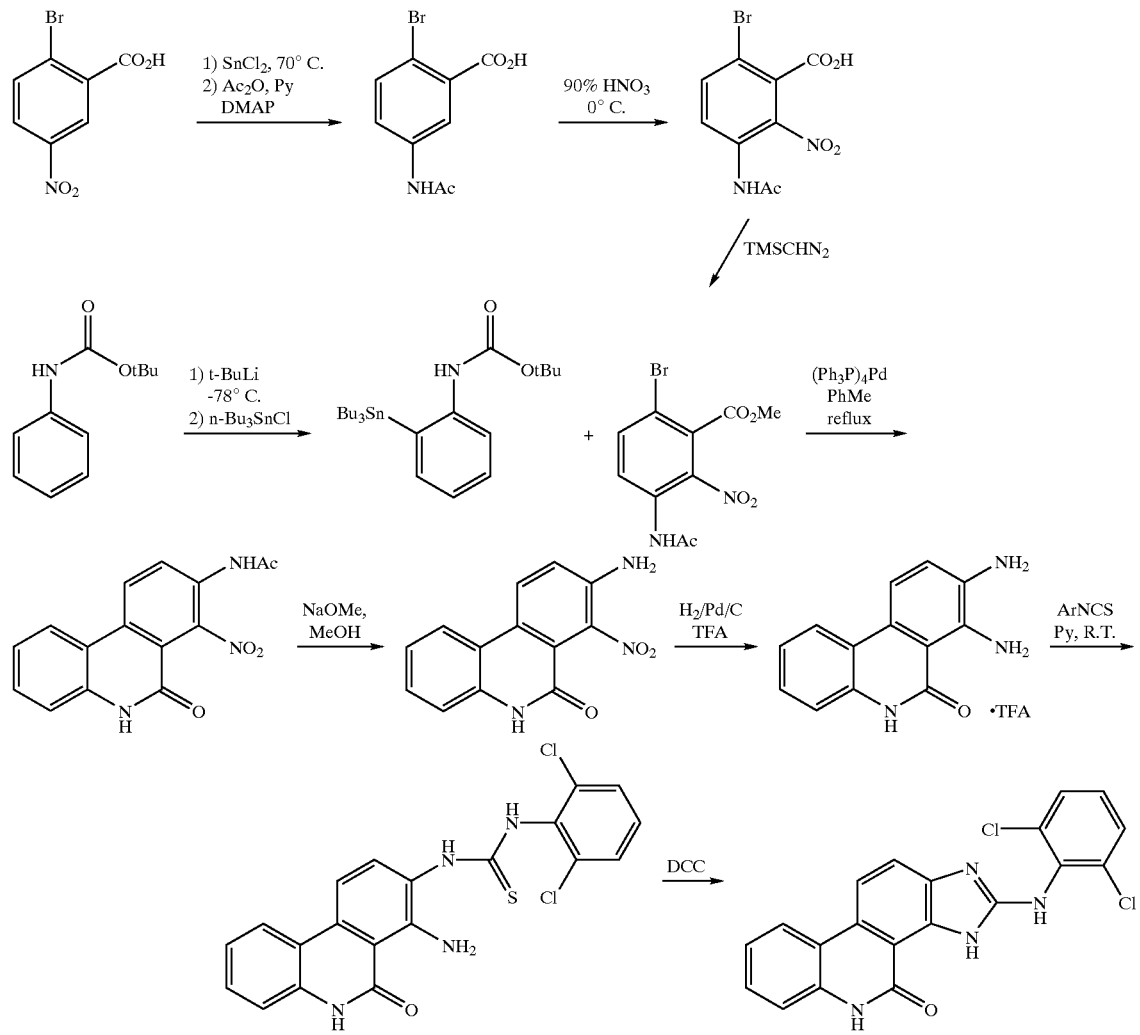

26

To a solution of N-(t-butoxycarbonyl)aniline (2.0 g, 10.35 mmol) in dry THF (50 mL) at −78° C., a solution of t-BuLi (2.7M in pentane, 26 mL, 25.88 mmol) was added dropwise over 30 min. The resulting yellow solution was warmed to −20° C. and stirred at this temperature for 2.5 h. n-Bu₃SnCl (4.2 mL, 15.52 mmol) in dry THF (10 mL) was added over 20 min, and the solution stirred at −20° C. for 2 h, then at room temperature for 12 h.

The reaction mixture was poured into NaHCO₃ solution and extracted with ether. The extract was washed with water, brine, and dried over MgSO₄. The solvent was evaporated and the resulting oil purified by flash chromatography in hexanes/ether (20:1) to give 2-tributylstannylphenylcarbamic acid t-butyl ester (2.42 g, 54%).

Tin(II) chloride (46.67 g, 206.84 mmol) was added portionwise to a solution of 2-bromo-5-nitro benzoic acid (12.71 g, 49.9 mmol) in dry ethanol (200 mL). The mixture was heated at 70° C. for 45 min, then ethanol was evaporated. The residue was cooled to 0° C., and acetic anhydride (43 mL) and pyridine (26 mL) were added. The solution was stirred at room temperature for 14 h and evaporated. The residue was partitioned between aq. 2M HCl and ethyl acetate (400 mL). The organic phase was washed with brine and dried over MgSO₄. The residue from evaporation was crystallized from water to give 5-acetylamino-2-bromobenzoic acid (12.4 g, 96%).

5-Acetylamino-2-bromobenzoic acid (6.81 g, 26.39 mmol) was added portionwise to fuming nitric acid (90%, 11 mL) at 0° C. (as described by H. Goldstin, G. Preitner. *Helv. Chim. Acta* 1944, 27, 888). The ice bath was removed and the solution stirred at room temperature for 1.5 h, then poured into ice water. 3-Acetylamino-6-bromo-2-nitro-benzoic acid was collected by filtration (5.07 g, 63%).

To a solution of 3-acetylamino-6-bromo-2-nitro-benzoic acid (3.86 g, 14.96 mmol) in dry THF (42 mL) and dry methanol (18 mL) was added a solution of (trimethylsilyl)diazomethane in hexane (2M, 24 mL, 48 mmol). The solution was stirred at room temperature for 3 h and evaporated. The residue was purified by flash chromatography in hexanes/ethyl acetate (6:1) to give 3-acetylamino-6-bromo-2-nitrobenzoic acid methyl ester (2.45 g, 52%).

A solution of 3-acetylamino-6-bromo-2-nitrobenzoic acid methyl ester (1.3 g, 4.11 mmol) and Pd(PPh$_3$)$_4$ (0.31 g, 0.27 mmol) in dry toluene (15 mL) was stirred at room temperature for 10 min. To this orange solution was added a solution of 2-tributylstannylphenylcarbamic acid t-butyl ester (2.10 g, 4.94 mmol) in dry toluene (10 mL) and the mixture was heated to reflux for 14 h, during which time a precipitate formed. 8-Acetamido-7-nitro-6-oxo-5,6-dihydro-phenanthridin-6-one was collected by filtration as an off-white solid (1.07 g, 88%).

A suspension of 8-acetamido-7-nitro-6-oxo-5,6-dihydro-phenanthridin-6-one (770 mg, 2.66 mmol) and NaOMe (25% w/w solution in MeOH, 3.5 mL, 6.64 mmol) in dry methanol (15 mL) was heated to reflux for 3 h. The methanol was evaporated and the residue triturated with water and filtered to yield 8-amino-7-nitro-5H-phenanthridin-6-one (500 mg, 74%).

A mixture of 8-amino-7-nitro-5H-phenanthridin-6-one (412 mg, 1.62 mmol), Pd/C (10 wt %, 234 mg) in TFA was hydrogenated at 50 psi for 50 min. The catalyst was filtered through a plug of diatomaceous earth and rinsed with ethanol. The solvent was evaporated to obtain 7,8-diamino-5H-phenanthridin-6-one trifluoroacetate salt (520 mg, 71%).

To a solution of 7,8-diamino-5H-phenanthridin-6-one trifluoroacetate salt (200 mg, 0.44 mmol) in pyridine (3 mL) was added 2,6-dichlorophenylisothiocyanate (93 mg, 0.46 mmol). The suspension was stirred at room temperature for 14 h. The pyridine was evaporated using a toluene azeotrope. The residue was triturated with ethanol to obtain the thiourea (150 mg, 79%). A mixture of thiourea (146 mg, 0.34 mmol) and dicyclohexylcarbodiimide (83 mg, 40.80 mmol) in dry THF (2 mL) and dry DMF (0.9 mL) was heated to 80° C. for 8 h. The solvent was removed under high vacuum and the residue triturated with hot ethanol to give the title compound (82 mg, 61%), mp >300° C.; MS(CI) 395, 397(MH+).

Example 27

Synthesis of 2-(2,6-Dichlorophenylamino)-3-methyl-5,6,7,8-tetrahydro-3H-1,3,5-triaza-dicyclopenta[a,f]naphthalen-4-one

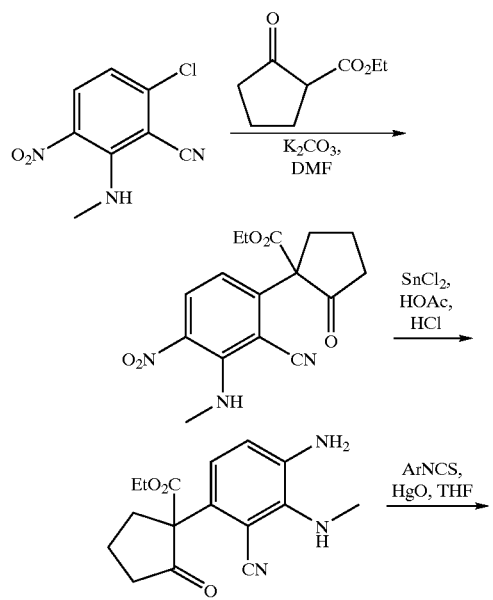

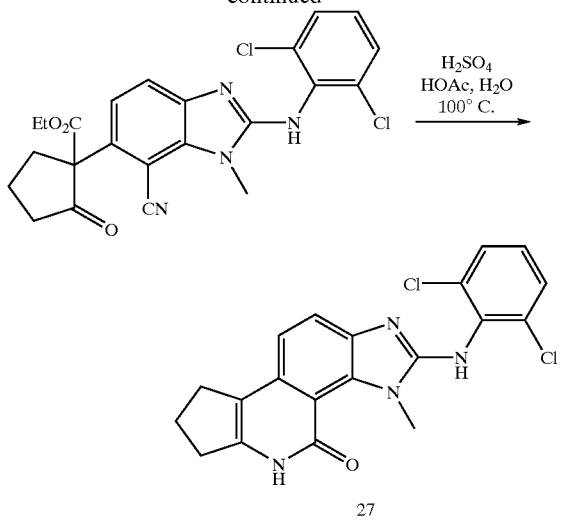

27

A mixture of 6-chloro-2-methylamino-3-nitrobenzonitrile (200 mg, 0.95 mmol) (Example 4), ethyl 2-oxocyclopentanecarboxylate (177 mg, 1.13 mmol) and K$_2$CO$_3$ (287 mg, 2.07 mmol) in DMF (5 mL) was stirred at room temperature for 60 h. The mixture was diluted with sat. NH$_4$Cl solution and extracted with ether. The ethereal layer was washed with water and brine, dried (Na$_2$SO$_4$), filtered and concentrated. The residue was purified by chromatography on silica (hexanes: EtOAc=3:1) to give ethyl 1-(2-cyano-3-methylamino-4-nitrophenyl)-2-oxo-cyclopentanecarboxylate (127 mg, 40%) as a yellow solid.

To a solution of the above compound (100 mg, 0.30 mmol) in acetic acid (1 mL) was added a solution of tin (II) chloride dihydrate (681 mg, 3.0 mmol) in c. HCl (0.5 mL) at room temperature. The resulting mixture was stirred at room temperature for 2 h and quenched with sat. NaHCO$_3$ solution. The pH of the mixture was adjusted to 8 with NaHCO$_3$. The product was extracted into EtOAc and the organic layer was washed with water and brine, dried (Na$_2$SO$_4$), and concentrated to give ethyl 1-(4-amino-2-cyano-3-methylaminophenyl)-2-oxo-cyclopentanecarboxylate (76 mg, 84%) as a yellow oil.

A mixture of the above diamine (140 mg, 0.46 mmol), 2,6-dichlorophenyl isothiocyanate (104 mg, 0.51 mmol) and HgO (110 mg, 0.51 mmol) in THF (5 mL) was refluxed for 8 h.

The cooled mixture was filtered through diatomaceous earth and concentrated. The residue was diluted with EtOAc, washed with water and brine, dried (Na$_2$SO$_4$), filtered and evaporated. The residue was purified by chromatography on silica in hexanes/EtOAc, (1:1) to give ethyl 1-[4-cyano-2-(2,6-dichlorophenylamino)-3-methyl-3H-benzimidazol-5-yl]-2-oxo-cyclopentanecarboxylate (200 mg, 92%) as a light yellow solid.

A solution of the above benzimidazole (195 mg, 0.41 mmol) in a 1:1:1 mixture of water, acetic acid and H$_2$SO$_4$ (1.5 mL) was heated at 100° C. for 3 h. The reaction mixture was cooled and diluted with water. The precipitate was collected and washed with water. The collected yellow solid was purified by chromatography on SiO$_2$ in CH$_2$Cl$_2$/MeOH (20:1) to give the title compound (70 mg, 43%) as a light yellow solid. Mp>300° C. (dec.), MS (CI) m/z 399 (M$^+$+H).

Example 28

Synthesis of 7-(3-Aminopropen-1-yl)-2-(2,6-dichlorophenylamino)-i,6-dimethyl-1,8-dihydro-imidazo[4,5-h]-isoquinolin-9-one

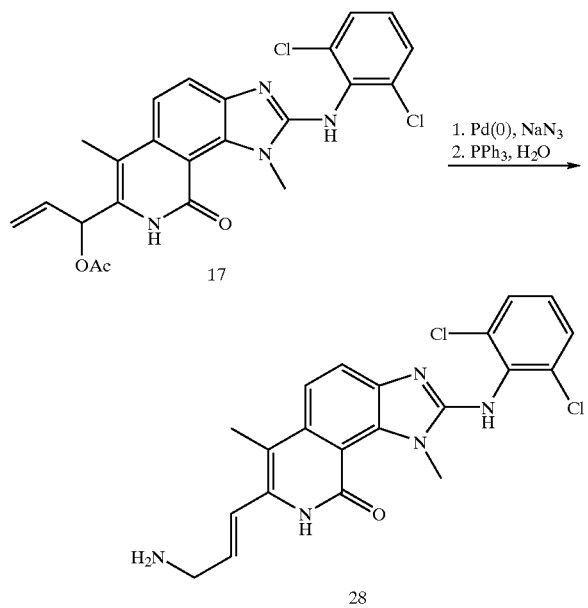

A suspension of tris(dibenzylideneacetone) dipalladium (0) (185 mg, 0.25 mmol) and triphenylphosphine (320 mg, 1.2 mmol) in THF (40 mL) was stirred for 20 min under $N_2$. A solution of the product from Example 17 (1.88 g, 4.0 mmol) in THF (5 mL) was added and the mixture stirred for 20 min. Sodium azide (280 mg, 4.4 mmol) and water (4.0mL) were added and the reaction was heated at 60° C. for 3 h. The solution was cooled to rt and triphenylphosphine (1.0 g, 3.8 mmol) was added. After stirring for 45 min., ammonium hydroxide (4 mL) was added and stirring continued overnight. The resulting solution was dried over $MgSO_4$, then concentrated to an oil. Column chromatography on silica eluting with $CH_2Cl_2$/MeOH (90:10 increasing to 50:50) provided the title compound (1.2 g, 70%), mp>300° C.; MS (ES) 428 (MH+).

Example 29

Synthesis of 1-{3-[2-(2,6-dichlorophenylamino)-1,6-dimethyl-9-oxo-8,9-dihydro-1H-imidazo[4,5-h]isoquinolin-7-yl]-propenyl}-3-phenyl urea

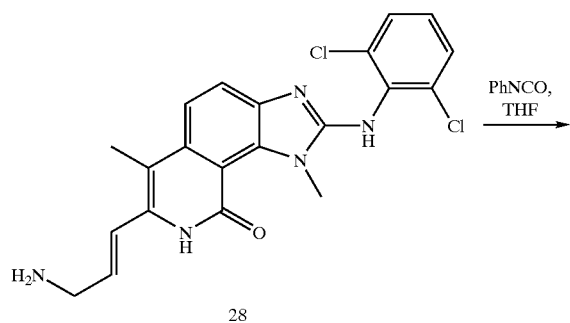

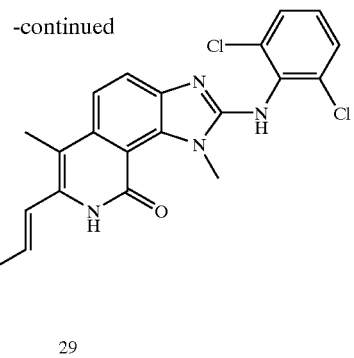

A solution of the product of Example 28 (50 mg, 0.12 mmol) and phenyl isocyanate (17 mg, 0.13 mmol) in DMF (2 mL) was heated at 60° C. for 10 h. The resulting precipitate was filtered, triturated with $MeOH/CH_2Cl_2$ (90:10), and dried to provide the title compound (57 mg, 89%) mp>290° C.; MS (ES) 547 (MH+).

OTHER EXAMPLES

Using methods analogous to those described above, the following compounds of this invention (Tables 1–3) were prepared:

TABLE 1

Compounds of Formula I with $R_4$, $R_5$ = C

| Example | X | $R_1$ | $R_2$ | $R_3$ | $R_a$ | $R_6$ | $R_7$ | m.p. ° C. |
|---|---|---|---|---|---|---|---|---|
| 30 | NH | Me | Cl | H | H | Me | Me | >300 |
| 31 | NH | Cl | Cl | Cl | H | Me | Me | >275 |
| 32 | NH | Me | Me | H | H | Me | Me | >300 |

TABLE 2

Compounds of Formula I with $R_4$, $R_5$ = A

| Example | X | $R_1$ | $R_2$ | $R_3$ | $R_1$ | $R_6$ | $R_7$ | m.p. ° C. |
|---|---|---|---|---|---|---|---|---|
| 33 | NH | Cl | Cl | H | H | H | H | 172–178 |

TABLE 3

Compounds of Formula I with $R_4, R_5 = B$

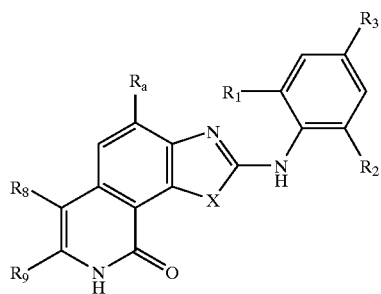

| Ex: | X | $R_1$ | $R_2$ | $R_3$ | $R_a$ | $R_8$ | $R_9$ | m.p. °C. |
|---|---|---|---|---|---|---|---|---|
| 34 | S | Cl | Cl | H | H | Me | Me | >300 |
| 35 | NH | H | Cl | H | H | Me | Me | >300 |
| 36 | NH | Cl | Cl | Cl | H | Me | Me | >250 |
| 37 | NH | Br | Br | Br | H | Me | Me | >250 |
| 38 | NH | Cl | Me | H | H | Me | Me | >250 |
| 39 | NH | Cl | Cl | H | H | H | n-Pr | >250 |
| 40 | NH | Cl | Cl | H | H | $CO_2Et$ | Me | 265 |
| 41 | NH | Cl | Cl | H | H | Me | CHO | >300 |
| 42 | NH | Cl | Cl | H | H | $CH_2CO_2Et$ | Me | 292–296 |
| 43 | NH | Cl | Cl | H | H | H | Me | >300 |
| 44 | NH | Cl | Cl | H | H | Me | $CH_2OH$ | >300 |
| 45 | NH | Cl | Cl | OMe | H | Me | Me | >300 |
| 46 | NH | Cl | Cl | H | H | $CH_2CO_2H$ | Me | >250 |
| 47 | NMe | Cl | Cl | H | H | Me | $CH_2NH(CH_2)_2NEt_2$ | 194–196 |
| 48 | NMe | Cl | Cl | H | H | Me | $CH_2OH$ | >280 |
| 49 | NMe | Cl | Cl | H | H | Me | $CH_2NHMe$ | 263–265 |
| 50 | NMe | Cl | Cl | H | H | Me | $CH_2NH(CH_2)_2OMe$ | 215–218 |
| 51 | NMe | Cl | Cl | H | H | Me | $CH_2$(4-morpholinyl) | 292–295 |
| 52 | NMe | Cl | Cl | H | H | $CH_2CO_2Et$ | Me | 280–285 |
| 53 | NMe | Cl | Cl | H | H | $CH_2C(O)NHEt$ | Me | >300 |
| 54 | NMe | Cl | Cl | H | H | $CH_2C(O)NMe_2$ | Me | >300 |
| 55 | NMe | Cl | Cl | H | H | $CH_2C(O)NH-CH_2Ph$ $NEt_2$ | Me | >300 |
| 56 | NMe | Cl | Cl | H | H | $CH_2C(O)NH-(CH_2)_2$ $NEt_2$ | Me | 298–302 |
| 57 | NMe | Cl | Cl | H | H | $CH_2C(O)NH-$ $(CH_2)_2Ph$ | Me | >300 |
| 58 | NMe | Cl | Cl | H | H | $CH_2C(O)$(4Me-piperazin-1-yl) | Me | >300 |
| 59 | NMe | Cl | Cl | H | H | $CH_2C(O)NH(CH_2)_3$ $NEt_2$ | Me | 267.5–270 |
| 60 | NMe | Cl | Cl | H | H | $CH_2CH_2OH$ | Me | >300 |
| 61 | NMe | Cl | Cl | H | H | $CH_2C(O)$(4-morpholinyl) | Me | >300 |
| 62 | NMe | Cl | Cl | H | H | $CH_2C(O)NH(CH_2)_2$ (4-morpholinyl) | Me | 277–283 |
| 63 | NMe | Cl | Cl | H | H | H | $CH=CHCO_2Me$ | >300 |
| 64 | NMe | Cl | Cl | H | H | $CH_2C(O)NH-$ $(CH_2)_2NEt_2$ | Me | >262 |
| 65 | NMe | Cl | Cl | H | H | $(CH_2)_2CO_2H$ | Me | 295–305 |
| 66 | NMe | Cl | Cl | H | H | $(CH_2)_2CO_2Et$ | Me | 268–273 |
| 67 | NH | Cl | Cl | H | H | $CH_2C(O)NMe_2$ | Me | >300 |
| 68 | NMe | Br | Br | H | H | Me | Me | 238–240 |
| 69 | NMe | Cl | Cl | H | H | $(CH_2)_2OC(O)Me$ | Me | >275 |
| 70 | NMe | Cl | Cl | H | H | $CH_2C(O)NHCH_2$ (pyridin-2-yl) | Me | >300 |
| 71 | NMe | Cl | Cl | H | H | $(CH_2)_2$(4-morpholinyl) | Me | 285–290 |
| 72 | NMe | Cl | Cl | H | H | $(CH_2)_2NHEt$ | Me | 253–262 |
| 73 | NMe | Cl | Cl | H | H | $CH_2C(O)NH_2$ | Me | >300 |
| 74 | NMe | Cl | Cl | H | H | H | $CH=CHC(O)N(OMe)Me$ | >300 |
| 75 | NMe | Cl | $CF_3$ | H | H | Me | Me | 226–228 |
| 76 | NMe | Cl | $NO_2$ | H | H | Me | Me | 278–280 |
| 77 | NMe | Cl | Cl | H | C(O)Me | Me | Me | >300 |
| 78 | NMe | Cl | Cl | H | H | H | $CH=CHC(O)NHCH_2Ph$ | >300 |
| 79 | NMe | Cl | Cl | H | C(OH)Me | Me | Me | 308–311 |
| 80 | NMe | Cl | Cl | H | H | $CH_2CH(OMe)_2$ | Me | 247–248 |
| 81 | NMe | Cl | Cl | H | H | H | $CH=CHC(O)$(4-morpholinyl) | >300 |
| 82 | NMe | Cl | Cl | H | H | $(CH_2)_3$(4-morpholinyl) | Me | 277–282 |

TABLE 3-continued

Compounds of Formula I with $R_4$, $R_5$ = B

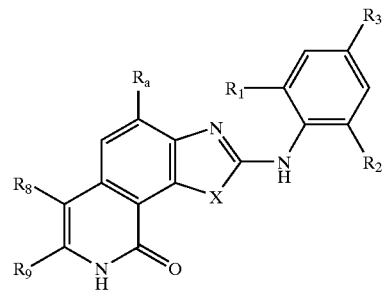

| Ex: | X | $R_1$ | $R_2$ | $R_3$ | $R_a$ | $R_8$ | $R_9$ | m.p. °C. |
|---|---|---|---|---|---|---|---|---|
| 83 | NMe | Cl | Cl | H | CH$_2$OH | Me | Me | >300 |
| 84 | NMe | Me | Me | H | H | Me | Me | 315–318 |
| 85 | NMe | Me | Et | H | H | Me | Me | 289–291 |
| 86 | NMe | Cl | Br | F | H | Me | Me | 317–319 |
| 87 | NMe | Cl | Cl | H | CH$_2$NH–CH$_2$(4-OMe)Ph | Me | Me | 247–250 |
| 88 | NMe | Cl | Cl | H | (3-Me)Ph | Me | Me | 220–223 |
| 89 | NMe | Cl | Cl | H | CH$_2$C(O)—CH$_2$OH | Me | Me | 285 |
| 90 | NMe | Cl | Cl | H | H | Me | CH=CHC(O)NH-[4-O(CH$_2$)$_2$NEt$_2$]Ph | >300 |
| 91 | NMe | Cl | Cl | H | H | H | CH=CHC(O)NHMe | >300 |
| 92 | NMe | Cl | NH$_2$ | H | H | Me | Me | 300–302 |
| 93 | NMe | Cl | Cl | H | (CH$_2$)$_3$OH | Me | Me | 208–210 |
| 94 | NMe | Cl | Cl | H | H | H | CH=CH$_2$ | 259–261 |
| 95 | NMe | Cl | Cl | H | H | Me | CH=CHCH$_2$-4-morpholinyl | 175–177 |
| 96 | NMe | Cl | Cl | H | H | Me | CH=CHCN | >300 |
| 97 | NMe | Cl | Me | H | H | H | Me | >300 |
| 98 | NMe | Cl | Cl | H | H | H | 5-oxazolyl | >300 |
| 99 | NMe | Cl | Cl | H | H | (CH$_2$)$_3$OH | Me | 265–275 |
| 100 | NMe | Cl | Cl | H | H | H | CH=CHCH$_2$OH | 285 |
| 101 | NMe | Cl | Me | H | H | H | CH=CHCH$_2$OH | 264–266 |
| 102 | NMe | Cl | Cl | H | H | Me | CH=CHCH$_2$NEt$_2$ | 150–153 |
| 103 | NMe | Cl | Cl | H | H | Me | CH=CHCN | 280 |
| 104 | NMe | Cl | Cl | H | H | Me | CH=CHCH$_2$-(1-pyrrolidinyl) | 170–173 |
| 105 | NMe | Cl | Cl | H | H | Me | CH=CHCH$_2$N(Me)(CH$_2$Ph) | 134–136 |
| 106 | NMe | Cl | Cl | OMe | H | Me | Me | >300 |
| 107 | NMe | Cl | Cl | OMe | H | Me | 5-oxazolyl | >300 |
| 108 | NMe | Cl | Cl | OCF$_3$ | H | Me | Me | >300 |
| 109 | NMe | Cl | Cl | H | H | H | CH=CHCH$_2$NEt$_2$ | 130–131 |
| 110 | NMe | Me | Me | H | H | H | Me | 200 |
| 111 | NMe | Cl | Cl | H | H | Me | CH=CHCH$_2$(4-Me-piperazin-4-yl) | 251–253 |
| 112 | NMe | Cl | Cl | H | H | Me | CH=CHCH$_2$(piperidin-1-yl) | 159–161 |
| 113 | NMe | Cl | Cl | H | H | Me | CH=CHCH$_2$N(Et)(CH$_2$CH$_2$OH) | 220–222 |
| 114 | NMe | Cl | Cl | H | H | Me | CH=CHCH$_2$N(Me)(OH) | 185–186 |
| 115 | NMe | Cl | Cl | H | H | Me | CH=CHCH$_2$(3-OH-pyrrolidin-1-yl) | 160–163 |
| 116 | NMe | Cl | Cl | H | H | Me | CH=CHCH$_2$N(n-Bu)$_2$ | 122–125 |
| 117 | NMe | Cl | Cl | H | H | Me | CH=CHCH$_2$N(Me)(MeOCH$_2$—CH$_2$) | 125–127 |
| 118 | NMe | Me | Me | H | H | Me | CH=CHCH$_2$NEt$_2$ | 185–191 |
| 119 | NMe | Cl | Cl | H | H | Me | CH=CHCH$_2$N(Me)(Et$_2$NCH$_2$—CH$_2$) | 119–121 |
| 120 | NMe | Cl | Me | H | H | Me | CH=CHCH$_2$NEt$_2$ | 130–132 |
| 121 | NMe | Cl | Cl | H | H | Me | CH=CHCH$_2$N(Me)((CH$_2$)$_3$NMe$_2$) | 116–119 |
| 122 | NMe | Cl | Cl | H | H | Me | CH=CHCH$_2$SCH$_2$CH$_2$NEt$_2$ | 141–146 |
| 123 | NMe | Cl | Cl | H | H | Me | CH=CHCH$_2$NMe$_2$ | 245–247 |
| 124 | NMe | Cl | Cl | H | H | Me | CH=CHCH$_2$N(Me)(cyclohexyl) | 148–151 |
| 125 | NMe | Cl | Cl | H | H | Me | CH=CHCH$_2$N(Me)(i-Pr) | 155–157 |
| 126 | NMe | H | H | H | H | Me | Me | 280 dec |
| 127 | NMe | H | Cl | H | H | Me | Me | 240 dec |
| 128 | NMe | H | H | Cl | H | Me | Me | >300 |
| 129 | NMe | Cl | Cl | Cl | H | Me | Me | >300 |
| 130 | NMe | Cl | H | H | H | Me | CH=CHCH$_2$NEt$_2$ | 144–146 |
| 131 | NMe | Cl | Cl | Cl | H | Me | CH=CHCH$_2$NEt$_2$ | 197–199 |
| 132 | NMe | H | H | H | H | Me | CH=CHCH$_2$NEt$_2$ | 172–175 |
| 133 | NH | Cl | Cl | H | H | Me | 5-oxazolyl | >300 |
| 134 | NMe | Cl | Cl | H | H | Me | CN | >300 |

TABLE 3-continued

Compounds of Formula I with $R_4$, $R_5$ = B

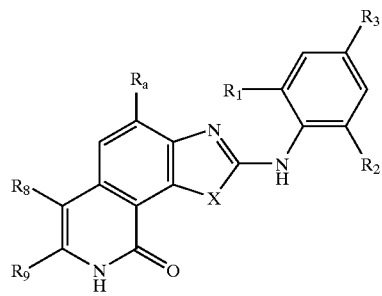

| Ex: | X | $R_1$ | $R_2$ | $R_3$ | $R_a$ | $R_8$ | $R_9$ | m.p. ° C. |
|---|---|---|---|---|---|---|---|---|
| 135 | NMe | Cl | Cl | H | H | Me | 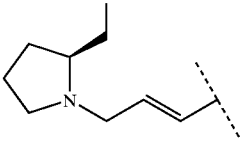 | 135–137 |
| 136 | NMe | Cl | Cl | H | H | Me | 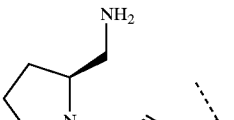 | 186–188 |
| 137 | NMe | Cl | Cl | H | H | Me | 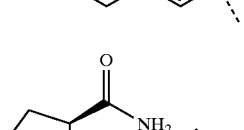 | 289–290 |
| 138 | NMe | Cl | Cl | H | H | Me | CH=CHCH$_2$-(3-NH2CO-piperidin-1-yl) | 182–184 |
| 139 | NMe | Cl | Cl | H | H | Me | CH=NNMe$_2$ | >300 |
| 140 | NMe | Cl | Cl | H | H | Me | CH=NNHMe | 295–299 |
| 141 | NMe | Cl | Cl | H | H | Me | CH$_2$OC(O)Me | >285 |
| 142 | NMe | Cl | Cl | H | H | Me | CH=CHCH$_2$-(3-NH2-pyrrolidin-1-yl) | 200–202 |
| 143 | NMe | Cl | Cl | H | H | Me | CH=CHCH$_2$-(3-MeC(O)NH-pyrrohdin-1-yl) | 237–239 |
| 144 | NMe | Cl | Cl | H | H | Me | CH=CHCH$_2$-(3-NMe$_2$-pyrrolidin-1-yl) | 189–191 |
| 145 | NMe | Cl | Cl | H | H | Me | CH=CHCH$_2$-(2-NH$_2$CO-piperidin-1-yl) | 202–204 |
| 146 | NMe | Cl | Cl | H | H | Me | CH=N(pyrrolidin-1-yl) | 285–295 dec |
| 147 | NMe | Cl | Cl | H | H | Me | CH=NNHC(O)NH$_2$ | 267–270 dec |
| 148 | NMe | Cl | Cl | H | H | Me | C(O)NH$_2$ | dec >228 |
| 149 | NMe | Cl | Cl | H | H | Me | 2,3-dihydrobenzimidazol-2-yl | dec. >240 |
| 150 | NMe | Cl | Cl | H | H | Me | Benzimidazol-2-yl | 248–252 |
| 151 | NMe | Cl | Cl | H | H | Me | CH=NMHPh | >300 |
| 152 | NMe | Cl | Cl | H | H | Me | 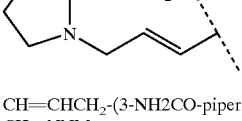 | 264–265 |
| 153 | NMe | Cl | Cl | H | H | Me | CH=CHCH$_2$(3-NH$_2$CH$_2$-piperidin-1-yl) | 163–165 |
| 154 | NMe | Cl | Cl | H | H | Me | CH=CHCH$_2$(3-NEt$_2$C(O)-piperidin-1-yl) | 169–171 |
| 155 | NMe | Cl | Cl | H | H | Me | 5-NH$_2$-benzimidazol-2-yl | dec. 290 |
| 156 | NMe | Cl | Cl | H | H | Me | 2,3-dihydro-1H-imidazo[4,5-c]pyridin-2-yl | >300 |
| 157 | NMe | Cl | Cl | H | H | Me | imidazo[4,5-c]pyridin-2-yl | >300 |
| 158 | NMe | Cl | Cl | H | H | Me | 4-NH$_2$-benzimidazol-2-yl | dec>290 |
| 159 | NMe | Cl | Me | NH$_2$—C(O) | H | Me | Me | >300 |

TABLE 3-continued

Compounds of Formula I with R_4, R_5 = B

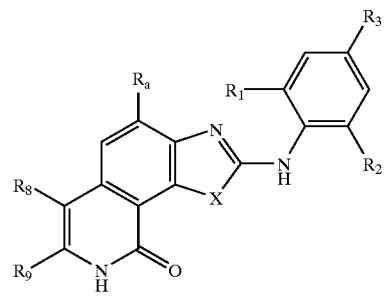

| Ex: | X | $R_1$ | $R_2$ | $R_3$ | $R_a$ | $R_8$ | $R_9$ | m.p. °C. |
|---|---|---|---|---|---|---|---|---|
| 160 | NMe | Cl | Cl | H | H | Me | C≡CH | dec.>290 |
| 161 | NMe | Cl | Cl | H | H | Me | CH=CHCH_2NHC(O)NHMe | >290 |
| 162 | NMe | Cl | Cl | CF_3 | H | Me | Me | >300 |
| 163 | NMe | Cl | Cl | H | H | Me | CH(OH) cyclopentyl | 285 (dec.) |
| 164 | NMe | Cl | Cl | H | H | Me | CH=CHCH_2NHC(O)cyclohexyl | >290 |
| 165 | NMe | Cl | Cl | H | H | Me | CH=CHCH_2NHC(O)NH[2-MeOC(O)]Ph | >290 |
| 166 | NMe | Cl | Cl | H | H | Me | CH=CHCH_2NH C(O)NH[3-CN]Ph | >300 |
| 167 | NMe | Cl | Cl | H | H | H | Ph | >250(dec) |
| 168 | NMe | Cl | Cl | H | H | Me | CH=CHCH_2NHC(O)Ph | >290 |
| 169 | NMe | Cl | Cl | H | H | Me | CH=CHCH_2NHC(O)NH[3-EtOC(O)]Ph | >290 |
| 170 | NMe | Cl | Cl | H | H | Me | Ph | >300 |
| 171 | NMe | Cl | Cl | H | H | EtOC(O) | Ph | 283–284 |
| 172 | NMe | Cl | Cl | H | H | Me | CH=CHCH_2NHC(O)NH[3-NO_2]Ph | >290 |
| 173 | NMe | Cl | Cl | H | H | Me | CH=CHCH_2NHC(O)NH[2-NO_2]Ph | >290 |
| 174 | NMe | Cl | Cl | H | H | Me | CH=CHCH_2NHS(O)_2Me | >290 |
| 175 | NMe | Cl | Cl | H | H | Me | CH=CHCH_2NHC(O)NH_2 | >290 |
| 176 | NMe | Cl | Cl | H | H | Me | (cyclopenten-1-yl)CH_2 | — |
| 177 | NMe | Cl | Cl | H | H | Me | (cyclopentylidene-1-yl)CH | — |
| 178 | NMe | Cl | Cl | H | H | Me | CH=CHCH_2NHC(O)NH(cyclohexyl) | >290 |
| 179 | NMe | Cl | Cl | H | H | Me | CH=CHCH_2NHSO_2Ph | >290 |
| 180 | NMe | Me | Me | OMe | H | Me | Me | — |
| 181 | NMe | Cl | Cl | H | H | Me | CH=CHCH_2NHEt | 218–221 |
| 182 | NMe | Cl | Cl | H | H | Me | CH=CHCH_2NHC(=NH)NH_2 | >290 |
| 183 | NMe | Cl | Cl | H | H | Me | CH=CHCH_2(2,4-dioxo-quinazolin-3-yl) | >290 |
| 184 | NMe | Cl | Cl | H | H | Me | (3-CO_2H)Ph | >300 |
| 185 | NMe | Cl | Cl | H | H | Me | (3-Br)Ph | >300 |
| 186 | NMe | Cl | Cl | H | H | Me | CH=CHCH_2NHC(O)(piperidin-3-yl) | >290 |
| 187 | NMe | Cl | Cl | H | H | Me | (L-prolinamide-allyl structure) | 279–282 |
| 188 | NMe | Cl | Cl | H | H | Me | (D-prolinamide-allyl structure) | |
| 189 | NMe | Cl | Cl | H | H | Me | [3-NH_2C(O)]Ph | >300 |
| 190 | NMe | Cl | Cl | H | H | Me | (azetidine-carboxamide-allyl structure) | >290 |
| 191 | NMe | Cl | Cl | H | H | Me | CH=CHCH_2NH C(O)(piperidin-2-yl) | 269–273 |
| 192 | NMe | Cl | Cl | H | H | Me | (3-CN)Ph | >300 |
| 193 | NMe | Cl | Cl | H | H | Me | (3-NH_2CH_2)Ph | 241–246 |
| 194 | NH | Me | Me | OMe | H | Me | Me | foam |
| 195 | NMe | Cl | Cl | H | H | Me | (3-NH_2C(=NH)NHCH_2)Ph | 245–253 |
| 196 | NPr | Cl | Cl | H | H | Me | Me | 280–281 |
| 197 | NEt | Cl | Cl | H | H | Me | Me | >300 |

TABLE 4

Compounds of Formula I with $R_4, R_5 = B$

| Ex. | X | Ar$_1$ | R$_a$ | R$_8$ | R$_9$ | m.p. °C. |
|---|---|---|---|---|---|---|
| 198 | NH | 3,5-dichloro-pyridin-4-yl | H | Me | Me | >300 |
| 199 | NH | 2,4-dimethyl-pyridin-3-yl | H | Me | Me | >300 |
| 200 | NMe | cyclohexyl | H | Me | Me | 335(dec) |
| 201 | NMe | 2-chloro-4-methyl-pyridin-3-yl | H | Me | Me | 295(dec) |
| 202 | NMe | (2,6-dimethyl)cyclohexyl | H | Me | Me | 268–269 |
| 203 | NMe | 3,5-dichlorophenyl | H | Me | Me | >300 |
| 204 | NMe | 3,5-dichlorophenyl | H | Me | CH=CHCH$_2$NEt$_2$ | 250(dec) |

TABLE 4-continued

Compounds of Formula I with $R_4$, $R_5$ = B

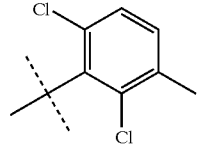

| Ex. | X | Ar₁ | $R_a$ | $R_8$ | $R_9$ | m.p. ° C. |
|---|---|---|---|---|---|---|
| 205 | NMe | 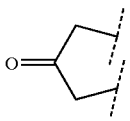 | H | Me | Me | >300 |

TABLE 5

Compounds of Formula I wherein $R_4$, $R_5$ = B and $R_8$ and $R_9$ together form a ring

| Ex | X | $R_1$ | $R_2$ | $R_3$ | $R_a$ | $R_8$ and $R_9$ | m.p. ° C. |
|---|---|---|---|---|---|---|---|
| 206 | NMe | Cl | Cl | H | H | (cyclopentanone) | >300 |
| 207 | NMe | Cl | Cl | H | H | (hydroxycyclopentane) | >300 |
| 208 | NMe | Cl | Cl | H | H | (methylcyclopentane) | >300 |
| 209 | NMe | Cl | Cl | H | H | (dioxolane-cyclopentane) | >300 |

TABLE 5-continued

Compounds of Formula I wherein $R_4$, $R_5$ = B and $R_8$ and $R_9$ together form a ring

| Ex | X | $R_1$ | $R_2$ | $R_3$ | $R_a$ | $R_8$ and $R_9$ | m.p. ° C. |
|---|---|---|---|---|---|---|---|
| 210 | NMe | Cl | Cl | H | H | 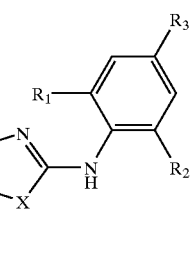 | foam |
| 211 | NMe | Cl | Cl | H | H |  | >300 |
| 212 | NMe | Cl | Cl | H | H | 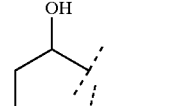 | >300 |

Assessment of Biological Properties

Tyrosine Kinase Inhibition Assay

The inhibition of tyrosine kinases by the compounds of the invention was measured with the following assay.

Kinase Reaction Buffer 50 mM Hepes, pH 7.5, 50 mM KCl, 25 mM MgCl$_2$, 5 mM MnCl$_2$, 100 μM, Na$_3$VO$_4$, 0.01% CHAPS, 1 mM DTT, and 50 mg/mL BSA, Adenosine 5'-Triphosphate (ATP) solution at 100 mM, pH 7.5-γ33P-ATP, 2000 Ci/mmol at 10 μCi/μl,-Poly(L-glutamic acid-L-tyrosine, 4:1) or (E4Y)$_n$ at 10 mg/mL in water.

Assay: Test compounds, obtained routinely at 5 mg/mL in 100% DMSO were diluted appropriately into complete Kinase assay buffer with 10% DMSO, 10 μl of the 6×compound solution was distributed into each assay well, the final compound concentration for IC$_{50}$ determinations ranged from 200 to 1 μg/mL. [γ33P]-ATP label was prepared as a 10 Ci/mmol working solution in complete Kinase assay buffer. Protein kinase was initiated by adding 10 to 50 ηg of diluted enzyme stock.

Plates were incubated at 30° C. for 30 min. During the incubation period, the MultiScreen harvest plates were pre-wetted with 10% TCA/5% Ppi. 150 μl of TCA/PPi was added to all MultiScreen plate wells after pre-wetting. The kinase reaction was stopped via replica transfer of the polypropylene reaction wells into the MultiScreen plates. The plates were incubated at room temperature for 5 min then vacuum harvested and washed with 200 μl TCA/PPi 3–4 times per well, then 100 μl of cocktail per well was added.

Experimental data consisted of eight (8) compound doses in duplicate with ten (10) enzyme control reaction wells (so-called totals) and six (6) background wells. The results were obtained as percent inhibition (mean with S.D.) over the full compound dose range. IC$_{50}$ potency estimates are determined using a floating inhibition maximum (Imax).

All compounds in the synthetic examples and Tables above were evaluated in the tyrosine kinase assay above using a kinase such as p56 lck and were found to have IC$_{50}$'s less than 10 μM.

Representative compounds from the examples above were evaluated in the tyrosine kinase assay above using p60 src and were found to have IC$_{50}$'s less than 10 μM.

Representative compounds from the examples above were evaluated in the tyrosine kinase assay above using PDGFR kinase and were found to have IC$_{50}$'s less than 10 μM.

Inhibition of IL-2 Production

Inactivation of T cells resulting from inhibition of the tyrosine kinase p56 lck can be measured by inhibition of IL-2 production in Jurkat cells. 96-well flat bottom plates were coated with anti-CD3, clone UCHT1, (Immunotech cat. # 1304) at 4 μg/ml in Phosphate Buffered Saline (PBS), 100 μl/well. The solution was prepared by taking 200 μl of 200 μg/ml anti-CD3 stock/10 ml PBS. The plate was then incubated at 37° C. for 2 h. Jurkat cells were pelleted and counted. The cells were resuspended at 2.5×10$^6$ cells/ml in RPMI, 10% FBS (complete media). Test compounds were diluted from a 5 mg/ml DMSO stock directly into complete media.

10 μl of 20×compound/ well was added to a separate plate, followed by 100μl of cell suspension in triplicate and this plate was preincubated at 37° C. for 30 min. The 96-well plate containing anti-CD3 was aspirated, and the cells and compound transferred to this plate. 100 μl of PMA (Phorbol 12-Myristate 13-Acetate, Sigma cat.# P-8139) at 20 ng/ml was added, and the plate was incubated overnight at 37° C. (PMA stock at 1 mg/ml in ethanol, dilute 10 μl/ml in complete media, then 20 μl/10 mls. in complete media. 100 μl/well=10 ng/ml. final concentration). The next day, the plate was centrifuged at 1500 rpm for 5 min. at room temperature and the supernatants were removed. The supernatants were tested using R&D Systems Quantikine Human IL-2 Kit (cat.#2050). Samples were diluted 1:5 in RPMI1640, and 100 μl/well used in the ELISA. The optical density of each well was determined using a microplate reader set to 450 nm. EC$_{50}$ values were determined using Origin (non-linear regression) or SAS by plotting absorbance vs. concentration of compound.

Representatives from the synthetic examples and the Tables above were screened in this assay and had IC$_{50}$.s below 10 μM.

We claim:
1. A Compound of the formula(I):

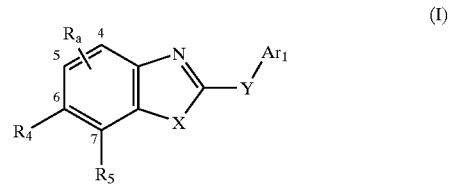

wherein:
Ar$_1$ is an aromatic or nonaromatic carbocycle, heteroaryl selected from pyridinyl, pyrimidinyl, pyrazinyl, pyridazinyl, pyrrolyl, imidazolyl, pyrazolyl, thienyl, furyl, isoxazolyl, isotbiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, beuzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazifle, cyclohexanopyridazine, cyclopentanoquinoline, cyclohexanoquinoline, cyclopentanoisoquinolifle, cyctohexanoisoquinoline, cyclopentanoindole, cyclohexanoindole, cyclopentanobenzimidazole, cyclohexanobenzimidazole, cyclopentanobenzoxazole, cyclohexanobeuzoxazole, cyclopentanoimidazole, cyclohexanoimidazole, cyclopentanothiophene and cyclohexanothiophene; or a heterocycle selected from pyrrolinyl, pyrrolidinyl, pyrazolinyl, pyrazolidinyl, piperidinyl, morpholinyl, thiomorpholinyl, pyranyl, thiopyranyl, piperazinyl and indolinyl;

wherein said carbocycle, heteroaryl or heterocycle is optionally substituted by one or more R$_1$, R$_2$ and R$_3$;

X is NH, N—C$_{1-3}$alkyl, N-cyclopropyl;

Y is NR$_{15}$, S or O;

R$_a$ is H, C$_{1-10}$alkyl, C$_{2-10}$alkenyl or C$_{2-10}$alkynyl, each of which may be branched or cyclic; or R$_a$ is aryl or heteroaryl; wherein each R$_a$ is independently optionally substituted with one or more C$_{1-6}$alkyl, C$_{1-6}$alkoxy, halogen. OH, oxo, NR$_{10}$R$_{11}$, aryl or heteroaryl each aryl or heteroaryl being optionally substituted with one or more groups selected from halogen, OH, C$_{1-3}$alkyl, C$_{1-3}$alkoxy, hydroxyC$_{1-3}$alkyl and (CH$_2$)$_m$NR$_{10}$R$_{11}$; and wherein R$_a$ is attached at the 4- or 5-position;

R$_1$ and R$_2$ are the same or different and selected from H, halogen, CN, NO$_2$, C$_{1-10}$ branched or unbranched saturated or unsaturated alkyl, C$_{1-10}$ branched or unbranched alkoxy, C$_{1-10}$ branched or unbranched acyl, C$_{1-10}$ branched or unbranched acyloxy, C$_{1-10}$ branched or unbranched alkylthio, aminosulfonyl, di($C_{1-3}$) alkylaminosulfonyl, $NR_{10}R_{11}$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from oxo, OH, $NR_{10}R_{11}$, $C_{1-6}$ branched or unbranched alkyl, $C_{3-7}$cycloalkyl, phenyl, naphthyl, heteroaryl, aminocarbonyl and mono- or di($C_{1-3}$)alkylaminocarbonyl;

$R_3$ is H, halogen, OH, $(CH_2)_nNR_{10}R_{11}$, $CONR_{10}R_{11}$, $(CH_2)_nCO_2R_{12}$; $C_{1-3}$alkyl optionally substituted with OH, $C_{1-3}$ alkoxy optionally halogenated or $C_{1-3}$ alkylthio;

$R_4$ and $R_5$ together with the atoms to which they are attached complete a fused ring system of the formulas A or B:

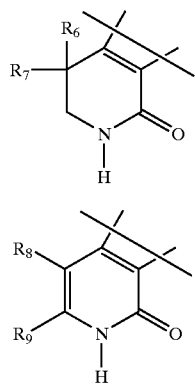

$R_6$ is $C_{1-3}$alkyl or H;

$R_7$ is $C_{1-6}$alkyl branched or unbranched or H;

$R_8$ is H, $C_{1-6}$alkyl branched or unbranched, saturated or unsaturated, optionally substituted with phenyl, OH or $C_{1-3}$alkoxy; or $R_8$ is $(CH_2)_mNR_{10}R_{11}$, $(CH_2)_mNR_{10}COR_{12}$, $(CH_2)_nCO_2R_{12}$, $(CH_2)_nCONR_{10}R_{11}$; or $R_8$ is phenyl or heteroaryl, each being optionally substituted with $C_{1-3}$alkyl, $C_{1-3}$alkoxy, OH, —$SO_3H$ or halogen;

$R_9$ is H, CN or $CONR_{10}R_{11}$; or $R_9$ is $C_{1-10}$alkyl branched or unbranched, $C_{3-10}$cycloalkyl, $C_5$cycloalkenyl, $C_{2-6}$ alkenyl, $C_{2-6}$ alkynyl each being optionally substituted with one or more $C_{3-10}$cycloalkyl, $C_{3-10}$cycloalkylidene, $C_{5-7}$cycloalkenyl, halogen, OH, oxo, CN, $C_{1-3}$alkoxy, $C_{1-3}$acyloxy, $NR_{10}R_{11}$, $NR_{10}CONR_{10}R_{11}$, $NR_{10}C(=NR_{10})NR_{10}R_{11}$, $NR_{10}COR_{12}$, $NR_{10}S(O)_pR_{12}$, $SR_{12}$, $CONR_{10}R_{11}$, $CO_2R_{12}$, $C(R_{10})=NNR_{10}R_{11}$, $C(R_{10})=NNR_{10}CONR_{10}R_{11}$, aryloxy, arylthio, aryl or heteroaryl; wherein each aryloxy, arylthio, aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl, heteroaryl, or heterocycle, wherein each aryl, heteroaryl or heterocycle is optionally substituted with one to three groups selected from $C_{1-3}$alkyl optionally substituted with phenyl or $NR_{10}C(=NR_{10})NR_{10}R_{11}$, $C_{1-3}$alkoxy, halogen, CN, oxo, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 5 or 6 membered aromatic or nonaromatic carbocyclic ring optionally substituted by one or two $C_{1-3}$alkyl, OH, oxo or $(CH_2)_nNR_{10}R_{11}$, or optionally spiro-fused to a 1,3 dioxolane group or 1,3 dithiolane group, each 1,3 dioxolane group or 1,3 dithiolane group optionally substituted by $C_{1-6}$alkyl, $C_{1-6}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, aryl$C_{1-3}$alkyl or heteroaryl are optionally substituted with OH, $C_{1-3}$alkoxy, CN, $NO_2$, $C_{1-3}$acyloxy, $CO_2R_{12}$, $NR_{13}R_{14}$, $O(CH_2)_{2-4}NR_{13}R_{14}$, aryl or heteroaryl;

or $R_{10}$ and $R_{11}$ together form a 3–7 member alkylene chain completing a ring about the N atom to which they are attached; wherein said alkylene chain is optionally interrupted by O, $S(O)_p$, and $NR_{13}$; and wherein said ring is optionally substituted by $C_{1-3}$ alkyl, $C_{1-3}$alkoxy, OH, —$(CH_2)_nNR_{13}R_{14}$, $CONR_{13}R_{14}$ or $NR_{13}COR_{14}$;

$R_{12}$ is H, $C_{1-6}$alkyl or $C_{3-8}$cycloalkyl wherein each alkyl or cycloalkyl is optionally substituted with phenyl, OH, $C_{1-3}$alkoxy or $NR_{13}R_{14}$; or $R_{12}$ is phenyl or heterocycle, optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$;

$R_{15}$ is H or $C_{1-3}$ alkyl;

m is 1–4; n is 0–3 and p is 0–2; or a pharmaceutically acceptable ester or salt thereof; with the proviso that at least one or more of Ra, $Ar_1$, $R_8$ and $R_9$ are or contain a heterocycle or heteroaryl.

2. The compound according to claim 1 wherein $Ar_1$ is a) a cycloalkyl group selected from cyclopropyl, cyclobutyl, cyclopentanyl, cyclohexanyl, cycloheptanyl;

b) a cycloalkenyl group selected from cyclopentenyl, cyclohexenyl, cycloheptenyl;

c) phenyl, naphthyl; indanyl, indenyl, dihydronaphthyl, tetrahydronaphthyl, fluorenyl;

d) heteroaryl selected from prindinyl, pyrimidinyl, pyrazinyl, pyridazinyl, pyrrolyl, imidazolyl, pyrazolyl, thienyl, furyl, isoxazolyl, isothiazolyl, oxazolyl, oxadiazolyl, thiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl, and indazolyl, or a fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; or e) a heterocycle selected from pyrrolinyl, pyrrolidinyl, pyrazolinyl, pyrazolidinyl, piperidinyl, morpholinyl, thiomorpholinyl, pyranyl, thiopyranyl, piperazinyl and indolinyl, wherein each of the above $Ar_1$ are optionally substituted by one or more $R_1$, $R_2$ and $R_3$;

$R_a$ is H, $C_{1-6}$alkyl, $C_{2-5}$alkenyl, $C_{2-5}$alkynyl, phenyl or heteroaryl selected from pyridinyl, pyridazinyl, pyrimidinyl, pyrazinyl, oxazolyl, pyrazolyl, imidazolyl, furyl, thiazolyl and thienyl; each $R_a$ being optionally substituted with one or more phenyl, halogen, $C_{1-3}$alkyl, $C_{1-3}$alkoxy, OH, oxo, or $NR_{10}R_{11}$; wherein $R_a$ is at the 4-position;

$R_1$ and $R_2$ are as hereinabove defined;

$R_3$ is H, halogen, methyl, methoxy, hydroxymethyl or OH;

$R_8$ is H, $C_{1-3}$alkyl branched or unbranched, saturated or unsaturated, optionally substituted with OH; or $R_8$ is $(CH_2)_{2-3}NR_{10}R_{11}$, $(CH_2)_nCO_2R_{12}$ or $(CH_2)_nCONR_{10}R_{11}$;

$R_9$ is CN or $CONR_{10}R_{11}$; or $R_9$ is $C_{1-3}$alkyl branched or unbranched, $C_{2-4}$ alkenyl, $C_{2-4}$alkynyl each being optionally substituted with one or more $C_{5-7}$cycloalkyl, $C_{5-7}$cycloalkylidene, $C_{5-7}$cycloalkenyl, OH, CN, $C_{1-3}$acyloxy, $NR_{10}R_{11}$, $NR_{10}CONR_{10}R_{11}$, $NR_{10}C(=NR_{10})NR_{10}R_{11}$, $NR_{10}COR_{12}$, $NR_{10}S(O)_pR_{12}$, $CONR_{10}R_{11}$, $CO_2R_{12}$, $C(R_{10})=NNR_{10}R_{11}$, $C(R_{10})=NNR_{10}CONR_{10}R_{11}$, aryl or heteroaryl; wherein each aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl, heteroaryl or heterocycle, each optionally substituted with one to three groups selected from $C_{1-3}$alkyl optionally substituted with phenyl or $NR_{10}C(=NR_{10})NR_{10}R_{11}$, $C_{1-3}$alkoxy, halogen, CN, oxo, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 5 or 6 membered aromatic or nonaromatic carbocyclic ring optionally substituted by $C_{1-3}$alkyl or OH, or optionally spiro-fused to a 1,3 dioxolane group or 1,3 dithiolane group, each 1,3 dioxolane group or 1,3 dithiolane group optionally substituted by $C_{1-3}$alkyl, $C_{1-3}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, benzyl and phenyl; wherein said alkyl, cycloalkyl, benzyl or phenyl are optionally substituted with OH, $C_{1-3}$alkoxy, $C_{1-3}$acyloxy, CN, $NO_2$, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy, OH, $-(CH_2)_nNR_{13}R_{14}$, $CONR_{13}R_{14}$ or $NR_{13}COR_{14}$;

$R_{12}$ is H, $C_{1-6}$alkyl or $C_{5-7}$cycloalkyl, each optionally substituted with phenyl, OH, $C_{1-3}$alkoxy or $NR_{13}R_{14}$; or $R_{12}$ is phenyl or heterocycle, each optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$; and $R_{15}$ is H.

3. The compound according to claim 2 wherein:

$Ar_1$ is phenyl, or pyridyl, wherein each is optionally substituted by one or more $R_1$, $R_2$ and $R_3$ as defined below;

X is NH or $N-CH_3$;

Y is NH and $R_a$ is H, hydroxy$C_{1-2}$alkyl, 2-hydroxyethylaminonmethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl;

$R_1$ and $R_2$ are the same or different and selected from: H, halogen, $C_{1-3}$ alkyl, wherein the $C_{1-3}$alkyl are optionally partially or fully halogenated, $NO_2$, $NR_{13}R_{14}$;

$R_3$ is H, halogen, methoxy or methyl;

$R_4$ and $R_5$ together complete a fused ring of formula B;

$R_8$ is H, $C_{1-3}$alkyl optionally substituted with OH; or $R_8$ is $(CH_2)_{2-3}NR_{10}R_{11}$ or $CO_2R_{12}$;

$R_9$ is CN; or $R_9$ is methyl, $C_{2-3}$ alkenyl or $C_{2-3}$ alkynyl, each being optionally substituted with one or more $C_{5-7}$cycloalkylidene, $C_{5-7}$cycloalkenyl, OH, CN, $NR_{10}R_{11}$, $NR_{10}CONR_{10}R_{11}$, $NR_{10}COR_{12}$, $NR_{10}S(O)_pR_{12}$, $CONR_{10}R_{11}$, $CO_2R_{12}$, $C(R_{10})=NNR_{10}R_{11}$ or heteroaryl;

or $R_9$ is aryl or heteroaryl optionally substituted with one to three groups selected from $C_{1-3}$alkyl optionally substituted with phenyl, $C_{1-3}$alkoxy, halogen, amino or $CONH_2$;

or $R_8$ and $R_9$ together form a cyclopentene ring spiro-fused to a 1,3 dioxolane group, said 1,3 dioxolane group being optionally substituted by $C_{1-3}$alkyl, $C_{1-3}$alkoxy, OH or $(CH_2)_nNR_{10}R_{11}$;

$R_{10}$ and $R_{11}$ may be the same or different and are each independently selected from H, OH, $C_{1-3}$alkoxy, $C_{1-3}$alkyl branched or unbranched, $C_{5-7}$cycloalkyl or phenyl, wherein said alkyl, cycloalkyl or phenyl are optionally substituted with OH, $C_{1-3}$alkoxy, $C_{1-3}$acyloxy, $NO_2$, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy,OH, $(CH_2)_nNR_{13}R_{14}$ $CONR_{13}R_{14}$ or $NR_{13}COR_{14}$;

$R_{12}$ is H, $C_{1-3}$alkyl or $C_{5-7}$cycloalkyl, each optionally substituted with phenyl, OH, $C_{1-3}$alkoxy or $NR_{13}R_{14}$; or $R_{12}$ is phenyl or is a saturated, 4- to 6-membered nitrogen-containing heterocycle, each optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-3}$alkyl optionally substituted with $C_{1-3}$alkoxy or OH;

or $R_{13}$ and $R_{14}$ together form a chain completing a ring, said chain is $(CH_2)_{4-5}$ or $(CH_2)_2O(CH_2)_2$.

4. The compound according to claim 3 wherein:

$Ar_1$ is phenyl;

$R_a$ is H or hydroxymethyl;

$R_1$ and $R_2$ are the same or different and selected from: halogen, methyl optionally partially or fully halogenated, $NO_2$ and $NH_2$;

83

$R_3$ is H, chloro, fluoro, bromo or methoxy;

$R_{10}$ and $R_{11}$ may be the same or different and are each independently selected from H, OH, methoxy, $C_{1-3}$alkyl branched or unbranched or $C_{5-7}$cycloalkyl, wherein said alkyl or cycloalkyl are optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl, $NR_{13}R_{14}$, $CONR_{13}R_{14}$ or $NR_{13}COR_{14}$; and $R_{12}$ is $C_{1-3}$alkyl optionally substituted with morpholino; or $R_{12}$ is phenyl or is azetidinyl, pyrrolidinyl or piperidinyl, each optionally substituted with one to three groups selected from $C_{1-3}$alkyl, $C_{1-3}$alkoxy and halogen.

5. A compound according to claim 1, wherein:

Y is $NR_{15}$, S or O;

$R_a$ is H, $C_{1-10}$alkyl, $C_{2-10}$alkenyl or $C_{2-10}$alkynyl, each of which may be branched or cyclic; or $R_a$ is aryl or heteroaryl; wherein each $R_a$ is independently optionally substituted with one or more $C_{1-3}$alkyl, $C_{1-6}$alkoxy, halogen, OH, oxo, $NR_{10}R_{11}$, aryl or heteroaryl, each aryl or heteroaryl being optionally substituted with one or more groups selected from halogen, OH, $C_{1-3}$alkyl, $C_{1-3}$alkoxy, hydroxy$C_{1-3}$alkyl and $(CH_2)_mNR_{10}R_{11}$; and wherein $R_a$ is attached at the 4- or 5- position;

$R_1$ and $R_2$ are the same or different and selected from H, halogen, CN, $NO_2$, $C_{1-10}$ branched or unbranched saturated or unsaturated alkyl, $C_{1-10}$ branched or unbranched alkoxy, $C_{1-10}$ branched or unbranched acyl, $C_{1-10}$ branched or unbranched acyloxy, $C_{1-10}$ branched or unbranched alkylthio, aminosulfonyl, di-$(C_{1-3})$alkylaminosulfonyl, $NR_{10}R_{11}$, aryl, aroyl, aryloxy, arylsulfonyl, heteroaryl and heteroaryloxy; wherein the abovementioned $R_1$ and $R_2$ are optionally partially or fully halogenated or optionally substituted with one to three groups independently selected from oxo, OH, $NR_{10}R_{11}$, $C_{1-6}$ branched or unbranched alkyl, $C_{3-7}$cycloalkyl, phenyl, naphthyl, heteroaryl, aminocarbonyl and mono- or di($C_{1-3}$)alkylaminocarbonyl;

$R_3$ is H, halogen, OH, $(CH_2)_nNR_{10}R_{11}$, $(CH_2)_nCO_2R_{12}$; $C_{1-3}$alkyl optionally substituted with OH, $C_{1-3}$ alkoxy optionally halogenated or $C_{1-3}$ alkylthio;

$R_4$ and $R_5$ together with the atoms to which they are attached complete a fused ring system of the formulas A or B:

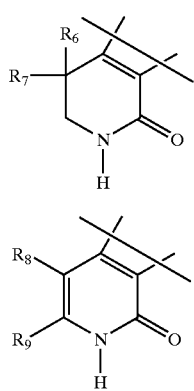

$R_6$ is $C_{1-3}$alkyl or H;

84

$R_7$ is $C_{1-6}$alkyl branched or unbranched or H; $R_8$ is H, $C_{1-6}$alkyl branched or unbranched, saturated or unsaturated, optionally substituted with phenyl, OH or $C_{1-3}$alkoxy; or $R_8$ is $(CH_2)_mNR_{10}R_{11}$, $(CH_2)_mNR_{10}COR_{12}$, $(CH_2)CO_2R_{12}$, $(CH_2)CONR_{10}R_{11}$; or $R_8$ is phenyl or heteroaryl, each being optionally substituted with $C_{1-3}$alkyl, $C_{1-3}$alkoxy, OH, —$SO_3H$ or halogen;

$R_9$ is H; or $R_9$ is $CH_{1-10}$alkyl branched or unbranched, $C_{3-10}$cycloalkyl, $C_{2-6}$ alkenyl, $C_{2-6}$ alkynyl each being optionally substituted with one or more halogen, OH, oxo, CN, $C_{1-3}$alkoxy, $NR_{10}R_{11}$, $NR_{10}COR_{12}$, $SR_{12}$, $CONR_{10}R_{11}$, $CO_2R_{12}$, aryloxy, arylthio, aryl or heteroaryl; wherein each aryloxy, arylthio, aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl or heteroaryl, wherein each aryl or heteroaryl is optionally substituted with one to three groups selected from $C_{1-3}$alkyl optionally substituted with phenyl, $C_{1-3}$alkoxy, halogen, $(CH_2)_nNR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 6 membered aromatic or nonaromatic carbocyclic ring optionally substituted by one or two OH, oxo or $(CH_2)_nNR_{10}R_{11}$;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, aryl, aryl$C_{1-3}$alkyl and heteroaryl; wherein said alkyl, cycloalkyl, aryl, aryl$C_{1-3}$alkyl or heteroaryl are optionally substituted with OH, $C_{13}$alkoxy, $C_{1-3}$acyloxy, $CO_2R_{12}$, $NR_{13}R_{14}$, $O(CH_2)_{2-4}NR_{13}R_{14}$, aryl or heteroaryl;

or $R_{10}$ and $R_{11}$ together form a 3–7 member alkylene chain completing a ring about the N atom to which they are attached; wherein said alkylene chain is optionally interrupted by O, $S(O)_p$, and $NR_{13}$; and wherein said ring is optionally substituted by $C_{1-3}$ alkyl, $C_{1-3}$alkoxy, OH or —$(CH_2)_nNR_{13}R_{14}$;

$R_{12}$ is H, $C_{1-6}$alkyl or $C_{3-8}$cycloalkyl wherein each alkyl or cycloalkyl is optionally substituted with phenyl, OH, $C_{1-3}$alkoxy or $NR_{13}R_{14}$; or $R_{12}$ is phenyl, optionally substituted with one to three groups selected from $C_{1-3}$alkyl, $C_{1-3}$alkoxy, halogen, $(CH_2)_mNR_{10}R_{11}$, $(CH_2)_nCONR_{10}R_{11}$ and $O(CH_2)_{2-4}NR_{10}R_{11}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$;

$R_{15}$ is H or $C_{1-3}$ alkyl;

m is 1–4; n is 0–3 and p is 0–2; or a pharmaceutically acceptable ester or salt thereof.

6. A compound according to claim 5, wherein:

$R_a$ is H, $C_{1-6}$alkyl, $C_{2-5}$alkenyl, $C_{2-5}$alkynyl, phenyl or heteroaryl selected from: pyridinyl, pyridazinyl, pyrimidinyl, pyrazinyl, oxazolyl, pyrazolyl, imidazolyl, furyl, thiazolyl and thienyl; each $R_a$ being optionally substituted with one or more phenyl, halogen, $C_{1-3}$alkyl, $C_{1-3}$ alkoxy, OH, oxo, or $NR_{10}R_{11}$; wherein $R_a$ is at the 4-position;

$R_3$ is H, halogen, methyl, niethoxy, hydroxymethyl or OH;

$R_8$ is H, $C_{1-3}$alkyl branched or unbranched, saturated or unsaturated, optionally substituted with OH; or $R_8$ is $(CH_2)_{2-3}NR_{10}R_{11}$, $(CH_2)_nCO_2R_{12}$ or $(CH_2)_n$ $CONR_{10}R_{11}$;

$R_9$ is $C_{1-3}$alkyl branched or unbranched, $C_{2-4}$ alkenyl, $C_{2-4}$alkynyl each being optionally substituted with one or more OH, CN, $NR_{10}R_{11}$, $CONR_{10}R_{11}$, $C_2R_{12}$, aryl or heteroaryl; wherein each aryl or heteroaryl is optionally substituted with $C_{1-3}$alkyl, $C_{1-3}$alkoxy, halogen, $(CH_2)_nNR_{10}R_{11}$ or $O(CH_2)_{2-4}NR_{10}R_{11}$;

or $R_9$ is aryl or heteroaryl optionally substituted with one to three groups selected from $C_{1-3}$alkyl optionally substituted with phenyl, $C_{1-3}$alkoxy, halogen, $(CH_2)_n$ $NR_{10}R_{11}$, $(CH_2)_nCO_2R_{12}$; $(CH_2)_nCONR_{10}R_{11}$ and $O(CH_2)_{2-4}NR_{10}R_{11}$;

or $R_8$ and $R_9$ together form a saturated or unsaturated 6 membered aromatic or nonaromatic carbocyclic ring optionally substituted by OH;

$R_{10}$ and $R_{11}$ may be the same or different and are each independently selected from H, OH, $C_{1-3}$alkoxy, $C_{1-6}$alkyl branched or unbranched, $C_{3-8}$cycloalkyl, benzyl and phenyl; wherein said alkyl, cycloalkyl, benzyl or phenyl are optionally substituted with OH, $C_{1-3}$alkoxy, $C_{1-3}$acyloxy, $CO_2R_{12}$, $NR_{13}R_{14}$,$O(CH_2)_{2-4}$ $NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy, OH or —$(CH_2)_nNR_{13}R_{14}$;

$R_{12}$ is H or $C_{1-6}$alkyl optionally substituted with phenyl, OH, $C_{1-3}$alkoxy or $NR_{13}R_{14}$;

$R_{13}$ and $R_{14}$ are each independently selected from H and $C_{1-6}$ alkyl optionally substituted with $C_{1-3}$alkoxy, OH or phenyl;

or $R_{13}$ and $R_{14}$ together form a chain completing a ring, said chain is $(CH_2)_{4-5}$ or $(CH_2)_2O(CH_2)_2$; and $R_{15}$ is H.

7. The compound according to claim 6 wherein:

$Ar_1$ is phenyl, or pyridyl;

X is NH or N—$CH_3$;

Y is NH and $R_a$ is H, hydroxy$C_{1-2}$alkyl, 2-hydroxyethylaminomethyl, methoxybenzylaminomethyl, pyridinyl optionally halogenated, phenyl, 3-hydroxy-2-oxo-propyl, vinyl or $C_{3-5}$alkynyl substituted by $C_{1-3}$alkoxy or phenyl;

$R_1$ and $R_2$ are the same or different and selected from: halogen, $C_{1-3}$ alkyl, wherein the $C_{1-3}$ alkyl are optionally partially or fully halogenated, $NO_2$, $NR_{13}R_{14}$;

$R_3$ is H, halogen, methoxy or methyl;

$R_4$ and $R_5$ together complete a fused ring of formula B;

$R_8$ is H, $C_{1-3}$alkyl optionally substituted with OH; or $R_8$ is $(CH_2)_{2-3}NR_{10}R_{11}$ or $CO_2R_{12}$;

$R_9$ is methyl or $C_{2-3}$ alkenyl each being optionally substituted with one or more OH, CN, $NR_{10}R_{11}$, $CONR_{10}R_{11}$, or $CO_2R_{12}$;

or $R_9$ is heteroaryl optionally substituted with one to three groups selected from $C_{1-3}$alkyl optionally substituted with phenyl, $C_{1-3}$alkoxy, halogen or amino;

$R_{10}$ and $R_{11}$ may be the same or different and are each independently selected from H, OH, $C_{1-3}$alkoxy, $C_{1-3}$alkyl branched or unbranched, optionally substituted with OH, $C_{1-3}$alkoxy, $C_{1-3}$acyloxy, $CO_2R_{12}$, $NR_{13}R_{14}$, $O(CH_2)_{2-4}NR_{13}R_{14}$ or phenyl;

or $R_{10}$ and $R_{11}$ together form morpholino, pyrrolidinyl, piperazinyl or piperidinyl each optionally substituted by $C_{1-3}$ alkyl, $C_{1-3}$alkoxy or OH;

$R_{12}$ is H or $C_{1-3}$alkyl optionally substituted with phenyl, OH, $C_{1-3}$alkoxy or $NR_{13}R_{14}$;

$R_{13}$ and $R_{14}$ are each independently selected from H and $C_{1-3}$alkyl optionally substituted with $C_{1-3}$alkoxy or OH;

or $R_{13}$ and $R_{14}$ together form a chain completing a ring, said chain is $(CH_2)_{4-5}$ or $(CH_2)_2O(CH_2)_2$.

8. The compound according to claim 7 wherein:

$Ar_1$ is phenyl;

$R_a$ is H or hydroxymethyl;

$R_1$ and $R_2$ are the same or different and selected from: halogen, methyl optionally partially or fully halogenated, $NO_2$ and $NH_2$;

$R_3$ is H, chloro, fluoro, bromo or methoxy, $R_{10}$ and $R_{11}$ may be the same or different and are each independently selected from H, OH, methoxy, $C_{1-3}$alkyl branched or unbranched, optionally substituted with OH, $NR_{13}R_{14}$ or phenyl;

or $R_{10}$ and $R_{11}$ together form morpholino, pyrrolidinyl, piperazinyl or piperidinyl each optionally substituted by $C_{1-2}$ alkyl, and $R_{12}$ is $C_{1-3}$alkyl optionally substituted with morpholino.

9. A compound selected from:

3-[2-(2,6-Dichlorophenylamino)-1-methyl-9-oxo-8,9-dihydro-1H-imidazo[4,5-h]isoquinolin-7-yl]-acrylic acid 4-morpholine amide;

2-(2,6-Dichlorophenylamino)-1,7-dimethyl-9-oxo-1,8-dihydro -imidazo[4,5-h]-isoquinoline-6-carboxylic acid 2-(4-moropholino)ethyl ester;

2-(2,6-Dichlorophenylamino)-1,6-dimethyl-7-oxazol-5-yl-1,8-dihydro-imidazo[4,5-h]isoquinolin-9-one;

2-(2,6-Dichlorophenylamino)-1,6dimethyl-7-(3-morpholin-4-yl-propen-1-yl)-1,8-dihydro-imidazo[4,5-h]-isoquinolin-9-one;

2-(2,6-Dichlorophenylamino)-1-methyl-7-oxazol-5-yl-1,8-dihydro-imidazo[4,5-h]isoquinolin-9-one;

2-(2,6-Dichlorophenylamino)-1,6-dimethyl-7-(3-pyrrolidin-1-yl-propen-1-yl)-1,8-dihydro-imidazo[4,5-h]-isoquinolin-9-one;

2-(2,6-Dichlorophenylamino)-1,6-dimethyl-7-(4-methylpiperazin-1-yl-propen-1-yl)-1,8-dihydro-imidazo[4,5-h]-isoquinolin-9-one;

2-(2,6-Dichlorophenylamino)-1,6-dimethyl-7-(3-piperidin-1-yl-propen-1-yl)-1,8-dihydro-imidazo[4,5-h]-isoquinolin-9-one;

2(2,6-Dichlorophenylamino)-6-methyl-7-oxazol-5-yl-1,8-dihydro-imidazo[4,5-h]isoquinolin-9-one;

2-(2,6-Dichlorophenylamino)-1,6-dimethyl-7-[3-(2-pyrrolidin-1-ylmethylpyrrolidin-1-yl)-propen-1-yl]-1,8-dihydro-imidazo[4,5-h]-isoquinolin-9-one;

7-[3-(2S-Aminomethylpyrrolidin-1-yl)-propen-1-yl]-2-(2,6-dichlorophenylamino)-1,6-dimethyl-1,8-dihydro-imidazo[4,5-h]-isoquinolin-9-one;

1-{3-[2-(2,6-dichlorophenylamino)-1,6-dimethyl-9-oxo-8,9-dihydro-1H-imidazo[4,5-h]isoquinolin-7-yl]-propenyl}-L-proline carboxamide;

1-{3-[2-(2,6-dichlorophenylamino)-1,6-dimethyl-9-oxo-8,9-dihydro-1H-imidazo[4,5-h]isoquinolin-7-yl]-propenyl}-piperidine-3-carboxamide;

7-[3-(3-Aminopyrrolidin-1-yl)-propen-1-yl]-2-(2,6-dichlorophenylamino)-1,6-dimethyl-1,8-dihydro-imidazo[4,5-h]-isoquinolin-9-one;

2-(2,6-Dichlorophenylamino)-1,6dimethyl-7-[3-(3-acetamidopyrrolidin-1-yl)-propen-1-yl]-1,8-dihydro-imidazo[4,5-h]-isoquinolin-9-one;

2-(2,6-Dichlorophenylamino)-1,6-dimethyl-7-[3-(3-dimethylaminopyrrolidin-1-yl)-propen-1-yl]-1,8-dihydro-imidazo[4,5-h]-isoquinolin-9-one;

1-{3-[2-(2,6-Dichlorophenylamino)-1,6-dimethyl-9-oxo-8,9-dihydro-1H-imidazo[4,5-h]isoquinolin-7-yl]-propenyl}-piperidine-2-carboxamide;

7-[3-(3-Aminomethylpiperidin-1-yl)-propen-1-yl]-2-(2,6-dichlorophenylamino)-1,6-dimethyl-1,8-dihydro-imidazo[4,5-h]-isoquinolin-9-one;

1-{3-[2-(2,6-Dichlorophenylamino)-1,6-dimethyl-9-oxo-8,9-dihydro-1H-imidazo[4,5-h]isoquinolin-7-yl]-propenyl}-piperidine-3-carboxylic acid diethylamide;

Piperidine-3-carboxylic acid {3-[2-(2,6-dichlorophenylamino)-1,6-dimethyl-9-oxo-8,9-dihydro-1H-imidazo[4,5-h]isoquinolin-7-yl]-Propenyl}amide;

L-Proline {3-[2-(2,6-dichlorophenylamino)-1,6-dimethyl-9-oxo-8,9-dihydro-1H-imidazo[4,5-h]isoquinolin-7-yl]-propenyl}amide;

D-Proline {3-[2-(2,6-dichlorophenylamino)-1,6-dimethyl-9-oxo-8,9-dihydro-1H-imidazo[4,5-h]isoquinolin-7-yl]-propenyl}amide;

L-Azetidine-2-carboxylic acid {3-[2(2,6-dichlorophenylamino)-1,6-dimethyl-9-oxo-8,9-dihydro-1H-imidazo[4,5-h]isoquinolin-7-yl]-propenyl}amide and Piperidine-2-carboxylic acid {3-[2-(2,6-dichlorophenylamino)-1,6-dimethyl-9-oxo-8,9-dihydro-1H-imidazo[4,5-h]isoquinolin-7-yl]-propenyl}amide;

or a pharmaceutically acceptable salt or ester thereof.

10. A compound according to claim 9 selected from:

3-[2,6-Dichlorophenylamino)-1-methyl-9-oxo-8,9-dihydro-1H-imidazo[4,5-h]isoquinolin-7-yl]-acrylic acid 4-morpholine amide;

2-(2,6-Dichlorophenylamino)-1,7-dimethyl-9-oxo-1,8dihydro-imidazo[4,5-h]isoquinoline-6-carboxylic acid 2-(4-morpholino)ethyl ester;

2-(2,6-Dichlorophenylamino)-1,6-dimethyl-7-oxazol-5-yl-1,8-dihydro-imidazo[4,5-h]isoquinolin-9-one;

2-(2,6-Dichlorophenylamino)-1,6-dimethyl-7-(3-morpholin-4-yl-propen-1-yl)-1,8-dihydro-imidazo[4,5-h]isoquinolin-9-one;

2-(2,6-Dichlorophenylamino)-1-methyl-7-oxazol-5-yl-1,8-dihydro-imidazo[4,5-h]isoquinolin-9-one;

2-(2,6-Dichlorophenylamino)-1,6-dimethyl-7-(3-pyrrolidin-1-yl-propen-1-yl)-1,8-dihydro-imidazo[4,5-h]-isoquinolin-9-one;

2-(2,6-Dichlorophenylamino)-1,6-dimethyl-7-(4-methylpiperazin-1-yl-propen-1-yl)-1,8-dihydro-imidazo[4,5-h]-isoquinolin-9-one;

2-(2,6-Dichlorophenylamino)-1,6-dimethyl-7-(3-piperidin-1-yl-propen-1-yl)-1,8-dihydro-imidazo[4,5-h]-isoquinolin-9-one;

2(2,6Dichlorophenylamino)-6-methyl-7-oxazol-5-yl-1,8-dihydro-imidazo[4,5-h]isoquinolin-9-one;

2-(2,6-Dichlorophenylamino)-1,6-dimethyl-7-[3-(2-pyrrolidin-1-ylmethylpyrrolidin-1-yl)-propen-1-yl]-1,8dihydro-imidazo[4,5-h]-isoquinolin-9-one;

7-[3-(2S-Aminomethylpyrrolidin-1-yl)-propen-1-yl]-2-(2,6-dichlorophenylamino)-1,6-dimethyl-1,8-dihydro-imidazo[4,5-h]-isoquinolin-9-one;

1-{3-[2-(2,6-dichlorophenylamino)-1,6-dimethyl-9-oxo-8,9-dihydro-1H-imidazo[4,5-h]isoquinolin-7-yl]-propenyl}-L-proline carboxamide;

1-{3-[2-(2,6-dichlorophenylamino)-1,6-dimethyl-9-oxo-8,9-dihydro-1H-imidazo[4,5-h]isoquinolin-7-yl]-propenyl}-piperidine-3-carboxamide;

7-[3-(3-Aminopyrrolidin-1-yl)-propen-1-yl-2-(2,6-dichlorophenylamino)-1,6-dimethyl-1,8-dihydro-imidazo[4,5-h]-isoquinolin-9-one;

2-(2,6-Dichlorophenylamino)-1,6dimethyl-7-[3-(3-acetamidopyrrolidin-1-yl)-propen-1-yl]-1,8-dihydro-imidazo[4,5-h]-isoquinolin-9-one;

2-(2,6-Dichlorophenylamino)-1,6dimethyl-7-[3-(3-dimethylaminopyrrolidin-1-yl)-propen-1-yl]-1,8-dihydro-imidazo[4,5-h]-isoquinolin-9-one;

1-{3-[2-(2,6-Dichlorophenylamino)-1,6-dimethyl-9-oxo-8,9-dihydro-1H-imidazo[4,5-h]isoquinolin-7-yl]-propenyl}-piperidine-2-carboxamide;

7-[3-(3-Aminometbylpiperidin-1-yl)-propen-1-yl]-2-(2,6-dichlorophenylamino)-1,6-dimethyl-1,8-dihydro-imidazo[4,5-h]-isoquinolin-9-one;

1-{3-[2-(2,6-Dichlorophenylamino)-1,6-dimethyl-9-oxo-8,9-dihydro-1H-imidazo[4,5-h]isoquinolin-7-yl]-propenyl}-piperidine-3-carboxylic acid diethylamide;

Piperidine-3-carboxylic acid {3-[2-(2,6-dichlorophenylamino)-1,6-dimethyl-9-oxo-8,9-dihydro-1H-imidazo[4,5-h]isoquinolin-7-yl]-propenyl}amide;

L-Proline {3-[2-(2,6-dichlorophenylamino)-1,6dimethyl-9-oxo-8,9-dihydro-1H-imidazo[4,5-h]isoquinolin-7-yl]-propenyl }amide;

D-Proline {3-[2-(2,6-dichlorophenylamino)-1,6-dimethyl-9-oxo-8,9-dihydro-1H-imidazo[4,5-h]isoquinolin-7-yl]-propenyl}amide;

L-Azetidine-2-carboxylic acid {3-[2-(2,6-dichlorophenylamino)-1,6-dimethyl-9-oxo-8,9-dihydro-1H-imidazo[4,5-h]isoquinolin-7-yl]-propenyl}amide and Piperidine-2-carboxylic acid {3-[2-(2,6-dichlorophenylamino)-1,6-dimethyl-9-oxo-8,9-dihydro-1H-imidazo[4,5]isoquinolin-7-yl]-propenyl}amide.

11. The compound according to claim 9 wherein the compound is selected from:

3-[2-(2,6-Dichlorophenylamino)-1-methyl-9-oxo-8,9-dihydro-1H-imidazo[4,5-h]isoquinolin-7-yl]-acrylic acid 4-morpholine amide;

2-(2,6-Dichlorophenylamino)-1,7-dimethyl-9-oxo-1,8-dihydro-imidazo[4,5-h]isoquinoline-6-carboxylic acid 2-(4-moropholino)ethyl ester;

2-(2,6-Dichlorophenylamino)-1,6-dimethyl-7-oxazol-5-yl-1,8-dihydro-imidazo[4,5-h]isoquinolin-9-one;

2-(2,6-Dichlorophenylamino)-1,6-dimethyl-7-(3-morpholin-4-yl-propen-1-yl)-1,8-dihydro-imidazo[4,5-h]-isoquinolin-9-one;

2-(2,6-Dichlorophenylamino)-1-methyl-7-oxazol-5-yl-1,8-dihydro-imidazo[4,5-h]isoquinolin-9-one;

2-(2,6-Dichlorophenylamino)-1,6-dimethyl-7-(3-pyrrolidin-1-yl-propen-1-yl)-1,8-dihydro-imidazo[4,5-h]-isoquinolin-9-one;

2-(2,6-Dichlorophenylamino)-1,6-dimethyl-7-(4-methylpiperazin-1-yl-propen-1-yl)-1,8-dihydro-imidazo[4,5-h]-isoquinolin-9-one and 2-(2,6-Dichlorophenylamino)-1,6-dimethyl-7-(3-piperidin-1-yl-propen-1-yl)-1,8-dihydro-imidazo[4,5-h]-isoquinolin-9-one.

12. A pharmaceutical composition comprising a therapeutically effective amount of a compound according to claim 1, and one or more pharmaceutically acceptable carriers or adjuvants.

13. A method of treating an autoimmune disease, cancer or a cerebral ischemic condition, said method comprising administering to a patient in need thereof a therapeutically effective amount of a compound according to claim 1.

14. The method according to claim 13, wherein the autoimmune disease is selected from rheumatoid arthritis, multiple sclerosis, Guillain-Barre syndrome, Crohn's disease, ulcerative colitis, psoriasis, graft versus host disease, systemic lupus erythematosus, insulin-dependent diabetes mellitus and asthma.

15. The method according to claim 13 wherein the cancer is selected from a src-dependent tumor or a PDGF-dependent tumor.

16. The method according to claim 15, wherein the src-dependent tumor is selected from mammary carcinoma, colon carcinoma, melanoma and sarcoma.

17. The method according to claim 15, wherein the PDGF-dependent tumor is selected from ovarian cancer, prostate cancer and glioblastoma.

18. The method according to claim 13, wherein the cerebral ischemic condition is stroke.

19. A method of treating a disease selected from osteoporosis, Paget's disease, bone inflammation, and joint inflammation, said method comprising administering to a patient in need thereof a therapeutically effective amount of a compound according to claim 1.

20. A method of treating a disease selected from fibrotic diseases, restenosis and atherosclerosis, said method comprising administering to a patient in need thereof a therapeutically effective amount of a compound according to claims 1.

21. A method of enhancing or potentiating the effectiveness of radiation therapy by administering to a patient undergoing such therapy a therapeutically effective amount of compound according to claim 1.

22. A method of making a compound of the formula (I)

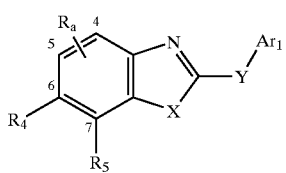

wherein X, $Ar_1$, $R_4$, $R_5$, $R_{15}$ and $R_a$ are as defined in claim 1, said process comprising:

a) reacting a compound of the formula(II) with $Ar_1NCS$ in a suitable solvent at about ambient to reflux temperature for about 3 to 24 hr to provide a compound of the formula (III);

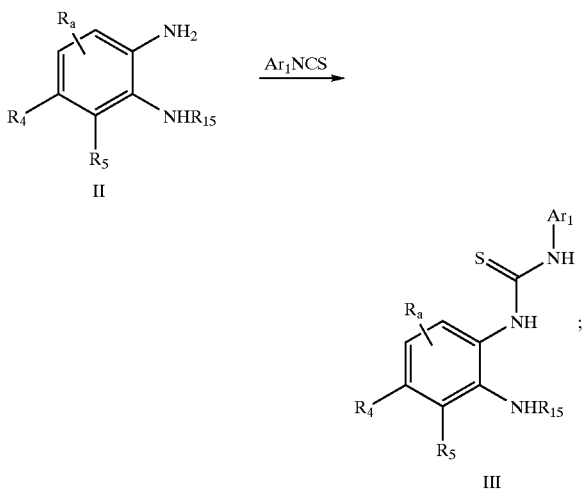

b) reacting the product (III) of step a) with a suitable activating agent chosen from 1,3-dicyclohexylcarbodiimide (DCC) and mercuric oxide in a suitable solvent at about ambient to reflux temperature to form a compound of the formula (I) as shown above or precursors thereof.

* * * * *